(12) United States Patent
Rudakov

(10) Patent No.: US 9,737,308 B2
(45) Date of Patent: Aug. 22, 2017

(54) CATHETER-ASSISTED TUMOR TREATMENT

(71) Applicant: Artventive Medical Group, Inc., San Marcos, CA (US)

(72) Inventor: Leon Rudakov, San Marcos, CA (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 733 days.

(21) Appl. No.: 14/101,171

(22) Filed: Dec. 9, 2013

(65) Prior Publication Data

US 2014/0371716 A1 Dec. 18, 2014
US 2017/0128076 A9 May 11, 2017

Related U.S. Application Data

(60) Provisional application No. 61/835,406, filed on Jun. 14, 2013, provisional application No. 61/900,321, (Continued)

(51) Int. Cl.
A61B 17/12 (2006.01)
A61B 17/00 (2006.01)

(52) U.S. Cl.
CPC ...... A61B 17/1215 (2013.01); A61B 17/1204 (2013.01); A61B 17/12109 (2013.01); A61B 17/12136 (2013.01); A61B 17/12145 (2013.01); A61B 17/12154 (2013.01); A61B 17/12168 (2013.01); A61B 17/12172 (2013.01);

(Continued)

(58) Field of Classification Search
CPC ........ A61B 17/12136; A61B 17/12109; A61B 17/1214–17/12154; A61B 17/12168–17/12177
See application file for complete search history.

(56) References Cited

U.S. PATENT DOCUMENTS 3,805,767 A 4/1974 Erb
3,868,956 A 3/1975 Alfidi et al.
(Continued)

FOREIGN PATENT DOCUMENTS

CN 2527227 Y 12/2002
EP 1166721 A2 1/2002
(Continued)

OTHER PUBLICATIONS

U.S. Appl. No. 14/281,797, filed May 19, 2014.
(Continued)

Primary Examiner — Laura Bouchelle
Assistant Examiner — Anh Bui
(74) Attorney, Agent, or Firm — Nathan S. Smith; McDermott Will & Emery LLP

(57) ABSTRACT

An implant can include a support component, a cover component, and a valve component. The valve component can be operable to permit flow through the implant. The implant can be delivered on a catheter, with one of the ends of the implant being selectively expanded to permit temporary occlusion of a vessel while delivering a material through the valve component to a downstream target region. The other end of the implant can thereafter be released such that the implant occludes the vessel, or the implant can be removed from the vessel entirely.

26 Claims, 27 Drawing Sheets

Related U.S. Application Data filed on Nov. 5, 2013, provisional application No. 61/835,461, filed on Jun. 14, 2013.

(52) U.S. Cl.
CPC .. *A61B 17/12177* (2013.01); *A61B 17/12186* (2013.01); *A61B 17/1214* (2013.01); *A61B 2017/00893* (2013.01); *A61B 2017/12054* (2013.01)

(56) References Cited

U.S. PATENT DOCUMENTS

| | | | |
|---|---|---|---|
| 3,918,431 A | 11/1975 | Sinnreich |
| 4,013,063 A | 3/1977 | Bucalo |
| 4,245,623 A | 1/1981 | Erb |
| 4,553,545 A | 11/1985 | Maass et al. |
| 4,649,922 A | 3/1987 | Wiktor |
| 4,682,592 A | 7/1987 | Thorsgard |
| 4,705,517 A | 11/1987 | DiPisa, Jr. |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,370 A | 9/1992 | McNamara et al. |
| 5,234,437 A | 8/1993 | Sepetka |
| 5,242,451 A | 9/1993 | Harada et al. |
| 5,242,452 A | 9/1993 | Inoue |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A | 12/1995 | Limon |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,607,445 A | 3/1997 | Summers |
| 5,656,036 A | 8/1997 | Palmaz |
| 5,674,287 A | 10/1997 | Slepian et al. |
| 5,693,083 A | 12/1997 | Baker et al. |
| 5,702,419 A | 12/1997 | Berry et al. |
| 5,725,552 A | 3/1998 | Kotula et al. |
| 5,733,329 A | 3/1998 | Wallace et al. |
| 5,772,668 A | 6/1998 | Summers et al. |
| 5,782,860 A | 7/1998 | Epstein et al. |
| 5,797,952 A | 8/1998 | Klein |
| 5,797,953 A | 8/1998 | Tekulve |
| 5,830,222 A | 11/1998 | Makower |
| 5,842,621 A | 12/1998 | Gschwind |
| 5,868,782 A | 2/1999 | Frantzen |
| 5,902,266 A | 5/1999 | Leone et al. |
| 5,922,009 A | 7/1999 | Epstein et al. |
| 5,925,063 A | 7/1999 | Khosravi |
| 5,925,074 A | 7/1999 | Gingras et al. |
| 5,928,260 A | 7/1999 | Chin et al. |
| 5,944,738 A | 8/1999 | Amplatz et al. |
| 5,954,766 A | 9/1999 | Zadno-Azizi et al. |
| 5,957,929 A | 9/1999 | Brenneman |
| 5,979,446 A | 11/1999 | Loy |
| 6,010,517 A | 1/2000 | Baccaro |
| 6,019,779 A | 2/2000 | Thorud et al. |
| 6,024,765 A | 2/2000 | Wallace et al. |
| 6,056,770 A | 5/2000 | Epstein et al. |
| 6,059,825 A | 5/2000 | Hobbs et al. |
| 6,083,257 A | 7/2000 | Taylor et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,258,119 B1 | 7/2001 | Hussein et al. |
| 6,283,983 B1 | 9/2001 | Makower et al. |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,485,524 B2 | 11/2002 | Strecker |
| 6,506,204 B2 | 1/2003 | Mazzocchi |
| 6,514,285 B1 | 2/2003 | Pinchasik |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Epstein et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |
| 6,974,473 B2 | 12/2005 | Barclay et al. |
| 6,984,244 B2 | 1/2006 | Perez et al. |
| 7,001,409 B2 | 2/2006 | Amplatz |
| 7,011,643 B2 | 3/2006 | Villafana et al. |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |
| 7,398,780 B2 | 7/2008 | Callister et al. |
| 7,458,986 B2 | 12/2008 | Schmitt |
| 7,476,232 B2 | 1/2009 | Deal |

(56) References Cited

U.S. PATENT DOCUMENTS

| | | |
|---|---|---|
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,631 B2 | 8/2010 | Roser et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,955,343 B2 | 6/2011 | Makower et al. |
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 | 2/2012 | Melsheimer |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,298,257 B2 | 10/2012 | Sepetka et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 8,808,342 B2 | 8/2014 | Ludwig |
| 8,834,544 B2 | 9/2014 | Gerrans et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0130684 A1 | 7/2003 | Brady et al. |
| 2003/0153972 A1 | 8/2003 | Helmus |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0212452 A1* | 11/2003 | Zadno-Azizi ......... A61F 2/0009 623/1.24 |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0029994 A1 | 2/2004 | Cheng et al. |
| 2004/0044360 A1 | 3/2004 | Lowe |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0049608 A1 | 3/2005 | Aznoian et al. |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0111771 A1 | 5/2006 | Ton et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1* | 5/2007 | Strecker ............... A61F 2/2412 623/1.23 |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0046092 A1 | 2/2008 | Davis et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0221657 A1 | 9/2008 | Laroya et al. |
| 2008/0221666 A1 | 9/2008 | Licata et al. |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0024072 A1* | 1/2009 | Criado ............... A61M 1/3655 604/9 |

(56) References Cited

U.S. PATENT DOCUMENTS

| | | |
|---|---|---|
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 | 5/2009 | Watson |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0094395 A1 | 4/2010 | Kellett |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0198328 A1 | 8/2010 | Hartley et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268201 A1 | 10/2010 | Tieu et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0092997 A1 | 4/2011 | Kang |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1* | 12/2011 | Rudakov .......... A61B 17/12145 606/127 |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089216 A1 | 4/2012 | Rapaport et al. |
| 2012/0095489 A1* | 4/2012 | Rudakov .......... A61B 17/12031 606/191 |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245614 A1 | 9/2012 | Drasler |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1 | 11/2012 | Kunis |
| 2012/0289988 A1 | 11/2012 | Riina et al. |
| 2012/0289994 A1 | 11/2012 | Larson et al. |
| 2012/0296408 A1 | 11/2012 | Jones et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053758 A1 | 2/2013 | Kibbe |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0073903 A1 | 3/2014 | Weber et al. |
| 2014/0128780 A1 | 5/2014 | Kennedy et al. |
| 2014/0207180 A1 | 7/2014 | Ferrera |
| 2014/0215792 A1 | 8/2014 | Leopold et al. |
| 2014/0222059 A1 | 8/2014 | Leopold et al. |
| 2014/0277085 A1 | 9/2014 | Mirigian et al. |
| 2015/0057700 A1 | 2/2015 | Chen et al. |
| 2015/0157329 A1 | 6/2015 | Rudakov et al. |
| 2015/0157333 A1 | 6/2015 | Leopold et al. |
| 2015/0223821 A1 | 8/2015 | Rudakov et al. |
| 2015/0290437 A1 | 10/2015 | Rudakov et al. |
| 2015/0313602 A1 | 11/2015 | Rudakov |
| 2015/0342611 A1 | 12/2015 | Leopold et al. |

FOREIGN PATENT DOCUMENTS

| | | |
|---|---|---|
| EP | 1188413 | 3/2002 |
| EP | 1317908 A2 | 6/2003 |
| EP | 1600110 | 11/2005 |
| EP | 1707233 A2 | 10/2006 |
| EP | 1752112 | 2/2007 |
| EP | 1813196 | 8/2007 |
| EP | 1820436 A2 | 8/2007 |
| EP | 1852073 | 11/2007 |
| EP | 2248471 A1 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 A | 2/2005 |
| GB | 2494820 A | 3/2013 |
| JP | H 07-000405 | 1/1995 |
| JP | 07-18501 | 7/1995 |
| JP | 2006-181015 A | 7/2006 |
| JP | 2010-532180 A | 10/2010 |
| JP | 2012-525859 A | 10/2012 |
| WO | WO-83/00997 A1 | 3/1983 |
| WO | WO-92/14408 | 9/1992 |
| WO | WO-94/00179 A1 | 1/1994 |
| WO | WO-95/24158 | 9/1995 |
| WO | WO-95/25480 A1 | 9/1995 |
| WO | WO-95/32018 | 11/1995 |
| WO | WO-96/18361 | 6/1996 |
| WO | WO-97/13463 A1 | 4/1997 |
| WO | WO-97/13471 A1 | 4/1997 |
| WO | WO-97/27893 | 8/1997 |
| WO | WO-97/27897 A1 | 8/1997 |
| WO | WO-97/27898 | 8/1997 |
| WO | WO-97/31672 A1 | 9/1997 |
| WO | WO-98/08456 A1 | 3/1998 |
| WO | WO-98/31308 | 7/1998 |
| WO | WO-98/34546 | 8/1998 |

(56) References Cited

FOREIGN PATENT DOCUMENTS

| | | |
|---|---|---|
| WO | WO-98/46115 A2 | 10/1998 |
| WO | WO-98/46119 A1 | 10/1998 |
| WO | WO-99/12484 A1 | 3/1999 |
| WO | WO-99/23976 A1 | 5/1999 |
| WO | WO-99/25273 A1 | 5/1999 |
| WO | WO-99/44542 A2 | 9/1999 |
| WO | WO-99/48545 A1 | 9/1999 |
| WO | WO-99/49793 A1 | 10/1999 |
| WO | WO-99/49910 A2 | 10/1999 |
| WO | WO-99/62430 A1 | 12/1999 |
| WO | WO-00/09195 | 2/2000 |
| WO | WO-00/16847 A1 | 3/2000 |
| WO | WO-00/27303 A2 | 5/2000 |
| WO | WO-00/67671 A1 | 11/2000 |
| WO | WO-01/32254 A1 | 5/2001 |
| WO | WO-01/64112 A1 | 9/2001 |
| WO | WO-01/80776 A1 | 11/2001 |
| WO | WO-01/80777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 A1 | 9/2003 |
| WO | WO-03/073962 A1 | 9/2003 |
| WO | WO-03/101518 A1 | 12/2003 |
| WO | WO-2004/006804 A1 | 1/2004 |
| WO | WO-2004/073557 A2 | 9/2004 |
| WO | WO-2005/020786 A2 | 3/2005 |
| WO | WO-2005/092241 | 10/2005 |
| WO | WO-2005/117755 A2 | 12/2005 |
| WO | WO-2006/017470 A2 | 2/2006 |
| WO | WO-2006/028943 A1 | 3/2006 |
| WO | WO-2006/031602 A1 | 3/2006 |
| WO | WO-2006/034153 A2 | 3/2006 |
| WO | WO-2006/074163 A2 | 7/2006 |
| WO | WO-2006/096342 A1 | 9/2006 |
| WO | WO-2006/111801 A2 | 10/2006 |
| WO | WO-2006/134354 A1 | 12/2006 |
| WO | WO-2007/061927 A2 | 5/2007 |
| WO | WO-2007/070544 A2 | 6/2007 |
| WO | WO-2007/085373 | 8/2007 |
| WO | WO-2007/127351 A1 | 11/2007 |
| WO | WO-2007/149844 A2 | 12/2007 |
| WO | WO-2008/010197 A2 | 1/2008 |
| WO | WO-2008/100790 A2 | 8/2008 |
| WO | WO-2008/112501 A2 | 9/2008 |
| WO | WO-2008/153653 | 12/2008 |
| WO | WO-2009/064618 A1 | 5/2009 |
| WO | WO-2009/077845 A2 | 6/2009 |
| WO | WO-2009/088905 A1 | 7/2009 |
| WO | WO-2009/124288 | 10/2009 |
| WO | WO-2009/126747 | 10/2009 |
| WO | WO-2010/009019 | 1/2010 |
| WO | WO-2010/047644 | 4/2010 |
| WO | WO-2010/075565 A2 | 7/2010 |
| WO | WO-2010/085344 A1 | 7/2010 |
| WO | WO-2010/096717 A1 | 8/2010 |
| WO | WO-2010/130617 | 11/2010 |
| WO | WO-2010/135352 A1 | 11/2010 |
| WO | WO-2010/146581 | 12/2010 |
| WO | WO-2010/148246 A2 | 12/2010 |
| WO | WO-2011/011581 A2 | 1/2011 |
| WO | WO-2011/153304 | 12/2011 |
| WO | WO-2011/159913 A2 | 12/2011 |
| WO | WO-2011/163157 A2 | 12/2011 |
| WO | WO-2012/002944 A1 | 1/2012 |
| WO | WO-2012/040380 | 3/2012 |
| WO | WO-2012/067724 A1 | 5/2012 |
| WO | WO-2012/109367 | 8/2012 |
| WO | WO-2012/111137 | 8/2012 |
| WO | WO-2012/120490 A2 | 9/2012 |
| WO | WO-2012/131672 A2 | 10/2012 |
| WO | WO-2012/134761 | 10/2012 |
| WO | WO-2012/135859 A2 | 10/2012 |
| WO | WO-2012/166804 | 12/2012 |
| WO | WO-2013/055703 A1 | 4/2013 |
| WO | WO-2013/059511 A1 | 4/2013 |
| WO | WO-2013/067299 | 5/2013 |

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.
Berguer et al., Cure by Combination of Operation and Detachable Intravascular Balloon, Ann. Surg. Jul. 1982, pp. 65-68, vol. 196, No. 1.
Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.
DeSouza et al., Embolization with Detachable Balloons—Applications Outside the Head, Clinical Radiology, Apr. 21, 1992, pp. 170-175, vol. 46.
Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.
Hawkins et al., The Permeability of Detachable Latex Rubber Balloons—An In Vitro Study, Investigative Radiology, Dec. 1987, pp. 969-972, vol. 22.
Hirai et al., Emergency Balloon Embolization for Carotid Artery Rupture Secondary to Postoperative Infection, Cardiovasc Intervent Radiol, 1996, pp. 50-52, vol. 19.
Kadir et al., Therapeutic Embolization of the Kidney with Detachable Silicone Balloons, The Journal of Urology, Jan. 1983, pp. 11-13, vol. 129.
Kallmes et al., The Use of Hydrocoil for Parent Artery Occlusion, AJNR Am J Neuroradiol, Sep. 2004, pp. 1409-1410, vol. 25.
Kaufman, et al., Detachable Balloon-Modified Reducing Stent to Treat Hepatic Insufficiency After Transjugular Intrahepatic Portosystemic Shunt Creation, J Vasc Interv Radiol., May 2003, pp. 635-638, vol. 14, No. 5.
Luo, Chao-Bao et al., Endovascular Treatment of the Carotid Artery Rupture with Massive Hemorrhage, J. Chin Med Assoc., Mar. 2003.
Makita, et al., Guide-Wire-directed Detachable Balloon: Clinical Application in Treatment of Varicoceles, Radiology, 1992, pp. 575-577, vol. 183.
Marshall et al., Treatment of Traumatic Renal Arteriovenous Fistulas by Detachable Silicone Balloon Embolization, The Journal of Urology, Aug. 1979, pp. 237-239, vol. 122.
Pollak et al., Clinical Results of Transvenous Systemic Embolotherapy with a Neuroradiologic Detachable Balloon, Radiology, May 1994, pp. 477-482, vol. 191, No. 2.
Reidy et al., Transcatherer Occlusion of Coronary to Bronchial Anastomosis by Detachable Balloon Combined with Coronary Angioplasty at Same Procedure, Brit Heart J. 1983, pp. 284-287, vol. 49.
Reidy et al., Transcatheter Occlusion of a Blalock-Taussig Shunt with a Detachable Balloon in a Child, Bri Heart Journal, 1983, pp. 101-103, vol. 50.
Ross et al., The Vascular Plug: A New Device for Parent Artery Occlusion, AJNR Am J Neuroradiol, Feb. 2007, pp. 385-386, vol. 28.
Serbinenko, F.A., Balloon Catheterization and Occlusion of Major Cerebral Vessels, J. Neurosurg. Aug. 1974, pp. 125-145, vol. 41.
Tasar, et al., Intrahepatic Arterioportal Fistula and its Treatment with Detachable Balloon and Transcatheter Embolization with Coils and Microspheres, Journal of Clinical Imaging, 2005, pp. 325-330, vol. 29.
Wehman, et al., Giant Cerebral Aneurysms: Endovascular Challenges, Neurosurgery, Nov. 2006, pp. S125-S138, vol. 59, No. 5.
White, et al., Occlusion of Varicoceles with Detachable Balloons, Radiology, May 1981, pp. 327-334, vol. 139.
Serbinenko, F.A., Occlusion by Balooning of Sacular Aneurysms of the Cerebral Arteries, Vopr, Neirokhir, Jul.-Aug. 1974, pp. 8-15, vol. 4.

(56) References Cited

OTHER PUBLICATIONS

Serebinko, F.A., Balloon Occlusion of Cavernous Portion of the Carotid Artery as a Method of Treating Carotid Cavity Anastomoses, Vopr. Neirokhir, Nov.-Dec., 1971, pp. 3-9, vol. 6.
Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.
U.S. Appl. No. 14/044,794, filed Oct. 2, 2013.
U.S. Appl. No. 14/101,171, filed Dec. 9, 2013.

\* cited by examiner

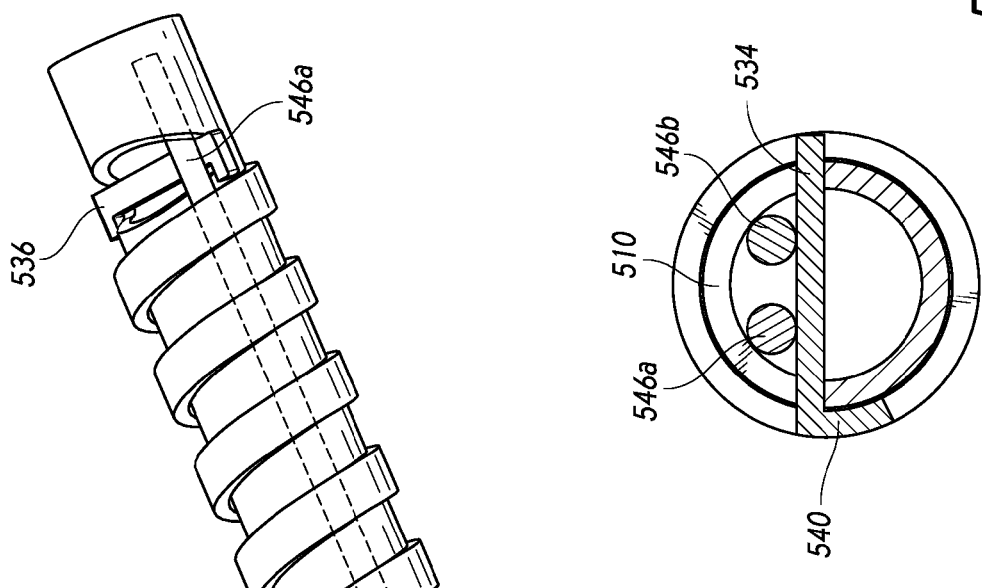
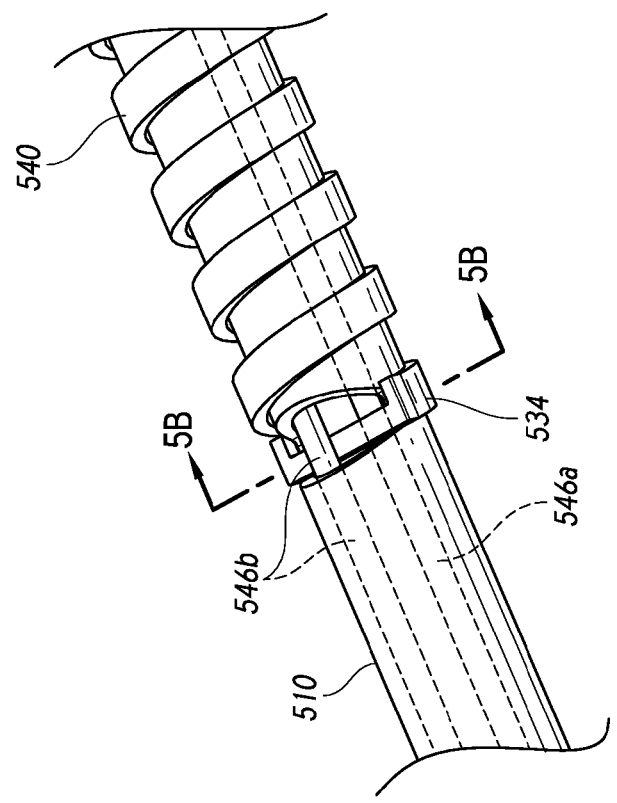
FIG. 5A
FIG. 5B

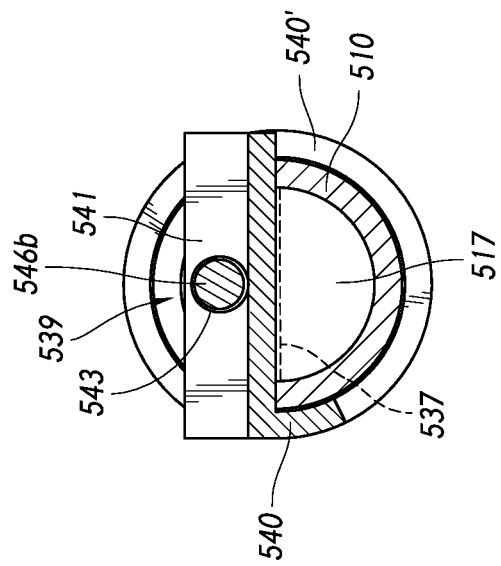
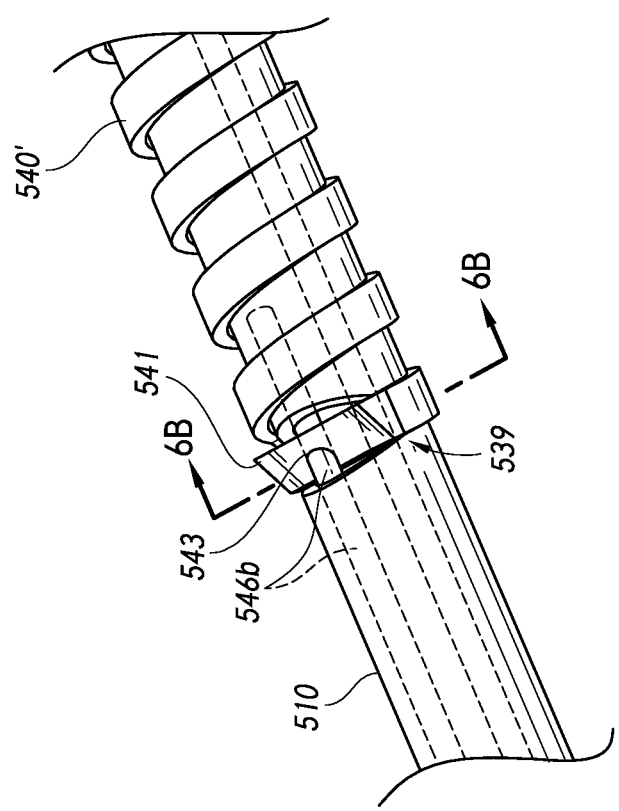

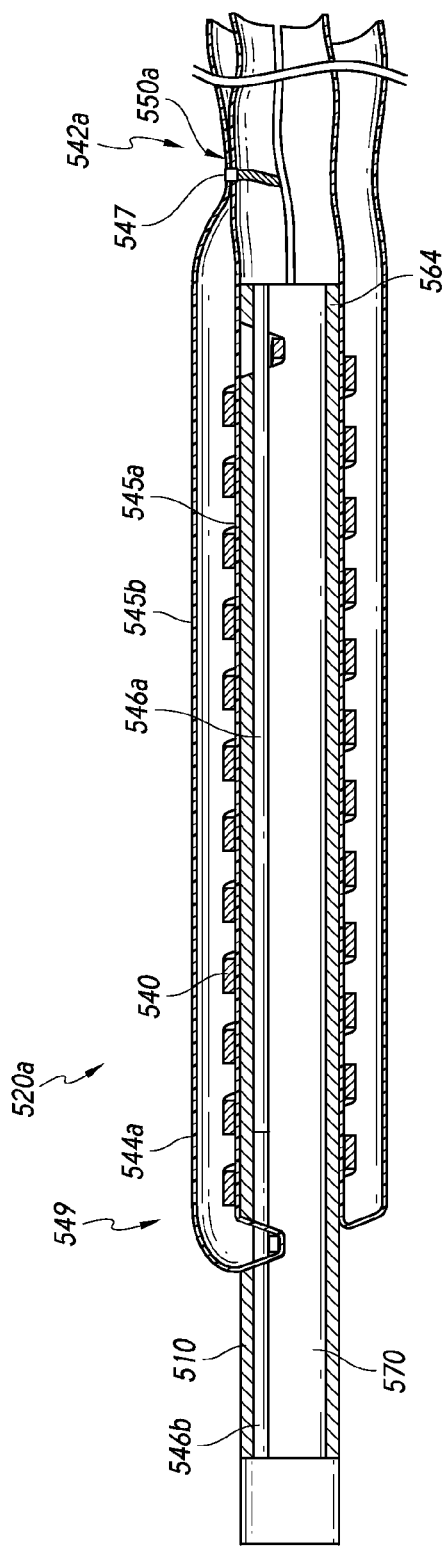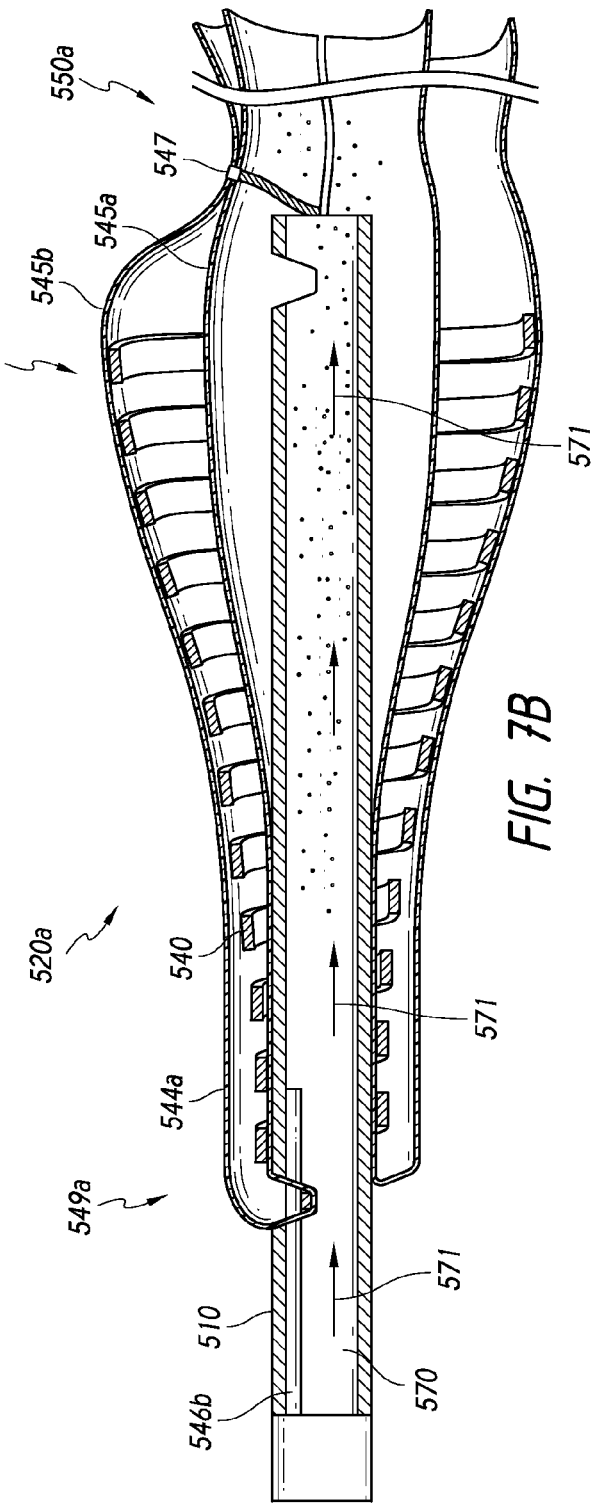

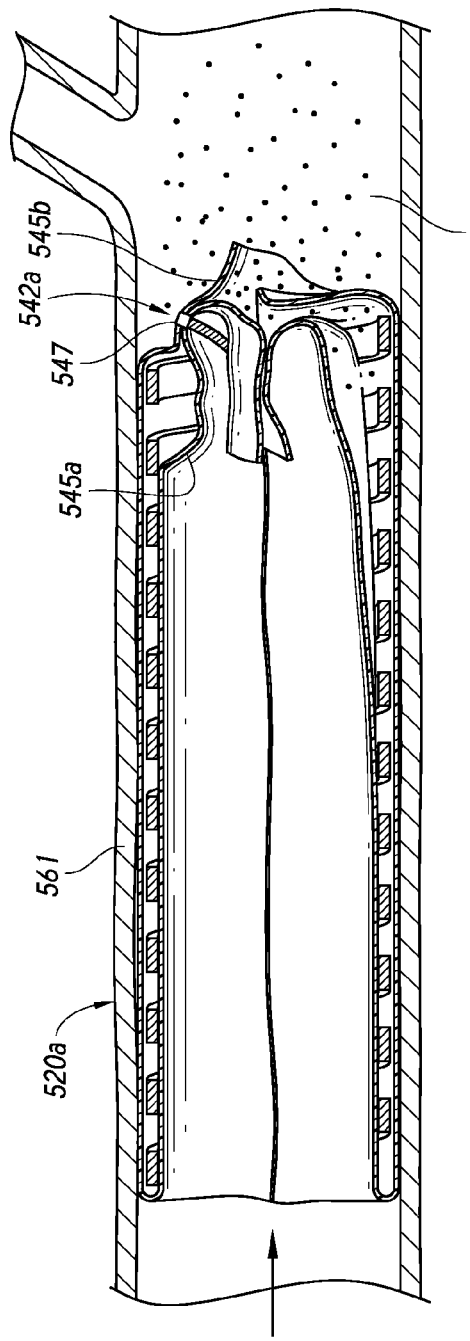
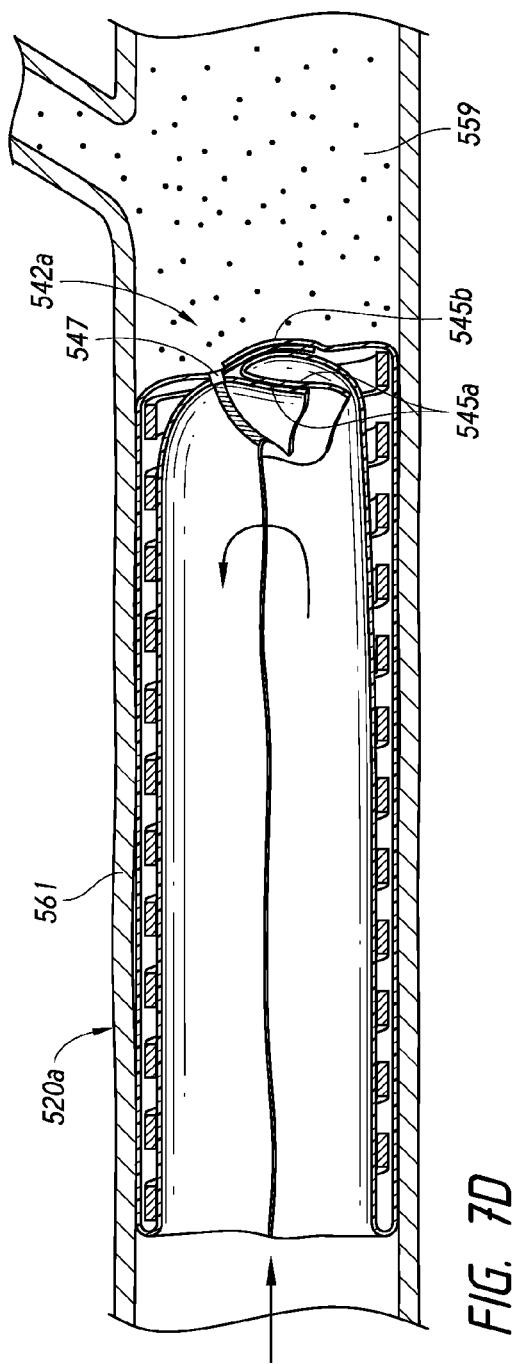
FIG. 7C
FIG. 7D

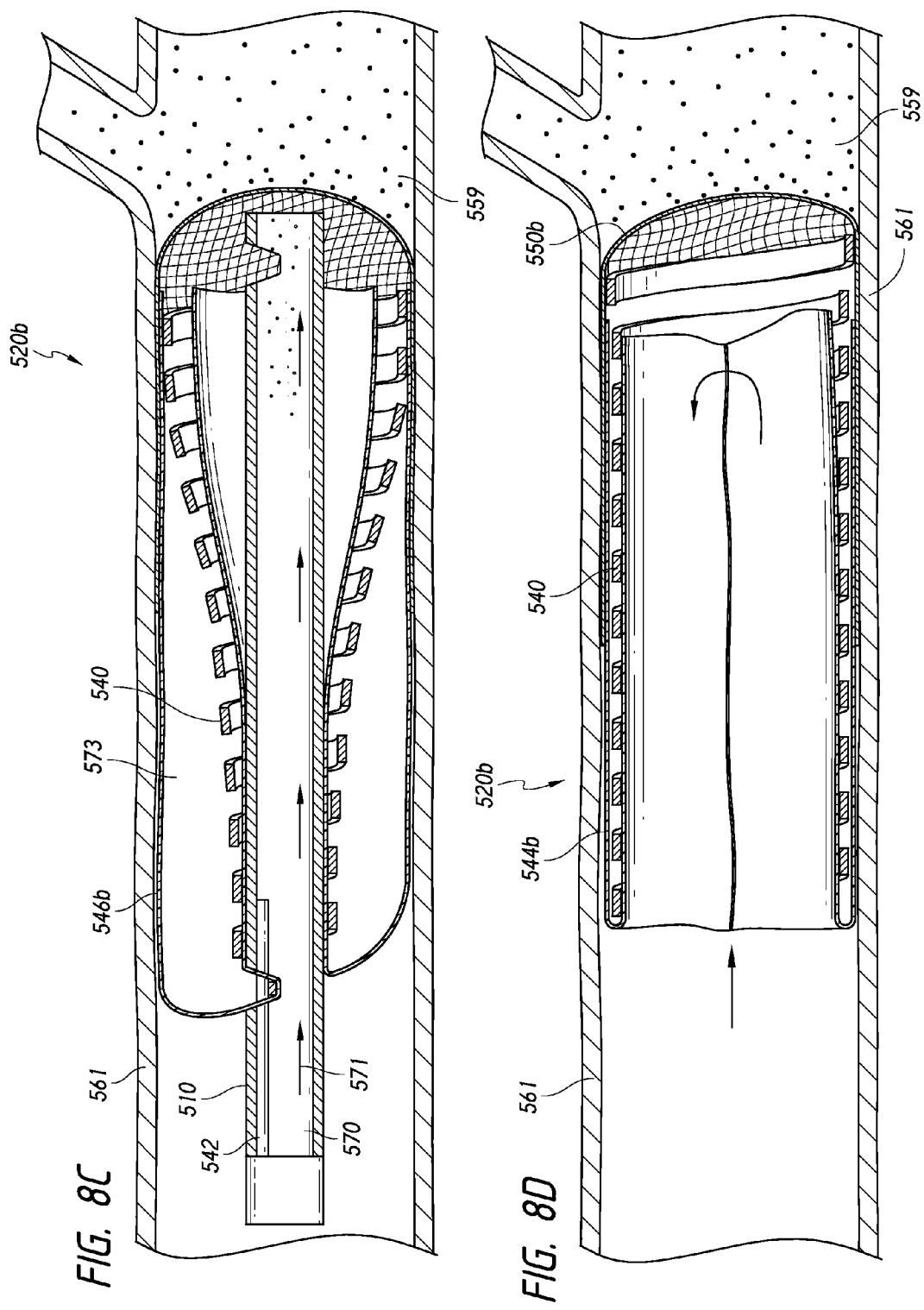

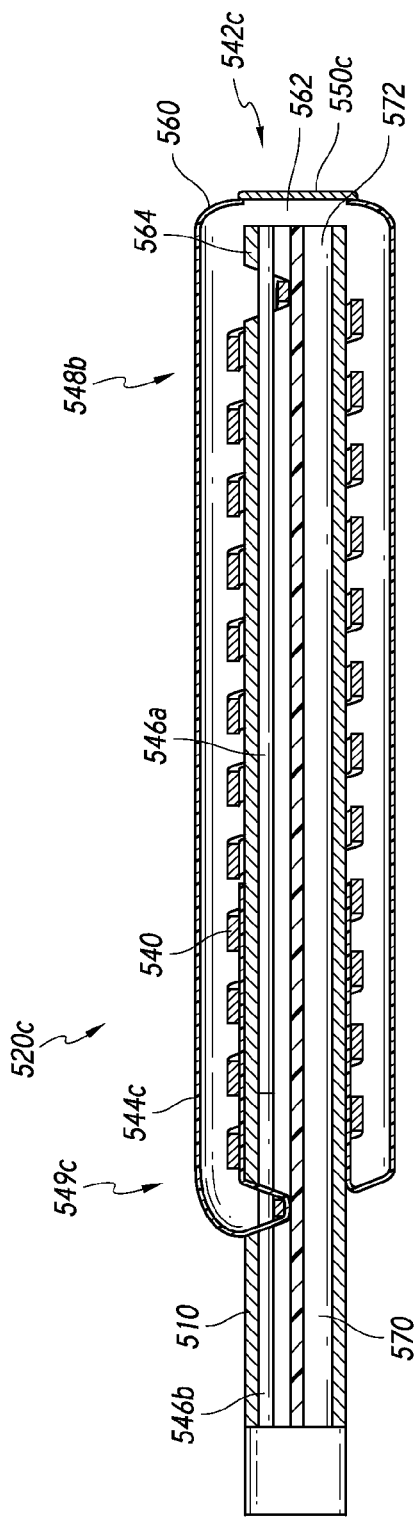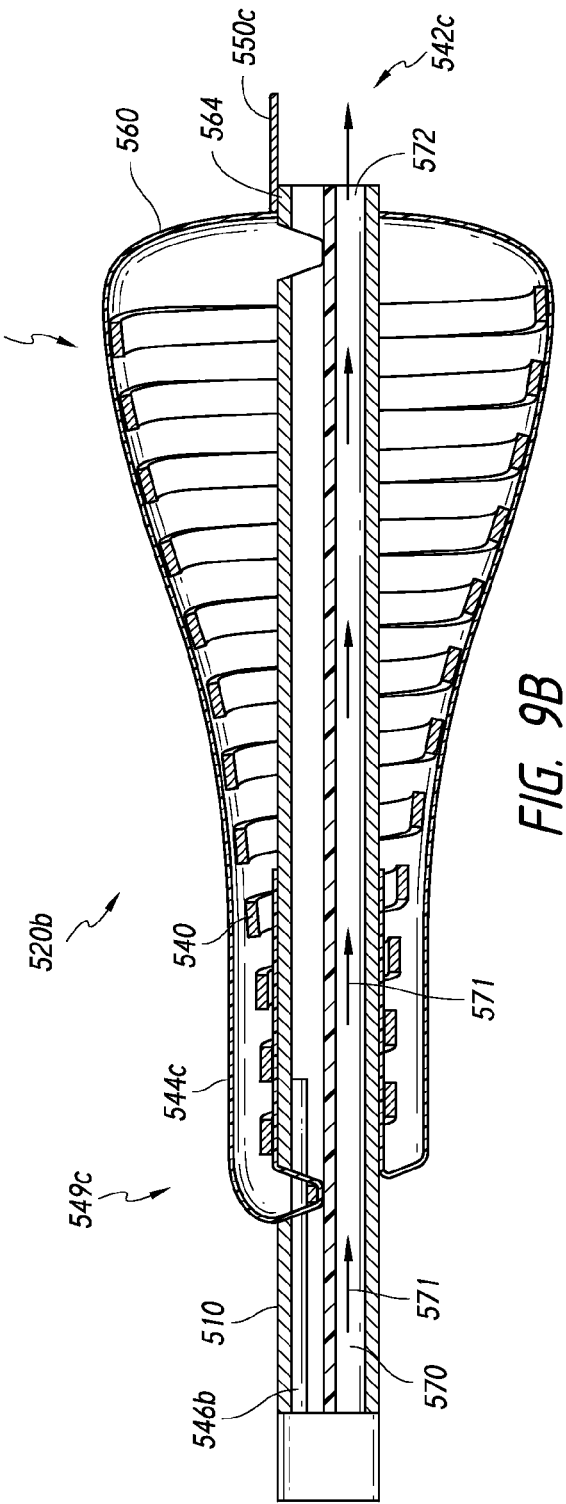

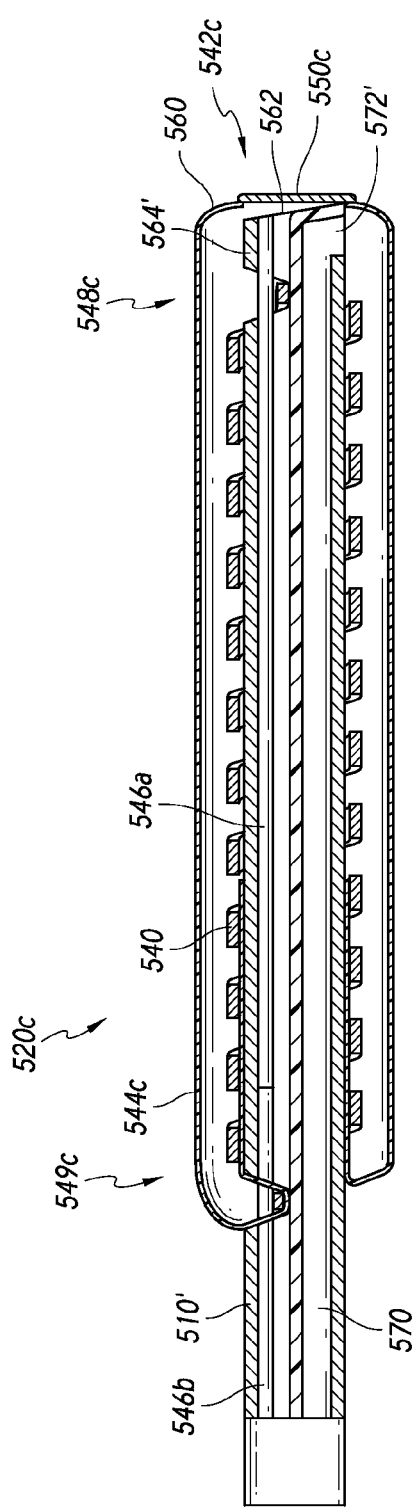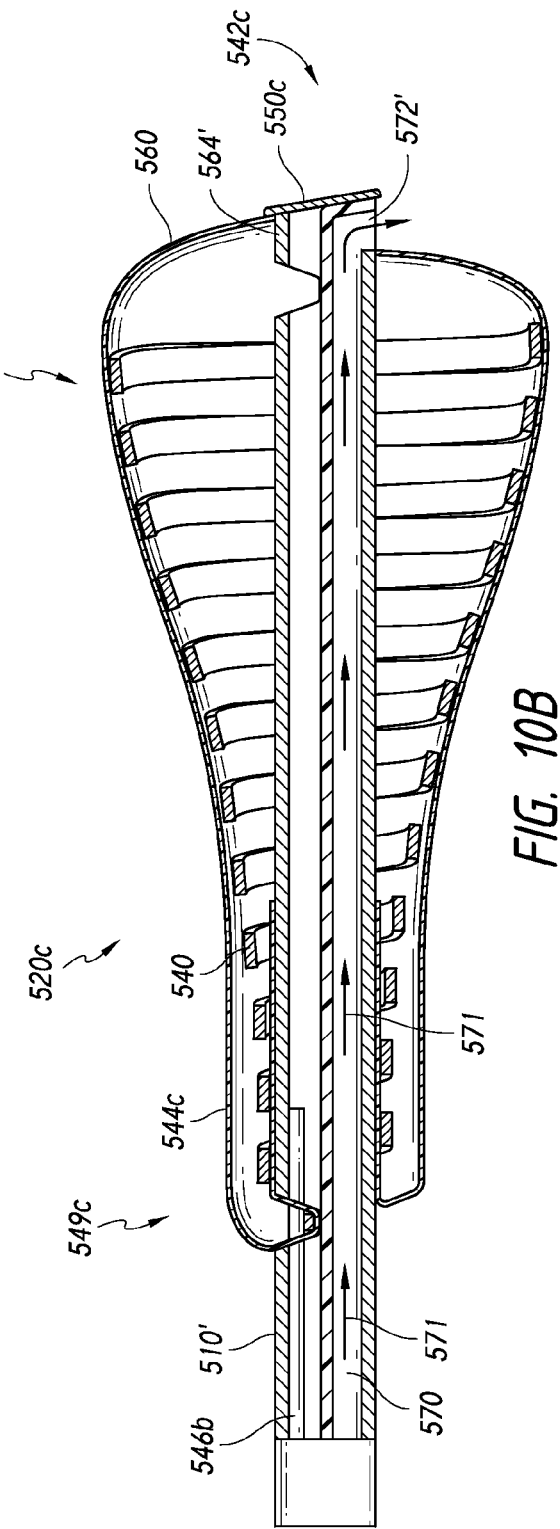

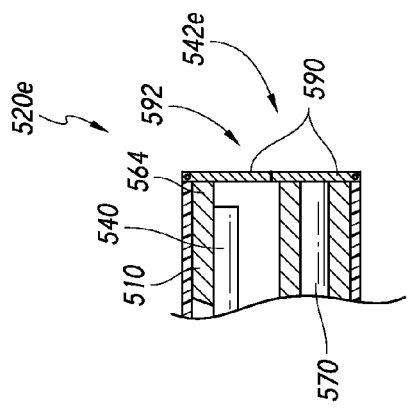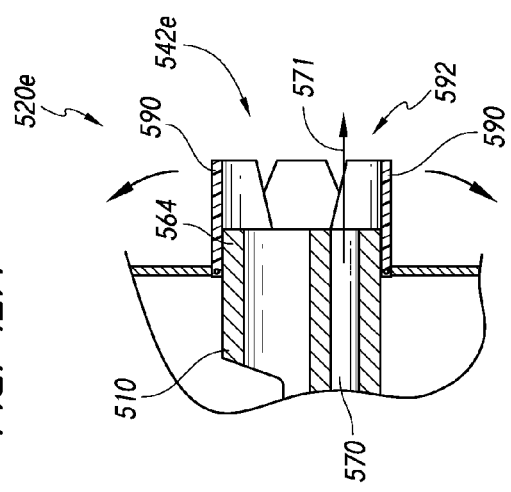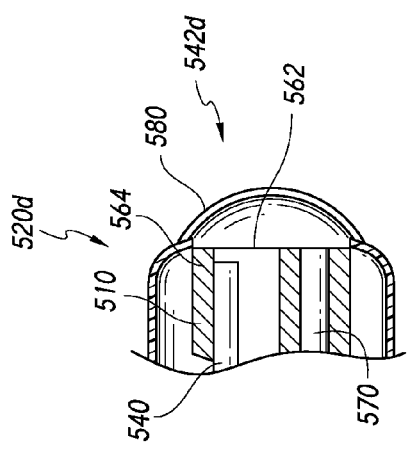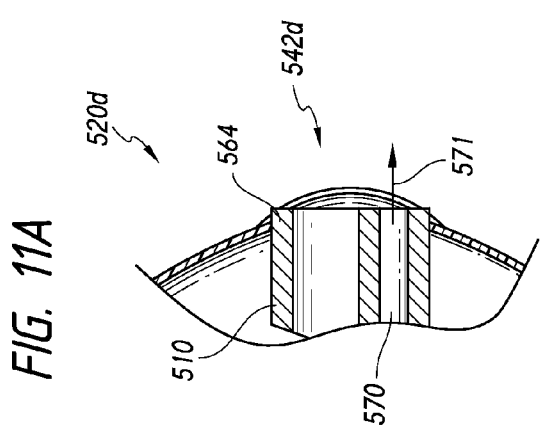

CATHETER-ASSISTED TUMOR TREATMENT

CROSS-REFERENCE TO RELATED APPLICATIONS

This application claims the priority benefit of U.S. Provisional Application Nos. 61/835,406, filed Jun. 14, 2013, 61/835,461, filed Jun. 14, 2013, and 61/900,321, filed Nov. 5, 2013, the entirety of each of which is incorporated herein by reference.

BACKGROUND

Field of the Inventions

The present disclosure is related to endovascular apparatuses and methods, and more specifically, to apparatuses and methods for delivering a material to a target region of a body lumen and regulating blood flow therethrough.

Description of the Related Art

Blood vessels can be accessed to deploy embolic agents, contrast agents, and medications to target regions of the body. Some target regions include the blood vessels themselves, as well as organs or other tissue being fed by blood vessels.

For example, through embolization, blood flow can be reduced to encourage atrophy or infarction of a target region of the body. Such target regions can include tumors, fibroids, and vascular malformations, such as arteriovenous malformations ("AVM") or arteriovenous fistulas ("AVF"). Further, embolization of blood vessels can also be achieved to slow or stop bleeding in emergency situations.

Embolic agents can be used to treat cancer. For example, embolics can be used to occlude the vasculature feeding a tumor. Drug-loaded embolics, such as drug-loaded microspheres, can be used to deliver chemotherapeutic agents and/or therapeutic agents designed to treat inflamed or diseased tissue. In addition, clinicians have administered chemotherapeutic agents in combination with embolic polyvinyl alcohol ("PVA") particles. This type of targeted therapy can localize treatment at the site of the tumor and minimize the systemic dose while maximizing the therapeutic dose delivered locally to the target lesion, reducing potential side effects and damage to healthy tissue.

SUMMARY

Various embodiments of medical methods and apparatus disclosed herein enable a clinician to provide a targeted delivery of a material, such as an embolic material, contrast agent, or drug, to a select body region. Some embodiments relate to vessel occlusion and tissue ablation or infarction by delivery of radially expandable implant frames that can be used to deliver a material to a downstream target area, such as a blood vessels or tissue. In some embodiments, the implant can be positioned to achieve immediate total occlusion of blood flow to ensure high material concentration in the target area, precise or calibrated control of delivered material, and specific targeting of certain structures and protection of others, which is especially useful for smaller target vessels and tissues. Some embodiments also provide for secondary procedures to be performed after an initial implant and material has been deployed at a target region. Furthermore, some embodiments of the present system can help close a bodily lumen or vessel rapidly and with confidence. These various advantages and benefits can provide improved health and quality of life for millions of people.

In accordance with some embodiments, various frame configurations, expected delivered and expanded dimensions, and a description of target anatomy of some embodiments are provided. Aspects of implants and delivery devices that can be utilized in combination with the implants and features disclosed herein are disclosed in applicant's co-pending U.S. patent application Ser. No. 14/044,794, filed on Oct. 2, 2013; U.S. Patent Application No. 61/904,376, filed Nov. 14, 2013, titled Implantable Luminal Devices and Methods; U.S. Patent Application No. 61/904,379, filed on Nov. 14, 2013, titled Torque Resistant Distal Catheter Tip; U.S. patent application Ser. No. 12/906,993, filed on Oct. 18, 2010; and U.S. patent application Ser. No. 13/828,974, filed on Mar. 14, 2013, U.S. Patent Application No. 61/835,406, filed on Jun. 14, 2013, and U.S. Patent Application No. 61/835,461, filed on Jun. 14, 2013, the entireties of which are incorporated herein by reference.

Some embodiments can provide vascular implantation for vessels that are from about 2 mm to about 16 mm, from about 5 mm to about 13 mm, and in some embodiments, from about 7 mm to about 11 mm. The target delivery profile can be from about 2 Fr to about 8 Fr, about 3 Fr to about 7 Fr, from about 4 Fr to about 6 Fr, or in some embodiments, about 5 Fr. Additionally, expansion of the implant can provide sufficient radial force against the inside wall of a vein. Some embodiments can comprise features or means configured to minimize backflow of blood or minimize venous insufficiency. For example, treatment applications for embodiments of the implant can include ilio-femoral venous obstruction and chronic iliac venous outflow obstruction as a result of venous disease.

Further, in some embodiments, the implant can provide enhanced control of the delivery of a material or agent. For example, in accordance with an aspect of some embodiments is the realization that the delivery and distribution of a material can depend exclusively upon distal flow patterns. Some embodiments disclosed herein can enable control of material delivery, prevent reflux of the material, and permit calibrated delivery of the material, which can often be limited by early reflux along a delivery platform. The material can comprise liquid embolic agents such as N-butyl cyanoacrylate ("NBCA"), Onyx, or other liquid agents, radioembolization particles, and microspheres, such as microspheres filled with the radioactive isotope Yttrium Y-90.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A material delivery device, comprising: an expandable support member having a lumen and an outflow end, the support member being configured to expand from a collapsed configuration to an expanded configuration for placement in a body lumen; a cover component, extending along the support member, defining an aperture; and a valve component coupled to the cover component and disposed at the outflow end, the valve component permitting outflow of a material through the aperture and restricting backflow of the material into the aperture.

Clause 2. The device of Clause 1, wherein the cover component comprises a tubular membrane coupled to the support member and the valve component comprises a free end of the tubular membrane extending away from the support member at the outflow end, the free end of the tubular membrane being configured to permit outflow of the material through the outflow end and to invert or fold onto itself to restrict backflow of the material into the outflow end.

Clause 3. The device of any one of Clauses 1 to 2, wherein the tubular membrane comprises inner and outer portions that extend along respective interior and exterior surfaces of the support member.

Clause 4. The device of Clause 3, wherein the free end of the tubular membrane extends from the outer portion, and the inner portion comprises a second free end.

Clause 5. The device of Clause 4, wherein the free end is coupled to the second free end.

Clause 6. The device of any one of Clauses 1 to 5, wherein the cover component comprises a tubular membrane coupled to the support member and the valve component comprises a free end of the tubular membrane extending away from the support member at the outflow end, wherein the tubular membrane comprises a tubular outer portion extending along a support member exterior and a segmented inner portion, comprising a plurality of strips, extending along a support member interior.

Clause 7. The device of Clause 6, wherein the free end is coupled to at least one of the plurality of strips.

Clause 8. The device of Clause 7, wherein the coupling comprises a suture.

Clause 9. The device of any one of Clauses 1 to 8, wherein the valve component is movable between open and closed positions, the valve component permitting flow of the material through the outflow end when in the open position and restricting backflow of the material through the outflow end when in the closed position.

Clause 10. The device of Clause 9, wherein in the open position, at least a portion of the valve component is spaced apart from the aperture to permit flow through the aperture.

Clause 11. The device of Clause 9, wherein in the closed position, the valve component has a sealing relationship with at least one of the support member or cover component to close the aperture at least partially and restrict flow through the device.

Clause 12. The device of any one of Clauses 1 to 11, wherein the valve component comprises a mesh material.

Clause 13. The device of Clause 12, wherein the mesh material is coupled to an outer surface of the cover component adjacent to the outflow end.

Clause 14. The device of any one of Clauses 1 to 13, wherein the valve component comprises a flap structure coupled to the cover component adjacent the outflow end, the flap structure being movable away from the aperture to permit flow therethrough.

Clause 15. The device of any one of Clauses 1 to 14, wherein the valve component comprises a plurality of deflectable panels.

Clause 16. The device of any one of Clauses 1 to 15, wherein the valve component comprises a split dome.

Clause 17. The device of any one of Clauses 1 to 16, wherein the support member comprises a helical body.

Clause 18. The device of any one of Clauses 1 to 17, wherein the support member comprises a deflectable frame configured to expand from a substantially linear collapsed configuration to the expanded configuration.

Clause 19. A method of delivering a material to a target region of a body lumen, comprising: advancing an implant to the target region, the implant having first and second sections engaged with a catheter at respective first and second engagement points; releasing the implant first section from engagement with the catheter at the first engagement point; permitting the implant first section to expand against a lumen wall at the target region such that the lumen becomes at least substantially occluded; and injecting a material through a portion of the implant.

Clause 20. The method of Clause 19, wherein the implant first section comprises an implant distal section, and wherein the releasing comprises disengaging a first engagement member from the distal section.

Clause 21. The method of Clause 20, wherein the portion of the implant comprises a valve component and the permitting comprises causing the valve component to contact a distal end of the catheter such that the catheter distal end moves the valve component to an open position.

Clause 22. The method of Clause 21, wherein the injecting comprises advancing the material out through the valve component after the valve component is in the open position.

Clause 23. The method of any one of Clauses 19 to 22, further comprising, after the material is injected into the lumen, releasing the implant second section and moving the catheter proximally relative to the implant such that the valve component moves to a closed position.

Clause 24. The method of Clause 23, wherein the moving the catheter relative to the implant comprises proximally withdrawing the catheter within the lumen.

Clause 25. The method of any one of Clauses 19 to 24, wherein the implant first section comprises a proximal section, and wherein the releasing comprises disengaging a first engagement member from the proximal section.

Clause 26. The method of Clause 25, wherein the permitting further comprises flushing the implant with a fluid to facilitate expansion of the proximal section.

Clause 27. The method of any one of Clauses 19 to 26, further comprising releasing the implant second section into apposition with the lumen wall such that the implant is disengaged from the catheter.

Clause 28. The method of any one of Clauses 19 to 27, further comprising proximally withdrawing the assembly from the lumen.

Clause 29. The method of Clause 28, wherein the withdrawing comprises withdrawing the assembly into a guide catheter such that expanded first section collapses within the guide catheter.

Clause 30. The method of any one of Clauses 19 to 29, further comprising, prior to releasing the implant first section, releasing a blocking implant into contact against the lumen wall downstream of the target region, the blocking implant occluding flow through the lumen beyond the target region.

Clause 31. The method of Clause 30, further comprising, after injecting a material, allowing the material to flow into the target region, and removing the blocking implant from the lumen.

Clause 32. A method of delivering a material to a target region of a body lumen, comprising:

removing an occlusion at a distal end of an implant, deployed within the lumen upstream of the target region, thereby restoring flow through the lumen to the target region; and after removing the occlusion from the implant, injecting a material into the lumen such that the material passes through the implant to the target region.

Clause 33. The method of Clause 32, wherein contacting the implant comprises advancing an adjustment member through the implant to pierce a cover component of the implant.

Clause 34. The method of Clause 33, wherein the adjustment member comprises a catheter and the advancing comprises advancing the catheter through the implant to pierce a cover component of the implant.

Clause 35. The method of any one of Clauses 32 to 34, wherein the implant is a first implant, and the method further comprises: after contacting the first implant, advancing a second implant to the target region, the second implant having first and second sections engaged with a catheter at respective first and second engagement points; releasing the first section from engagement with the catheter at the first engagement point; and before injecting a material, permitting the implant first section to expand against a lumen wall at the target region such that the lumen becomes at least substantially occluded.

Clause 36. The method of Clause 35, further comprising releasing the second implant adjacent to the first implant.

Clause 37. The method of Clause 35, further comprising releasing the second implant within the first implant.

Clause 38. The method of any one of Clauses 32 to 37, wherein contacting the first implant comprises contacting a mesh component of the first implant with a material to dissolve coagulated material on the mesh component, thereby restoring flow through the mesh component.

Clause 39. A delivery assembly, for delivering an expandable member to a body lumen or luminal structure of a patient, comprising: a carrier member, positionable in a luminal structure of a patient, comprising a lumen having a cross-sectional area comprising a first portion and a second portion that are separated by a line segment intersecting a circumference of the carrier member, the carrier member comprising a slot extending through the carrier member into the lumen and bounded by the line segment and the circumference, within the first portion; an elongate member extending through the carrier lumen and across the slot; and an expandable member configured to expand within and engage the luminal structure, the expandable member comprising a coupling portion that fits within the slot, the coupling portion comprising an aperture configured to receive the elongate member therethrough when the coupling portion is positioned within the slot; wherein the elongate member is configured to move axially through the carrier lumen to be removed from the aperture and permit release of the coupling portion from the slot.

Clause 40. The assembly of Clause 39, wherein the carrier lumen extends to and is open at a distal end of the carrier member.

Clause 41. The assembly of any one of Clauses 39 to 40, wherein the carrier member comprises a second slot, distal to the slot, configured to receive a distal coupling portion of the expandable member.

Clause 42. The assembly of Clause 41, wherein the distal coupling portion comprises an aperture configured to receive an elongate member therethrough when the distal coupling portion is positioned within the second slot.

Clause 43. The assembly of any one of Clauses 39 to 42, wherein the elongate member is configured to be refracted by an operator such that the elongate member permits the release of the first portion.

Clause 44. The assembly of any one of Clauses 39 to 43, wherein the slot comprises a slot depth of between about ⅓ and about ⅔ of a carrier member diameter.

Clause 45. The assembly of any one of Clauses 39 to 44, wherein the slot comprises a slot depth of about ½ of a carrier member diameter.

Clause 46. The assembly of any one of Clauses 39 to 45, further comprising a cover member extending at least partially over the expandable member.

Clause 47. The assembly of any one of Clauses 39 to 46, wherein the slot comprises distal and proximal faces that extend in substantially parallel planes, the slot defining a slot width between the distal and proximal faces.

Clause 48. The assembly of Clause 47, wherein the distal and proximal faces extend substantially perpendicularly relative to a longitudinal axis of the carrier member.

Clause 49. The assembly of Clause 47, wherein the distal and proximal faces are obliquely oriented relative to a longitudinal axis of the carrier member.

Clause 50. The assembly of any one of Clauses 39 to 49, wherein the coupling portion comprises a flat cross-sectional shape.

Clause 51. The assembly of any one of Clauses 39 to 50, wherein the slot width is less than twice a thickness of the coupling portion.

Clause 52. An expandable implant, for placement in a body lumen or luminal structure of a patient via a carrier member, comprising: an expandable member configured to expand within and engage the body lumen, the expandable member comprising proximal and distal end portions, the proximal end portion comprising an aperture configured to receive an elongate member therethrough for coupling the proximal end portion relative to a carrier member for delivery to the body lumen; and a cover member extending at least partially over the proximal and distal end portions, the cover member comprising an open end for permitting fluid flow therethrough.

Clause 53. The implant of Clause 52, wherein the expandable member comprises a coil.

Clause 54. The implant of any one of Clauses 52 to 53, wherein the expandable member comprises a flat coil.

Clause 55. The implant of any one of Clauses 52 to 54, wherein the expandable member comprises a flat coil and the aperture extends radially through the proximal end portion of the flat coil.

Clause 56. The implant of Clause 55, wherein the proximal end portion comprises a substantially planar portion, the aperture extending through a center of the proximal end portion.

Clause 57. The implant of any one of Clauses 52 to 56, wherein the proximal end portion defines an average width that is approximately equal to an average width of the expandable member between the proximal and distal end portions.

Clause 58. The implant of any one of Clauses 52 to 57, wherein the distal end portion comprises a second aperture configured to receive an elongate member therethrough for coupling the distal end portion relative to the carrier member for delivery to the body lumen.

Clause 59. The implant of Clause 58, wherein the distal end portion comprises a substantially planar portion, the second aperture extending through a center of the distal end portion.

Clause 60. A method of delivering an expandable member to a luminal structure of a patient, comprising: advancing a carrier member through a luminal structure of a patient to a target area, the carrier member being coupled to an expandable member via an elongate member, the elongate member extending through a lumen of the carrier member to engage an end portion of the expandable member within a slot of the carrier member; proximally retracting the elongate member from an aperture of the end portion to release the end portion; and permitting release of the expandable member against the luminal structure.

Clause 61. The method of Clause 60, further comprising proximally retracting an elongate member from a second aperture of a second end portion of the expandable member.

Clause 62. The method of any one of Clauses 60 to 61, wherein the proximally retracting comprises proximally retracting a second elongate member from a second aperture of a second end portion of the expandable member.

Clause 63. The method of any one of Clauses 60 to 62, performed in combination with the method of any one of Clauses 19 to 38.

Clause 64. The method of any one of Clauses 60 to 63, performed using the implant of any one of Clauses 1 to 18 or Clauses 52 to 59.

Clause 65. The method of any one of Clauses 59 to 63, performed using the assembly of any one of Clauses 39 to 51.

Clause 66. A method of manufacturing an expandable member for delivery into a luminal structure of a patient via a carrier member, comprising: positioning an expandable member onto a carrier member; placing an end portion of the expandable member into a slot of the carrier member; and inserting an elongate member into an aperture of the end portion to engage the end portion within the slot.

Clause 67. The method of Clause 66, wherein the end portion comprises a flat cross-sectional shape, and the placing the end portion comprises twisting the end portion such that the flat shape is aligned with the slot, in a side, cross-sectional view.

Clause 68. The method of Clause 67, wherein the slot comprises distal and proximal faces extending in a substantially parallel planes.

Clause 69. The method of Clause 68, wherein the substantially parallel planes are oriented substantially perpendicular relative to a longitudinal axis of the carrier member.

Clause 70. The method of Clause 68, wherein the substantially parallel planes are obliquely oriented relative to a longitudinal axis of the carrier member.

Clause 71. The method of any one of Clauses 66 to 70, further comprising: placing a second end portion of the expandable member into a second slot of the carrier member; and inserting a second elongate member into a second aperture of the second end portion to engage the second end portion within the slot.

Clause 72. The method of any one of Clauses 66 to 71, performed using the implant of any one of Clauses 1 to 18 or Clauses 52 to 59.

Clause 73. The method of any one of Clauses 66 to 72, performed using the assembly of any one of Clauses 39 to 51.

Clause 74. The implants, assemblies, or methods of any of the preceding Clauses, wherein a slot width, slot depth, catheter lumen inner diameter, catheter lumen inner diameter, engagement component diameter, aperture diameter, proximal end portion width, or proximal end portion thickness is within any of the corresponding ranges disclosed herein.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 5A is a perspective view of a support frame mounted on a catheter, according to some embodiments.

FIG. 5B is an end view of the catheter and support frame of FIG. 5A, according to some embodiments.

FIG. 6A is a perspective view of a support frame mounted on a catheter, according to some embodiments.

FIG. 6B is an end view of the catheter and support frame of FIG. 6A, according to some embodiments.

FIGS. 7A-7B are side, cross-sectional views of positions of an implant assembly having a valve component, according to some embodiments.

FIGS. 7C-7D are side, cross-sectional views of the implant assembly of FIGS. 6A-6B subsequent to deployment and illustrating the closure thereof, according to some embodiments.

FIGS. 8A-8D are side, cross-sectional views of positions of an implant assembly having a mesh-type valve component, according to some embodiments.

FIGS. 9A-9B are side, cross-sectional views of positions of an implant assembly having a valve component, according to some embodiments.

FIGS. 10A-10B are side, cross-sectional views of positions of an implant assembly having a valve component, according to some embodiments.

FIGS. 11A-11B are side, cross-sectional views of positions of an implant assembly having a valve component, according to some embodiments.

FIGS. 12A-12B are side, cross-sectional views of positions of an implant assembly having a valve component, according to some embodiments.

DETAILED DESCRIPTION

Figure 1:
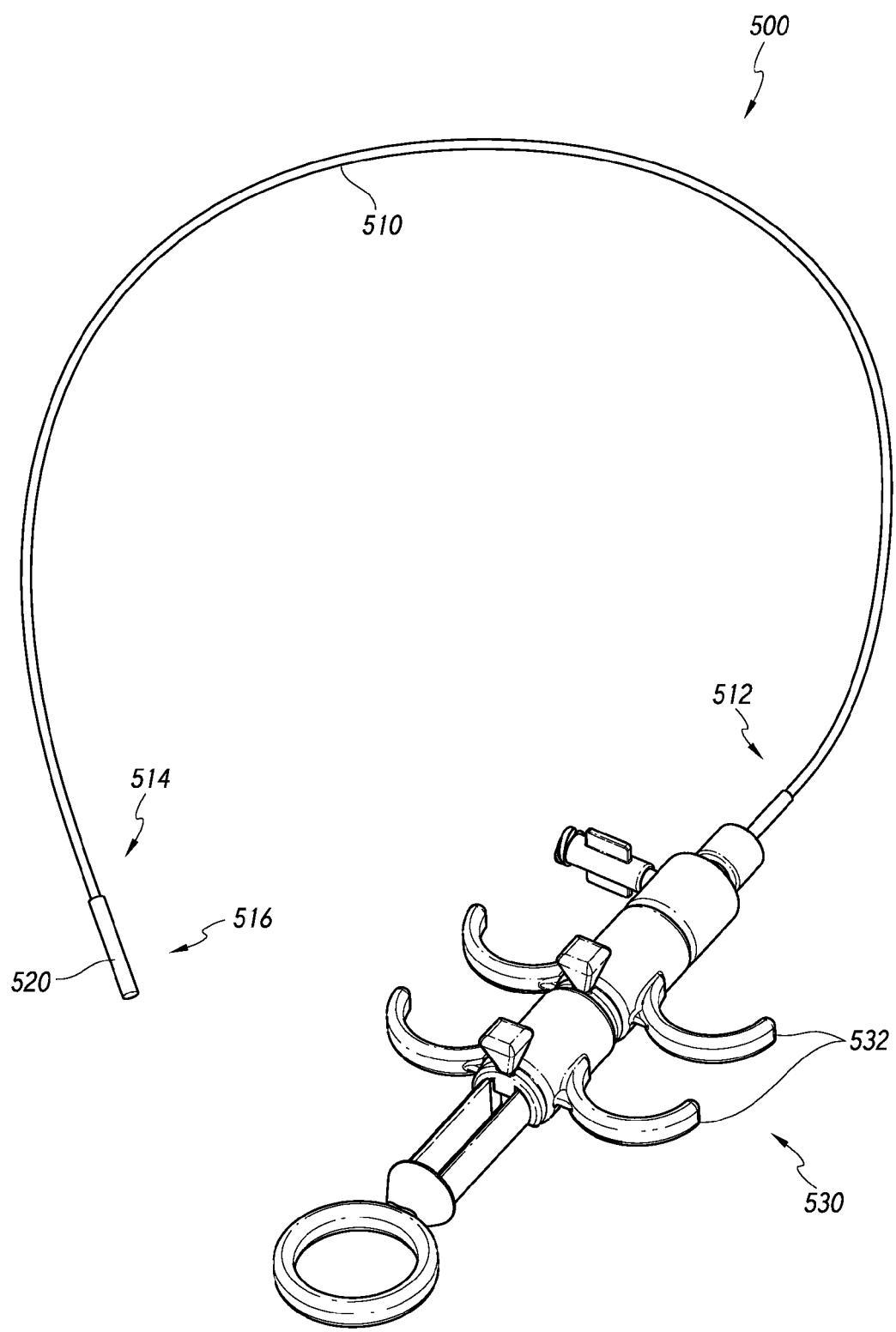
FIG. 1 is a perspective view of an implant carrier assembly, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

Some embodiments of the procedure, technique, and implant disclosed herein can enable a clinician, in one or a several clinical procedures, to occlude, dynamically control the flow through, or deploy a material through an implant. For example, according to some embodiments disclosed herein, procedures, techniques, and implants are provided by which an implant can be deployed into a body lumen in order to provide targeted delivery of a material, such as an embolic material, contrast agent, or drug. It shall be noted that even though some of the embodiments disclosed herein may refer to the use of an embolic material, such embodiments can employ one or more materials, such as embolic materials, contrast agents, or drugs, including those disclosed herein and other acceptable materials.

Additionally, in some embodiments, methods and implants are provided in which a clinician can deposit embolic material into a target area downstream of an implanted shunt while preventing upstream flow or backflow of the particles away from the target area.

In some embodiments, an implant can be expanded into apposition with a luminal wall to at least partially occlude flow through the lumen, and embolic material can be released through an aperture or valve component of the implant, thereby isolating the flow of embolic material into the target region. The valve component can comprise a one-way valve. Such procedures, techniques, and implants can be used to induce infarction of tumors, arteries, or other target body regions.

Further, in accordance with some embodiments, a clinician can place one or more implants into the vasculature and use of an implant to facilitate the delivery of a material, such as an embolic material, to a target region within the body.

For example, a clinician can advance an implant to a location upstream of specific arteries and/or a target structure fed by the arteries. At least a portion of the implant can be expanded into apposition with the vessel wall, thereby reducing and/or eliminating any anterograde blood flow past the implant. Thereafter, a material can be passed through a valve component or aperture of the implant in order to pass the material toward the target region. Such embodiments advantageously enhance or increase the concentration of material delivered to the arteries and target structure. Further, in some embodiments, a distal implant can be released at a location immediately distal to the target region such that the distal implant prevents or mitigates any downstream migration of the material toward a downstream section of the vessel.

Some embodiments of the flow regulating implant can comprise a generally tubular member. In some embodiments, the tubular member can further comprise a graft, cover, or other material attached to a frame. Some implants that can be used in some embodiments are disclosed in applicant's co-pending U.S. patent application Ser. No. 12/906,933, filed on Oct. 18, 2010, Ser. No. 13/828,974, filed on Mar. 14, 2013, and 61/835,406, filed on Jun. 14, 2013, titled "Implantable Luminal Devices and Methods," the entireties of which are incorporated herein by reference.

Figure 2:
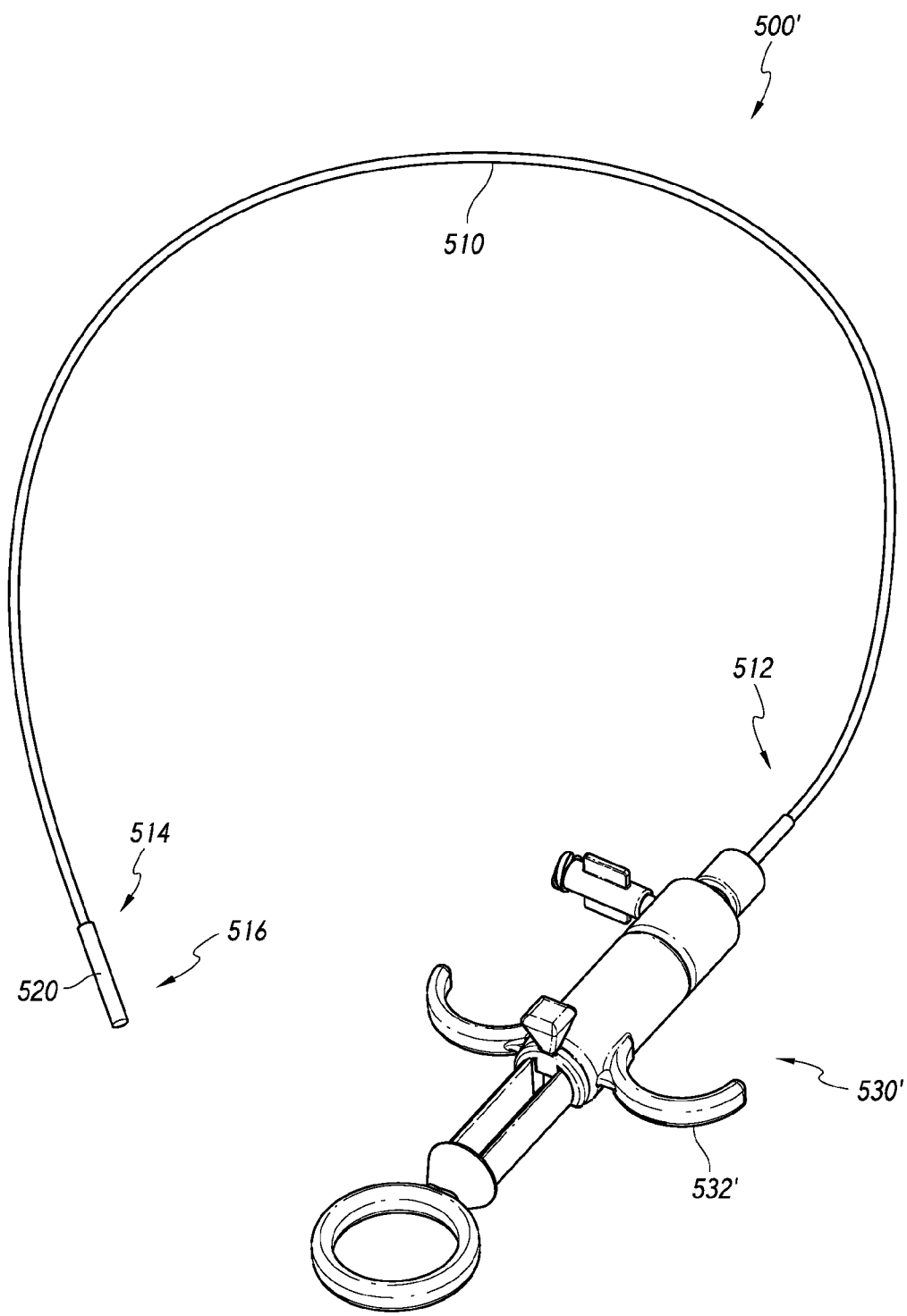
FIG. 2 illustrates a perspective view of another implant carrier assembly, according to some embodiments.

FIGS. 1 and 2 illustrate embodiments of an implant carrier assembly. As shown in FIGS. 1 and 2, the implant carrier assembly 500, 500' can comprise a catheter 510 having a lumen that extends between a proximal portion 512 and a distal portion 514 of the catheter. The catheter 510 can also comprise an engagement section 516, which can be located along a distal portion of the catheter 510, configured to engage and/or restrain an implant positioned therealong. Thus, the implant can be supported, engaged, or restrained along an exterior surface of the catheter. The catheter 510 can define a length from about 50 cm to about 200 cm, from about 70 cm to about 160 cm, or in some embodiments, about 120 cm, with a working length of from about 85 cm to about 140 cm, from about 95 cm to about 130 cm. In accordance with some embodiments, the total length of the implant carrier assembly (with handle) can be about 117 cm, with a working length of 97 cm.

The catheter 510 can be configured to move within a guide sheath when advancing the assembly 500, 500' into a patient for treatment. The proximal portion 512 of the catheter 510 can be configured to be relatively stiff in order to enhance the pushability of the catheter 510 through the guide sheath. Further, the distal portion 514 can be relatively flexible in order to improve the maneuverability and trackability of the catheter 510 as it is advanced through the guide sheath.

The assembly 500, 500' can also comprise an implant or device 520 loaded on the engagement section 516. The implant 520 can be supported on the engagement section 516 of the catheter 510. Further, the assembly 500, 500' can also comprise a deployment handle assembly 530, 530' attached to the catheter proximal portion 512. The deployment handle 530 shown in FIG. 1 includes two pull members 532, whereas the deployment handle 530' shown in FIG. 1 includes a single pull member 532'. As discussed further herein and in co-pending U.S. patent application Ser. No. 14/044,794, filed Oct. 2, 2013, the entirety of which is incorporated herein by reference, the pull members 532, 532' can be used to release the implant 520 from engagement with the engagement section 516 of the catheter 510. In some embodiments, both deployment handles 530, 530' can be used to release distal and proximal portions of the implant 520. However, the deployment handle 530 can be configured to provide dedicated pull members 532 for releasing each of the distal and proximal portions of the implant 520. In contrast, the deployment handle 530' can be configured to provide a single pull member 532' that can be, for example, moved a first distance to release the distal portion of the implant 520 and pulled a second distance to release the proximal portion of the implant 520. Either embodiment can be used in performing the methods and procedures disclosed herein.

Other features and characteristics of the assembly 500, 500' can be provided such as those disclosed in co-pending U.S. patent application Ser. No. 14/044,794, filed Oct. 2, 2013, the entirety of which is incorporated herein by reference.

Figure 3:
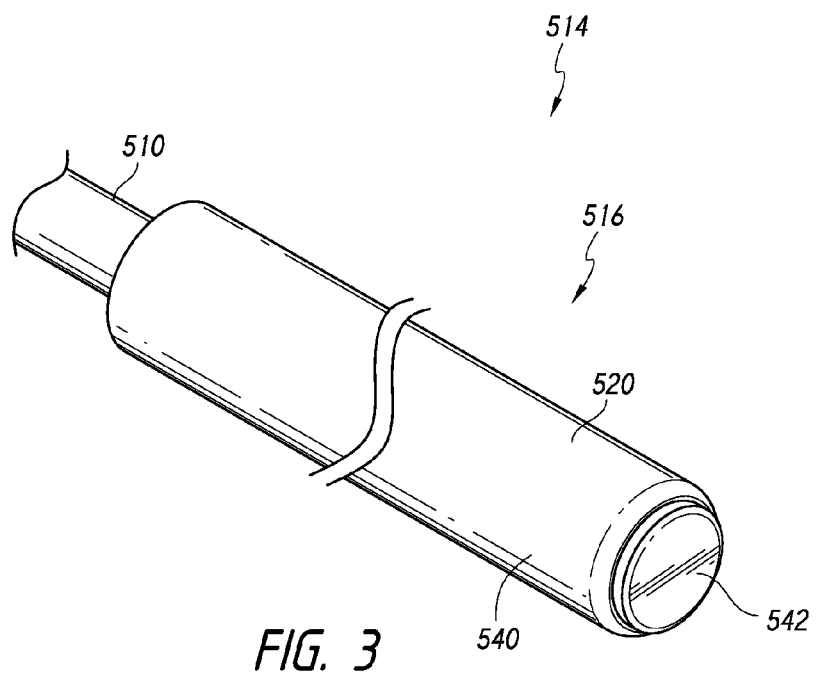
FIG. 3 is a perspective view of an implant having a valve component, according to some embodiments.
Figure 4:
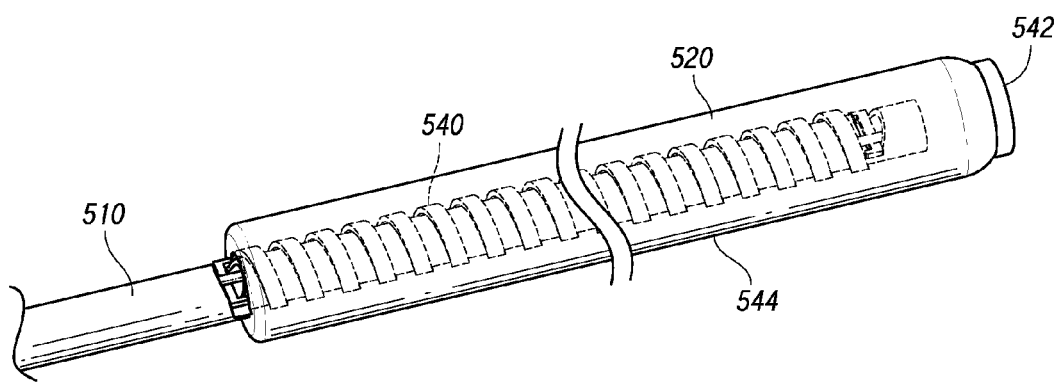
FIG. 4 is a perspective view of the implant of FIG. 3, illustrating a support component thereof, according to some embodiments.

As shown in FIGS. 3-4, the implant 520 can be supported on the engagement section 516 of the catheter 510. The implant 520 can comprise one or more apertures or valve components that can be actuated to permit flow of a material, such as an embolic material, contrast agent, or drug, through the implant 520. The implant 520 can comprise a plurality of components, such as one or more support components 540, a valve component 542, and/or a cover member 544. The cover member 544 can comprise an aperture through which a material can be passed. In embodiments using a valve component 542, the valve component 542 can be coupled to the support component 540 and/or cover member 544 and can permit flow of a material therethrough.

FIGS. 5A-5B illustrate aspects of an engagement system between the catheter 510, the support component 540, and at least one engagement component 546a, 546b. As noted above, when using a single pull member 532', a single engagement component 546 can be used to engage and release proximal and distal portions 534, 536 of the support component 540. Further, when using to pull members 532, two engagement components 546a, 546b can be used to engage and release the proximal and distal portions 534, 536 of the support component 540. Various aspects of such embodiments are disclosed in co-pending U.S. patent application Ser. No. 14/044,794, filed Oct. 2, 2013, the entirety of which is incorporated herein by reference. Thus, the implant 520 can be delivered using various embodiments of the carrier assembly 500, 500'.

In accordance with some embodiments, the engagement system can be configured such that the support component comprises one or more apertures that extend through one or more portions thereof to facilitate engagement with at least one engagement component when the support component is coupled to the catheter. For example, the engagement component can extend through the lumen of the catheter adjacent an aperture, notch, or slot of the catheter and pass through an aperture of a distal end portion of the support component in order to engage the distal end portion and secure the distal end portion relative to the aperture, notch, or slot of the catheter. The aperture can extend through the support component at an end portion or other location between the end portions, such as a midportion thereof.

Further, the support component can be coupled to the catheter with the engaged portion of the support component extending through the aperture, notch, or slot of the catheter. Advantageously, the engagement between the support component and the engagement component within the catheter lumen can reduce the profile of the carrier assembly, thereby permitting the assembly to be compatible with small gauge catheters, such as sizes between about 3 Fr and about 8 Fr, about 4 Fr and about 7 Fr, or about 5 Fr and about 6 Fr. However, in some embodiments, the engagement component can extend radially external to or outwardly from the catheter lumen to engage the portion of the support component outside of the catheter lumen and still provide compatibility with small gauge catheters.

In accordance with some embodiments, the implant carrier assembly can be configured to comprise at least one engagement member that extends at least partially through the catheter lumen. The engagement member can engage at least a portion of, and in some embodiments, one or both the proximal and distal sections of the support component. The engagement member can comprise a wire. However, in some embodiments, the engagement member can comprise a plug or other structure that can interact with one or both of the proximal or distal sections of the support component.

In some embodiments, the engagement member can be actuatable or controllable using a handle assembly, as discussed further below.

For example, an engagement section of the catheter can be configured to facilitate engagement between the support component and the engagement member extending from the handle assembly. In some embodiments, the engagement member can be selectively actuated or withdrawn in order to release engagement between the support component and the engagement member. The movement of the engagement member can be configured to be a proximal withdrawal of the engagement member. However, the engagement member can also be configured such that disengagement occurs when the engagement member is distally advanced (such as when a proximally oriented hook or segment of the engagement member engages with the support component). Indeed, the engagement member can be moved a first distance (whether proximally or distally) in order to release or disengage with one of the proximal or distal sections of the support component. Further, the engagement member can be moved a second distance, greater than the first distance (whether proximally or distally) in order to release or disengage with the other one of the proximal or distal sections of the support component.

Further, in some embodiments, the engagement section of the catheter can facilitate engagement between the implant and two or more engagement members extending from the handle assembly. Although the engagement member is illustrated as extending between the proximal and distal sections of the support component, the engagement member can engage one of the proximal or distal sections while a second engagement member can be used to engage the other of the proximal or distal sections.

For example, the catheter can comprise an engagement section and a lumen. The assembly can comprise an implant or support component supported on the engagement section. Further, the assembly can comprise a first engagement member and a second engagement member 546a, 546b configured to engage with the support component, as shown in FIG. 5B. As shown in FIG. 5A, a distal portion of the engagement member 546b can engage a proximal portion of support component and a distal portion of the engagement member 546a can engage with a distal portion of the support component.

Accordingly, in embodiments that comprise two engagement members, the engagement members can be actuated independently of each other in order to control the release of the respective proximal or distal sections of the support component or implant.

Additionally, some embodiments can be configured such that an engagement member extends through the catheter lumen and between at least one of the proximal or distal sections of the support component and the wall of the catheter. For example, the engagement member can be disposed radially between the proximal or distal section of the support component and the wall of the catheter.

For example, FIG. 5B illustrates the configuration of the catheter and the aperture, notch, or slot in relation to the engagement member and the proximal section of the support component. As shown, the proximal section can sit within the aperture and provide enough clearance between the proximal section and wall or the inner surface of the wall such that the engagement member can be positioned intermediate the wall and the proximal section. As also shown, the proximal section can extend across the entire diameter of the lumen in a transverse direction. However, the proximal and/or distal sections can also be configured to extend across the lumen less than a diameter of the lumen (whether in the transverse direction or in a radial direction).

Accordingly, the engagement member can secure the proximal section within the aperture to prevent movement of the proximal section in an axial direction (shown in FIG. 5A) and/or a radial direction (shown in FIG. 5B). In some embodiments, the support component can be a resilient or self-expanding support component, such that the proximal section will tend to expand or move out of the aperture without the presence of the engagement member. Thus, when the engagement member is in place between the proximal section and the wall of the catheter, the proximal section can be retained or engaged within the aperture. However, when the engagement member is removed from between the catheter and the proximal section of the support component, the proximal section of the support component will no longer be constrained and can therefore expand out of the aperture, notch, or slot.

The engagement between the proximal section, the engagement member, and the aperture can also be present at the distal end of the support component, although it will not be discussed further herein. However, as noted, some embodiments can be implemented in which a single end of the support component is retained within an aperture or otherwise engaged by the engagement member.

Figure 6E:
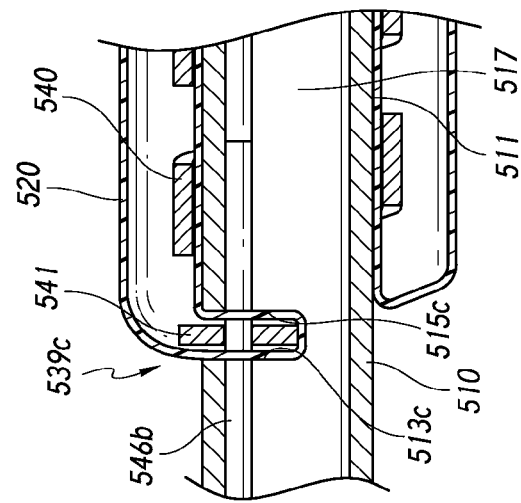
FIGS. 6C-6E are side, cross-sectional views of an aperture that extends through the catheter and engagement of an end of the support frame therein, according to some embodiments.

In addition to FIGS. 5A-5B, FIGS. 6A-6E illustrate additional aspects of some embodiments of an engagement system. FIG. 6A illustrates a support component 540' having a proximal end region 541 that comprises an aperture 543 extending therethrough. The aperture 543 can be configured to receive at least one engagement component therethrough. For example, in FIG. 6A, the engagement component 546b passes through the aperture 543 of the proximal end region 541, thus securing the proximal end region 541 relative to the aperture, the notch, or slot 539 of the catheter 510. In this manner, the proximal end region 541 can be radially secured (such that the proximal end region 541 does not radially expand out of the slot 539) and circumferentially or laterally secured (such that the proximal end region 541 does not slide out of the slot 539) relative to the catheter 510.

The proximal end region 541 can comprise a flattened portion, as illustrated in the cross-sectional view of FIG. 6B. However, the proximal end region 541 can also extend along an arcuate path without having a discrete flattened portion.

FIG. 6B (and as generally shown in the embodiment of FIGS. 5A-5B) also illustrates that the slot 539 formed in the catheter 510 can, in some embodiments, be defined by a line segment or chord 537 extending through the catheter lumen 517. The line segment or chord 537 can intersect with the circumference of the catheter 510. The line segment 537 can be a diameter of a circular cross-section, but need not be a diameter and can be a chord intersecting the circumference. The line segment 537 can define a base or bottom of the slot 539. The orientation or spacing of the line segment 537 from an outer circumference of the catheter 510 can define a slot depth. The slot depth can be measured as the distance from the line segment to the outermost point along the circumference of the catheter 510. As noted below, the slot can have a depth that extends between about $\frac{1}{5}$ and about $\frac{2}{3}$ of the catheter outer diameter, such as about $\frac{1}{4}$, $\frac{1}{3}$, or $\frac{1}{2}$ of the catheter outer diameter.

Referring still to FIG. 6B (and generally to FIG. 5B), the slot 539 can extend only partially into the catheter lumen 517, such that the lumen 517 provides sufficient space for material to pass therethrough. When viewed in cross-section, the line segment can divide the lumen 517 into first and second portions. For example, the engagement component 543 and the proximal end region 541 can be positioned within a first portion of the lumen 517. A second portion of the lumen 517 can be a clear-through portion that allows material to be urged therethrough.

Further, the proximal end region 541 can comprise at least one aperture extending therethrough. In some embodiments, the aperture can extend through the proximal end region in a direction transverse to a longitudinal axis of the support component. For example, in some embodiments, the proximal end region can be flat, and the aperture can extend through the flat proximal end region, as illustrated in FIGS. 6A-6E. However, the aperture can also extend through the proximal end region in a direction substantially parallel relative to a longitudinal axis of the support component. In such embodiments, the proximal end region can have a flat, square, rectangular, and/or twisted shape. According to some embodiments, the proximal end region 541 can be deflectable in order to facilitate placement of the proximal end region 541 into the slot 539 of the catheter 510.

The proximal end region 541 can define a width that is about equal to a width of the support component 540'. Thus, in some embodiments, the support component 540' may not have a tapering width in the proximal end region 541. However, the support component 540' can also taper toward a larger or smaller width in the proximal end region 541. For example, a larger width in the proximal end region 541 can facilitate the accommodation of the aperture 543 thereat. However, non-tapering or other tapering embodiments of the proximal end region 541 can define a width sufficient to accommodate the aperture 543 thereat.

In some embodiments, the width of the proximal end region 541 can be at least about two times the width, size, or diameter of the aperture 543. However, in other embodiments, the width of the proximal end region 541 can be three, four, five, or more times the width, size, or diameter of the aperture 543.

Figure 6D:
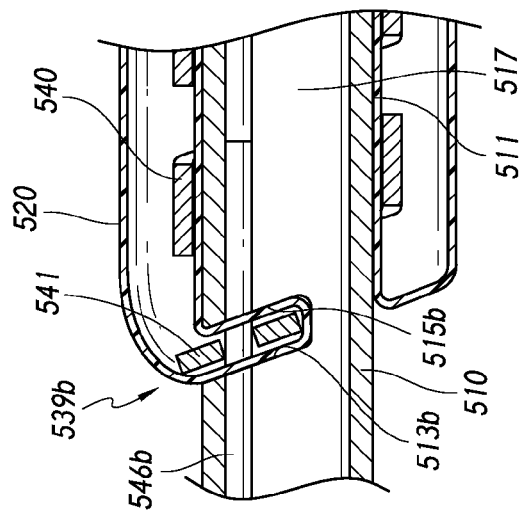
Figure 6C:
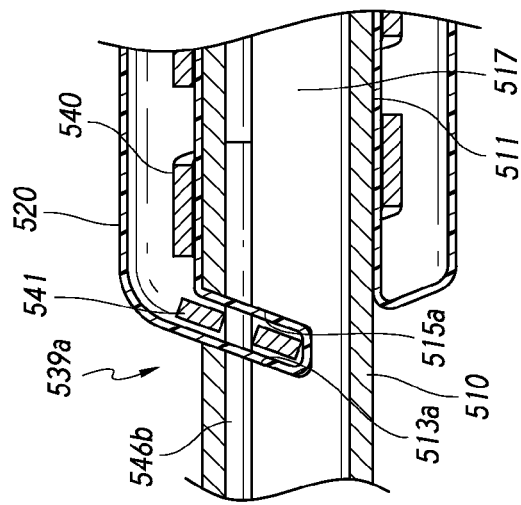

Some embodiments can also be configured such that the support component and the cover member cooperatively substantially seal the slot of the catheter lumen. FIGS. 6C-6E illustrate side, cross-sectional views of the embodiments of the catheter that can be used to couple the engagement component and the support component. According to some embodiments, the aperture, notch, or slot of the catheter can have a V-shape. However, the slot can comprise a slanted configuration and/or U-shaped configured to reduce and/or eliminate leakage of material from the slot when material is urged through the catheter lumen for deposition into the body lumen.

FIGS. 6C-6D illustrate slots 539a, 539b formed in the catheter 510, which are slanted or extend transversely relative to a plane that is perpendicular relative to the longitudinal axis of the catheter 510. FIG. 6E illustrate a slot 539c formed in the catheter 510, which extends substantially within a plane that is perpendicular relative to the longitudinal axis of the catheter 510.

In accordance with some embodiments, the slots 539a, 539b, 539c can have proximal and distal faces 513, 515. The proximal and distal faces 513, 515 can extend in respective planes. In some embodiments, the proximal and distal faces 513, 515 can be defined by edges of the catheter through which the slot is cut. The proximal and distal faces 513, 515 (or the planes through which they extend) can be substantially parallel relative to each other (whereas the slot 539 of FIG. 6A illustrates proximal and distal faces (or the planes through which they extend) that are oriented transverse relative to each other). The proximal and distal faces 513, 515 (or the planes through which they extend) can be oriented substantially perpendicular relative to a longitudinal axis of the catheter. Further, in some embodiments, the proximal and distal faces 513, 515 (or the planes through which they extend) can be obliquely oriented relative to a longitudinal axis of the catheter.

As illustrated in FIG. 6C, the slot 539a can be configured such that the proximal and distal faces 513a, 515a have a forward slant or orientation. For example, the slot 539a or the proximal and distal faces 513a, 515a can have a slope or taper that converges toward the longitudinal axis of the catheter 510 in a direction away from a supporting area 511 of the catheter 510. Thus, the proximal end portion 541 can be inserted into the slot 539a at an angle relative to the longitudinal axis of the catheter 510 and, referring to the orientation illustrated in FIG. 6C, turned counterclockwise to an angled orientation in order to insert the proximal end portion 540 into the slot 539a.

The slot 539b of FIG. 6D can be configured such that the proximal and distal faces 513b, 515b have a reverse slant or orientation. For example, the slot 539b or the proximal and distal faces 513b, 515b can have a slope or taper that converges toward the longitudinal axis of the catheter 510 in a direction toward or into a supporting area 511 of the catheter 510. Thus, the proximal end portion 541 can be inserted into the slot 539b at an angle relative to the longitudinal axis of the catheter 510 and, referring to the orientation illustrated in FIG. 6D, turned clockwise to an angled orientation in order to insert the proximal end portion 540 into the slot 539b.

Further, as illustrated in FIG. 6E, the slot 539c or proximal and distal faces 513c, 515c can extend generally perpendicular relative to the longitudinal axis of the catheter 510. Thus, the proximal end portion 541 can be inserted into the slot 539c at a substantially perpendicular angle relative to the longitudinal axis of the catheter 510 and, referring to the orientation illustrated in FIG. 6E, turned clockwise or counterclockwise to an angled orientation in order to insert the proximal end portion 540 into the slot 539a.

Advantageously, the slots 539a, 539b, 539c each are configured such that the proximal and distal faces of the slots 539a, 539b, 539c closely approximate the thickness of the proximal end portion 541 and the membrane 520 wrapped around the proximal end portion 541 when inserted into the slot. Accordingly, in embodiments of the catheter that do not comprise a dedicated or separate lumen for passage of material, the material passing through the catheter lumen 517 will not tend to leak from or exit the slot of the catheter lumen 517.

For example, the slots 539a, 539b, 539c can define a slot width, between the proximal and distal faces, that is between about 0.004 inches and about 0.012 inches. Further, the slot width can be between about 0.005 inches and about 0.010 inches. Furthermore, the slot width can be between about 0.006 inches and about 0.008 inches, or about 0.007 inches. As shown in FIG. 6A, the slot may be tapered (have a trapezoidal shape, when viewed in a side view along the longitudinal axis of the catheter) with a wider end positioned toward the outer contour of the catheter. Further, as shown in FIGS. 6C-6E, the slot may be straight (have a rectangular or square shape, when viewed in a side view along the longitudinal axis of the catheter).

In some embodiments, the thickness of the distal end portion 541 of the support component 540 can be between about 0.002 inches and about 0.008 inches. Further, the thickness of the distal end portion 541 can be between about 0.003 inches and about 0.006 inches. In some embodiments, the thickness of the distal end portion 541 can be about 0.004 inches.

Thus, with a cover member 520 having a thickness of between about 0.0005 inches and about 0.006 inches, the distal end portion 541 and cover member 520 can fit into the slot with high dimensional accuracy in order to reduce any gap in the slot wherethrough material can exit the catheter lumen.

Additionally, the slots 539a, 539b, 539c can define a slot depth or dimension indicative of the diametric or radial extent of the slot into or through the catheter 510. The slot depth can be between about ⅕ and about ⅔ of the catheter outer diameter, such as about ¼, ⅓, or ½ of the catheter outer diameter. The slot depth can be at least ⅓, ½, ⅔, or ¾ of the width of the proximal end portion 541. For example, the slot depth can be between about 0.004 inches and about 0.110 inches. Further, the slot depth can be between about 0.008 inches and about 0.090 inches. The slot depth can be between about 0.010 inches and about 0.060 inches. Furthermore, the slot depth can be between about 0.014 inches and about 0.040 inches. The slot depth can be or between about 0.018 inches and about 0.030 inches. In some embodiments, the slot depth can be about 0.020 inches, about 0.024 inches, or about 0.028 inches.

Further, the engagement component can have a diameter of between about 0.001 inches and about 0.020 inches, between about 0.003 inches and about 0.010 inches, or between about 0.004 inches and about 0.007 inches, such as 0.005 inches.

The proximal end portion can define a width of between about 0.010 inches and about 0.030 inches, between about 0.012 inches and about 0.020 inches, between about 0.014 inches and about 0.018 inches, and in some embodiments, about 0.015 inches.

In some embodiments, the catheter lumen can have an inner diameter of between about 0.010 inches and about 0.080 inches, between about 0.015 inches and about 0.070 inches, between about 0.020 inches and about 0.060 inches, between about 0.025 inches and about 0.050 inches, or between about 0.030 inches and about 0.040 inches.

Further, the catheter can have an outer diameter of between about 0.020 inches and about 0.160 inches, between about 0.030 inches and about 0.140 inches, between about 0.040 inches and about 0.120 inches, between about 0.050 inches and about 0.100 inches, or between about 0.060 inches and about 0.080 inches. In some embodiments, the catheter outer diameter is about 3 Fr, 4 Fr, 5 Fr, 6 Fr, 7 Fr, 8 Fr, 9 Fr, 10 Fr, 11 Fr, or 12 Fr.

Thus, the slot depth can be configured such that the proximal end portion can be inserted into the slot and a sufficient width of the proximal end portion can be received within the slot to allow the aperture to be accessible to the engagement component extending within the catheter lumen.

Furthermore, although FIGS. 6C-6E illustrate embodiments of a single slot, the catheter can be configured to comprise two or more slots that can be used to couple the support component thereto. One or both of the two or more slots be configured such as the slots illustrated by elements 539, 539a, 539b, or 539c. Thus, the two or more slots can be identical or different in size, shape, or orientation. Further, the catheter can comprise a single or dual lumen structure. According to some embodiments, the slot structures and embodiments illustrated in FIG. 6C-6E can be particularly advantageous for tending to reduce and/or eliminate leakage through the slots of a single lumen catheter structure.

For any embodiment of the assembly and/or implant disclosed herein, the slot width, slot depth, catheter lumen inner diameter, catheter lumen inner diameter, engagement component diameter, aperture diameter, proximal end portion width, and proximal end portion thickness can be configured within any of the ranges disclosed herein.

In some embodiments, a portion of the catheter can be configured to move beyond or through the distal portion of the implant in order to precisely deliver a material into the lumen downstream of the implant. The implant distal portion (e.g., a valve component of the implant) and the catheter distal tip can have a close fit, thus allowing material to be injected into the lumen while avoiding dispersion or diffusion of the material upstream of the implant. For example, in some embodiments, the implant proximal portion can be maintained engaged with the catheter while the implant distal portion is allowed to expand into contact with the vessel wall. The expansion of the implant distal portion can cause the implant to foreshorten and thus cause the distal portion of the catheter to move beyond or through the distal portion of the implant, whereafter material can be injected into the lumen, thus avoiding dispersion or diffusion of the material upstream of the implant.

However, in some embodiments, the implant distal portion can be maintained engaged with the catheter while the implant proximal portion is allowed to expand into contact with the vessel wall, whereafter material can be injected into the lumen, thus avoiding dispersion or diffusion of the material upstream of the implant.

According to some embodiments, while a proximal or distal portion of the implant is initially expanded with the other portion being maintained engaged with the catheter, or after both portions of the implant are expanded and released from the catheter, the catheter can be urged distally relative to the implant distal portion such that the catheter distal tip extends beyond or through the implant distal portion.

In any of such embodiments, the deployment handle and its pull member(s) can be interconnected with the engagement component(s) to allow desired actuation of the assembly and implant. When two pull members are used, the proximal pull member can be interconnected with the engagement component that controls release of either the distal or proximal implant portion. Accordingly, some embodiments disclosed herein can allow a clinician to target specific regions and precisely control the flow and dispersion of the material.

Referring now to FIGS. 7A-12B, various embodiments of the implant 520 are illustrated in which the implant 520 comprises different valve components.

FIGS. 7A-7B illustrate an implant 520a having a valve component 542a that comprises a flap structure 550a. The flap structure 550a can extend distally from the implant 520a. The flap structure 550a can comprise one or more sections of material of a cover member 544a. In some embodiments, the flap structure 550a can comprise at least an outer layer of the cover member 544a. For example, the cover member 544a can comprise inner and outer sections 545a, 545b. The inner and outer sections 545a, 545b can at least partially envelop, enclose, or cover the support component 540.

In some embodiments, the cover member 544a can comprise a tubular membrane that is everted or inverted such that the outer section 545b extends along an exterior of the support component 540 and the inner section 545a extends along an interior of the support component 540. The cover member 544a can be unitarily formed as an uncut, continuous tube or can comprise one or more longitudinal cuts or breaks such that the inner or outer sections 545a, 545b comprise one or more strips of material. The cover member 544a and/or the implant 520a can comprise additional features such as those disclosed in co-pending U.S. patent application Ser. No. 14/044,794, filed Oct. 2, 2013, the entirety of which is incorporated herein by reference.

As illustrated in FIG. 7A, in some embodiments, the inner section 545a can comprise one or more strips of material that can be secured to the distal end portion of the outer section 545b using a mechanical, thermal, or chemical coupling. For example, a suture, adhesive, or tie coupling 547 can be used to couple a strip of the inner section 545a with the distal end portion of the outer section 545b. In some embodiments, the flap structure 550a can comprise the coupling 547; however, the coupling 547 can also be omitted from the flap structure 550a and implant 520a.

In some embodiments, such as that illustrated in FIGS. 7A-7B, the coupling 547 can secure only a portion of the inner or outer sections 545a, 545b to each other. However, in some embodiments, the entire inner section 545a can be secured to the entire outer section 545b. As shown in FIG. 7B, a distal portion 548a of the implant 520a can be released (using the engagement component 546a) while a proximal portion 549a is maintained in engagement (using the engagement component 546b). As the distal portion 548a expands and the implant 520a foreshortens, the coupling 547 can be drawn proximally. At this point, in some embodiments of the methods or procedures disclosed herein, a material (e.g., embolic material, contrast agents, or drugs) can be passed through a delivery lumen 570 of the catheter 510 (shown by arrows 571) into downstream vasculature 559 of the vessel 561 (see FIGS. 7C-7D). However, the material can also be delivered after the proximal portion 549a has been released. For example, the distal tip 564 of the catheter 510 can then move distally beyond the distal portion 548a of the implant 520a to provide a clear outflow pathway for material injected through the catheter 510.

The catheter can comprise a single or dual lumen structure in combination with any of the embodiments disclosed herein. FIGS. 7A-7B and 8A-8C illustrate a single lumen structure while FIGS. 9A-10B illustrate a dual lumen structure.

FIGS. 7C-7D illustrate the release, closing, and sealing of the valve component 542a in a lumen 561. These figures illustrate that the distal portions of the inner and outer sections 545a, 545b can be coupled together or closed on top of each other. For example, in some embodiments, the inner and outer sections 545a, 545b can be closed using an adhesive material, which can be injected through the delivery lumen 570 of the catheter 510. Applicant has found that such embodiments can advantageously provide a simple construction and at least a partially or fully complete seal to be achieved by adhering the inner and outer sections 545a, 545b to each other. FIG. 7C illustrates an initial reflux or vacillation of the distal portions of the inner and outer sections 545a, 545b. During the back-and-forth movement represented in FIG. 7C, the distal portions can tend to adhere to each other until being coupled to each other to close the lumen 561, thereby preventing flow therethrough, as shown in FIG. 7D. Thereafter, the implant 520a can at least partially or fully occlude the lumen 561.

In some embodiments, the procedure for expanding the cover component and support component of the implant can be modified such that the cover component expands into contact with the body lumen wall before the support component begins expanding. For example, the cover component can be inflated by flushing the cover component with saline or other material prior to releasing or permitting expansion of an end of the support component. This inflating step can be performed in operating any of the implants that have a substantially closed end prior to expansion of the support component, which can permit an increase in fluid pressure within the cover component sufficient to inflate the cover component (see e.g., FIGS. 9A, 10A, 11A, and 12A that have valve components in a substantially closed position prior to support component expansion; but see e.g., FIG. 7A that has an open end formed by loose ends of the cover component). Further, as the cover component is inflated, the valve component of the cover component can draw closer to the distal end of the catheter, which can provide various advantages and permit operation of the valve component using the distal end of the catheter, according to some embodiments.

Further, in some embodiments, the valve component can satisfy to seemingly opposite goals: (1) to provide eventual occlusion of the vessel and prevent or reduce reflux of material into a proximal portion of the vessel, and (2) to provide a secondary opportunity to return at a later time to provide a further treatment of the vessel without removing, destroying, or otherwise damaging the valve component.

Figure 8A:
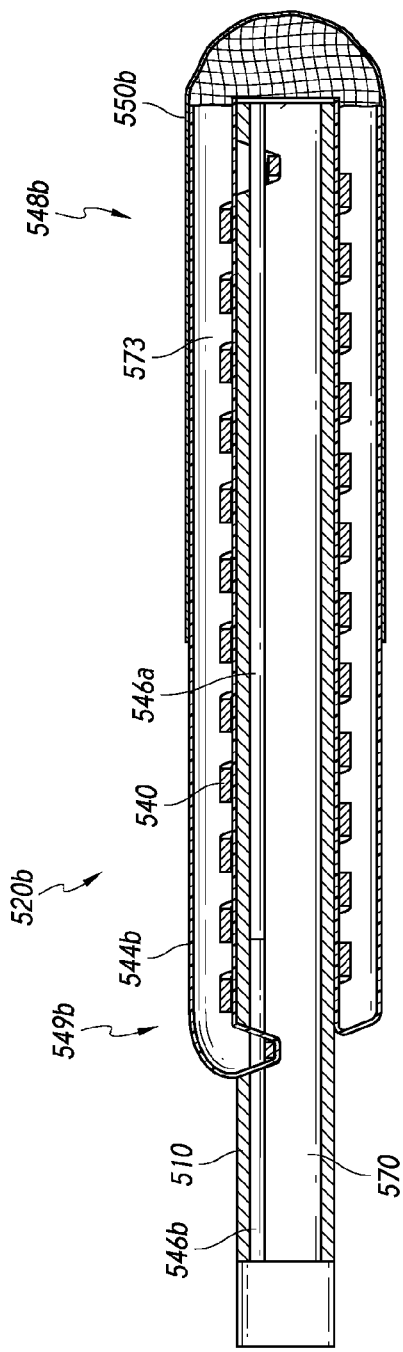

For example, in some embodiments, the valve component can comprise a mesh or fibrous material. FIGS. 8A-8D illustrate an implant 520b in a collapsed and expanded configurations. In FIG. 8A, the implant 520b comprises a cover member 544b that at least partially encloses, envelops, or covers the support frame 540. The implant 520b can comprise distal and proximal portions 548b, 549b. The implant 520b can also comprise a mesh portion 550b that is coupled to the distal portion 548b of the implant 520b.

The mesh portion 550b can comprise a plurality of filaments, woven ePTFE strips or sutures, or other porous, biocompatible materials. The mesh portion 550b can be coupled to the distal portion 548b, such as by being coupled to the distal portion of the cover member 544b. As illustrated in FIGS. 8A-8D, the mesh portion 550b can comprise a layer of material that is coupled to an outer surface of the cover member 544b along a distal portion of the cover member 544b. The mesh portion 550b can be secured relative to the cover member 544b using mechanical, thermal, or chemical bonding, such as adhesives. In some embodiments, a frictional engagement can secure the mesh structure 550b relative to the cover member 544b. For example, when the implant 520b is expanded into contact with the vessel wall, the mesh portion 550b can be secured relative to the implant 520b and support structure 540 by virtue of radial compressive force and frictional engagement against the vessel wall and the outer surface of the cover member 544b.

The mesh portion 550b can also be formed with the cover member 544b from a single, continuous piece of material. For example, in some embodiments, the mesh portion 550b can be formed as a tubular body having an open end and a closed end, opposite the open end, that comprises a plurality of pores, cells, apertures, perforations, incisions, windows, or other cuts to provide a substantially mesh-type closed end.

Thus, in some embodiments, the cover member 544b can also be configured as a material having a closed mesh end. In order to manufacture some embodiments of an implant, the tubular mesh body can be moved onto the distal portion of the catheter 510, with the catheter 510 entering the open end of the tubular body. The support component 540 can then be positioned over a distal section of the tubular body and coupled relative to the catheter 510. Further, a proximal section of the tubular body, extending proximally of the support component 540, can thereafter be everted over the support component 540 to at least partially cover the support component 540. In some embodiments, the proximal section can be at least partially coupled to a corresponding portion of the distal section of the tubular body or mesh portion. Further, in some embodiments, the proximal section of the tubular body can extend fully distally of the support component 540.

In use, the mesh portion 550b can effectively protect against or tend to block proximal migration or reflux of material ejected into the downstream vasculature 559 of the vessel 561. For example, although the mesh portion 550b can be sufficiently porous (e.g., have an average pore size) that is greater than the size of particles of a material passing therethrough, thrombosis and/or the use of materials, such as glues, can tend to close the size of the pores of the mesh portion 550b. Accordingly, after the particles of the material have passed through the mesh portion 550b, the mesh portion 550b can tend to prevent proximal migration or reflux. The mesh portion 550b can thereby provide at least partial or full occlusion of the vessel 561.

Additionally, as similarly discussed further below with regard to FIGS. 23A-24B, the embodiment shown in FIGS. 8A-8D can allow a secondary operation to be performed, such as to deposit additional material into the downstream vasculature 559, by dissolving the clotted material on the mesh portion 550b. The mesh portion 550b can be cleared such that additional material can be passed therethrough during the second operation. For example, after the implant has been placed and has occluded the vessel, the mesh portion 550b can be cleared and flow through the implant can be restored by injecting a material, fluid, or saline through the mesh portion 550b. A catheter can be advanced until a distal end of the catheter is positioned adjacent to the mesh portion 550b. Thereafter, a material, fluid, or saline can be ejected from the distal end of the catheter against the mesh portion 550b. This ejection can serve to clear the thrombosed material mesh portion 550b.

Accordingly, in some embodiments, the clinician can clear or unblock the mesh portion 550b to deposit further material in the target region in a second procedure without puncturing, piercing, or otherwise damaging the implant 520b. After clearing the mesh portion 550b, the clinician can inject additional material to the target region.

Additionally, in some embodiments, the clinician may elect to place a second implant at the site of the first implant (see e.g., FIGS. 24A-24B) without puncturing, piercing, or otherwise damaging the implant 520b.

Figure 8B:
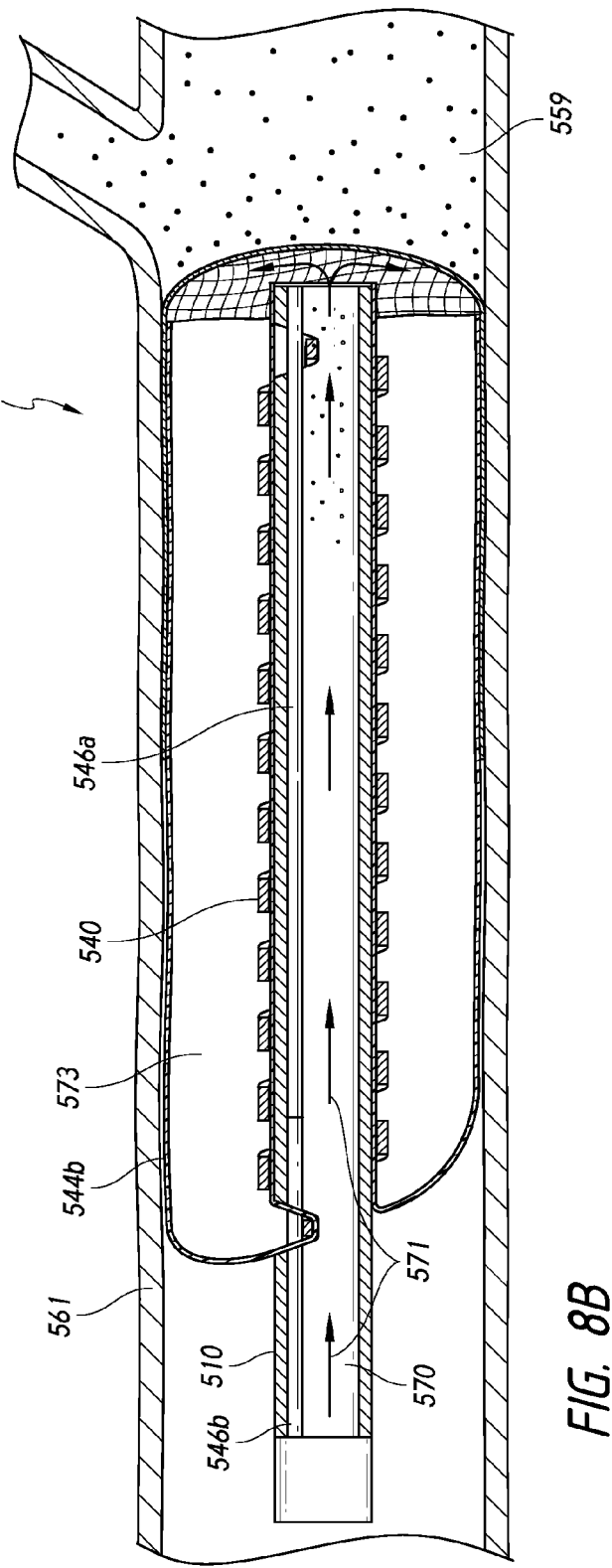

Referring now to FIGS. 8B-8C, the cover member 544b of the implant 520b can be initially expanded by introducing fluid or material 571 through the catheter lumen 570 into an interior chamber 573 formed between a layer of the cover member 544b positioned against the catheter 510 and a layer of the cover member 544b surrounding the support component 540. Accordingly, the cover component 544b can be inflated by flushing the cover component 544b prior to releasing or permitting expansion of the support component 540. The substantially closed end formed by the mesh portion 550b can allow an increase in fluid pressure within the interior chamber 573 sufficient to inflate the cover component 544b until the cover component 544b comes in contact with a vessel wall 561.

According to some embodiments, the mesh portion 550b can be configured to block or restrict flow therethrough when the fluid pressure is less than 240 mm Hg or 5 pounds per square inch ("psi"). However, for fluid pressures above 5 psi, the mesh portion 550b can expand or deflect such that the plurality of pores, cells, apertures, perforations, incisions, windows, or other cuts opens to permit flow through the mesh portion 550b.

For example, in some embodiments, a fluid or material 571 can be injected through the catheter lumen 570 and into the interior chamber 573 such that the fluid or material 571 in the interior chamber 573 is at a pressure greater than 5 psi, such as between about 10 psi and about 200 psi, between about 40 psi and about 180 psi, or between about 70 psi and about 140 psi. The delivery pressure can be varied by using certain delivery mechanisms. For example, using a 5 mL syringe, the fluid or material can be delivered at between about 80 psi and about 100 psi. Further, using a 3 mL syringe, the fluid or material can be delivered at between about 120 psi and about 140 psi. Furthermore, using a 1 mL syringe, the fluid or material can be delivered at about 200 psi.

At such high fluid delivery pressures, the mesh portion 550b can permit passage of the material 571 (shown in FIGS. 8B-8D as an embolic material) to the downstream portion 559 of the vessel when injected through the catheter lumen 570. However, in some embodiments, after the implant 520b is released into the vessel 561 (see e.g., FIG. 8D), even under severely elevated systolic pressure (e.g., above 240 mm Hg or about 4.6 psi), the mesh portion 550b can be configured to block or restrict flow through the mesh portion 550b. Further, in some embodiments, a glue or embolic material can be injected and can tend to occlude the pores, cells, apertures, perforations, incisions, windows, or other cuts of the mesh portion 550b, thus sealing the mesh portion 550b. The "seal" of the mesh portion 550b can be reversible, as discussed above.

In some embodiments, the mesh portion 550b can also be configured such that the pores, cells, apertures, perforations, incisions, windows, or other cuts of the mesh portion 550b define an open configuration and a closed configuration. The open configuration can be achieved when the cover member 544b is in a generally unexpanded configuration, as illustrated in FIG. 8A. When in the unexpanded configuration, material 571 can be passed through the mesh portion 550b. However, when a sufficient amount of material 571 has been deposited into the downstream vasculature 559 through the mesh portion 550b, the support component 540 can be expanded, thus causing expansion of the mesh portion 550b and, in some embodiments, shrinking of the pores, cells, apertures, perforations, incisions, windows, or other cuts of the mesh portion 550b. Thereafter, when a glue or embolic material is used, the glue or embolic material can act to further close or seal the pores, cells, apertures, perforations, incisions, windows, or other cuts of the mesh portion 550b. The "seal" of the mesh portion 550b can be reversible, as discussed above.

FIG. 9A-10B illustrate embodiments of an implant 520c being delivered using different catheters, which can provide unique benefits and advantages. FIGS. 9A and 10A, illustrate an implant 520c having a valve component 542c that comprises a flap structure 550c. The flap structure 550c can comprise a flat plate that is attached to a distal end 560 of the cover member 544c or to a distal end of the support component 540. The flap structure 550c can be resiliently biased toward a closed position (as shown in FIGS. 9A and 10A) in which the flap structure 550c covers an aperture 562 of the implant 520c.

However, upon expansion of the implant 520c (illustrated as expansion of a distal portion 548c of the implant 520c in FIGS. 9B and 10B), proximal foreshortening of the implant 520c can cause a distal tip 564 of the catheter 510, 510' to be advanced distally relative to the implant distal portion 548c, thus contacting against the flap structure 550c. When the distal tip 564 presses against the flap structure 550c, the flap structure 550c will tend to deflect from the closed position, thus opening the lumen of the implant 520c such that it is in fluid communication with the lumen of the vessel into which the implant 520c is being deployed. The distal tip 564, 564' of the catheter 510, 510' can then move distally beyond the distal portion 548c of the implant 520c, and as shown, have a clear outflow pathway for material injected through the catheter 510, 510'.

Further, the catheter 510, 510' can comprise a material delivery lumen 570 through which material can be passed toward the target region. The catheter 510 can also comprise a distal port 572, 572' in communication with the lumen 570. As noted above, when the catheter distal tip 564, 564' moves distally beyond the distal portion 548c of the implant 520c, the port 572, 572' will provide a clear outflow pathway for material injected through the lumen 570. The port 572, 572' can therefore be moved into a position in which it is in unobstructed, fluid communication with the target region, as illustrated in FIGS. 9B and 10B. Accordingly, material can then be delivered through the lumen 570 and out through the port 572, 572' into the target region. The lumen 570 can also be used to flush the implant or pass other fluids through the implant or toward a downstream section of the blood vessel.

FIGS. 9A-9B illustrate that the distal tip 564 of the catheter 510 can comprise a generally flat face that is oriented substantially orthogonal relative to the longitudinal axis of the catheter 510. In such embodiments, the distal tip 564 can be moved relative to the distal portion 548c of the implant 520c until the flap structure 550c is moved away from the closed position shown in FIG. 9A toward the open position shown in FIG. 9B, thereby allowing the port 572 to have a clear outflow pathway for material to be ejected from the lumen 570.

FIGS. 10A-10B illustrate an embodiment of the distal tip 564 in which the port 572' is facing generally downward or radially outward relative to the longitudinal axis of the catheter 510'. Such embodiments can provide an advantageous beveled or angled configuration, which may need to move the flap structure 550c only a short length or make a single point of contact in order to achieve a clear outflow pathway for the material to be ejected from the lumen 570. According to some embodiments, the bevel of the catheter 510' can be modified such that the catheter 510' defines a generally conical tip or the bevel can be removed entirely such that the distal tip 564 is generally flat, as illustrated in FIGS. 7A-7B, 9A-9B, and 11A-12B.

After the desired saturation or amount of embolic material been released, the implant 520c can be entirely removed from the vessel or implanted at the target region. For example, a proximal portion 549c of the implant 520c can be released and allowed to expand into apposition with the vessel wall. Thus, in accordance with some procedures, material can be released into the target region and flow through the vessel can be occluded using the implant 520c, thereby inducing infarction of the target region.

FIGS. 11A-12B illustrate additional embodiments of an implant 520c having a valve component 542d and movement of the catheter distal end 564 distally beyond the implant distal end. For example, FIGS. 11A-11B illustrate a dome-shaped valve component 542d. The dome-shaped valve component 542d can comprise a pair of opposing, flexible half-dome structures 580 that can be biased toward each other such that a slit or gap between the structures 580 is in a substantially closed position.

Similar to the discussion above regarding the embodiment in FIG. 9A-9B, the distal end 564 of the catheter 510 can be urged or moved through the aperture 562 of the implant 520d, thus contacting the structures 580 and causing separation thereof, such that the gap or slit between the structures 580 is opened and the lumen 570 of the catheter 510 is placed in fluid communication with the target region, as shown in FIG. 11B.

Additionally, FIGS. 12A-12B illustrate an embodiment of an implant 520e having a valve component 542e, in the form of an iris diaphragm-type valve structure. The valve component 542e can comprise a plurality of flexible leaflets or structures 590 that can be biased toward each other such that an aperture 592 between the structures 590 is in a substantially closed position.

Similar to the discussion above regarding the embodiment in FIG. 9A-11B, the distal end 564 of the catheter 510 can be urged or moved through the aperture 562 of the implant 520d, thus contacting the structures 590 and causing separation thereof, such that the aperture 592 between the structures 590 is opened and the lumen 570 of the catheter 510 is placed in fluid communication with the target region, as shown in FIG. 12B.

In addition to the embodiments discussed above, which can be carried on a distal engagement section of the catheter, other embodiments can be provided in which the implant is delivered by distally advancing the implant through a lumen of the catheter. Thus, instead of engaging the implant externally to the catheter, the implant can be advanced internally to the catheter, such as by pushing or pulling the implant through the lumen. In some embodiments, support and valve components of the implant can be collapsed into an elongate position and released into an expanded position within the vessel. Features and aspects of the implants, including the support component and the valve component, are also disclosed in U.S. Application No. 61/904,376, filed Nov. 14, 2013, titled Implantable Luminal Devices and Methods (086538-0041), the entirety of which is incorporated herein by reference. Further, any of the valve components disclosed herein (see e.g., FIGS. 7A-16B) can be used with a helical support component that can be coupled to a catheter (as shown in FIGS. 3-12B) or a deflectable support component that can be at advanced within a catheter (as shown in FIGS. 13-16B), including any combinations or modifications thereof.

Figure 13:
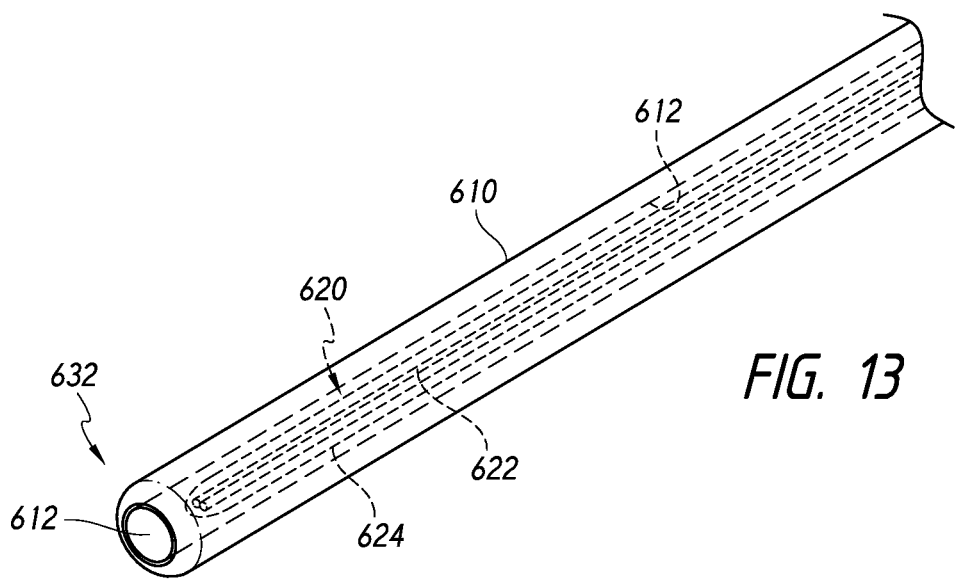
FIG. 13 shows a perspective view of a frame in a compressed state within a deliver catheter, according to some embodiments.
Figure 14A:
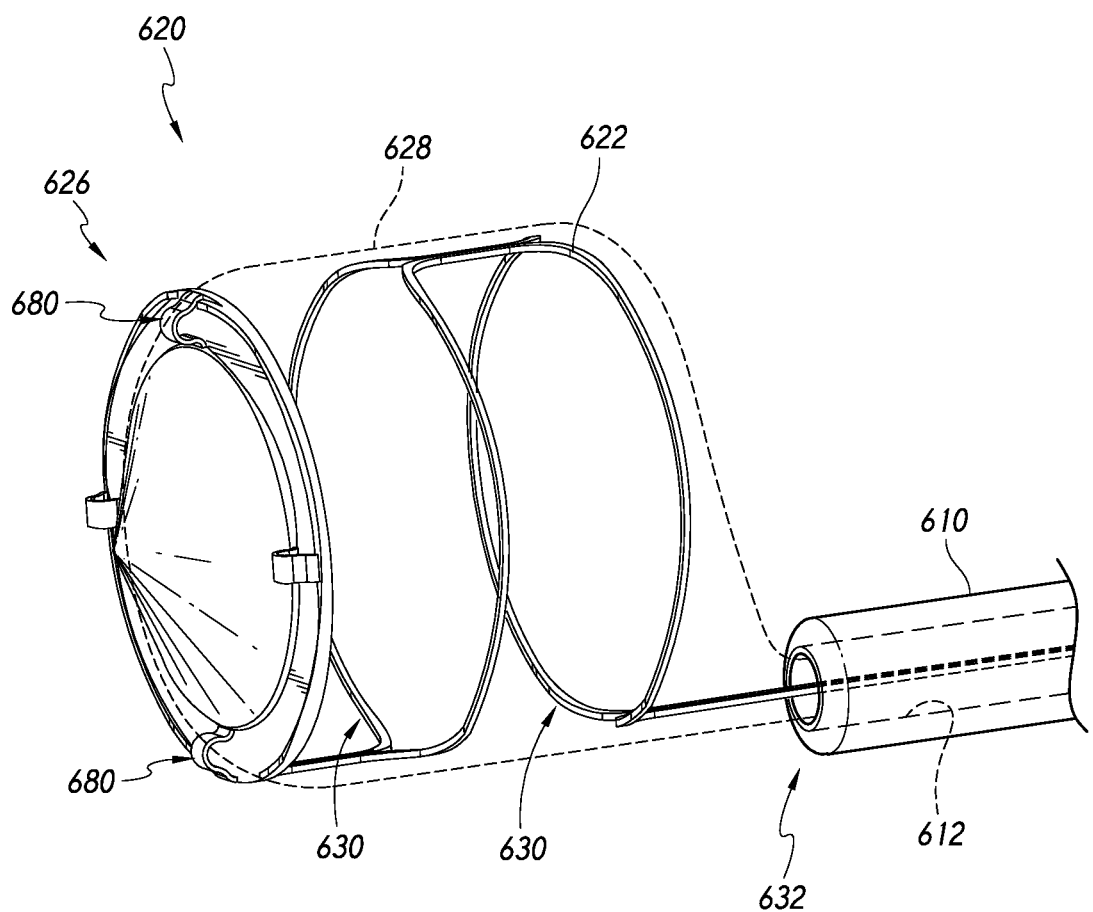
FIG. 14A shows a perspective view of a frame partially expanded from a delivery catheter, according to some embodiments.

For example, referring to FIGS. 13-14A, the implant can be delivered through a lumen of the catheter. As shown, a catheter 610 can be provided that comprises a lumen 612 configured to receive the implant 620 therein. The implant 620 can comprise a support component 622 and a cover component 624. FIG. 13 illustrates the implant 620 in a collapsed, elongated configuration, which enables the implant 620 to be moved within the catheter lumen 612.

The support component 622 and the cover component 624 can be attached to each other or be separated and freely movable relative to each other. Whether attached or separated, the support and cover components 622, 624 can be configured to be advanced through the catheter lumen 612 together, as a single unit. For example, FIG. 13 also illustrates that, according to some embodiments, the support component 620 can be at least partially enclosed, enveloped, or covered by the cover component 624 such that the support component 622 and the cover component 624 can be attached to each other and delivered together (and as shown in FIG. 14A, released into the vessel together).

However, according to some embodiments, the support and cover component 622, 624 can be separated from each other and moved through the catheter lumen 612 independently of each other. For example, the implant 620 can also be configured such that the support component 622 is deployed into the cover component 624 after the cover component 624 has been positioned within the vessel.

Once the implant 620 reaches the target area, FIG. 14A illustrates that the implant 620 can be expanded from the collapsed configuration to an expanded configuration. In the expanded configuration, the support component 622 of the implant 620 can increase in its diameter, expanding within the cover component 624. In either embodiment, whether the support component 622 and the cover component 624 are attached to each other or separated and freely movable relative to each other, when the support component 622 expands, the support component 622 can press the cover component 624 against a side wall of the lumen and thereby fix the cover component 624 (and the implant 620) within the lumen.

The cover component 624 can comprise a valve component 626 and a sheath portion 628. The valve component 626 and the sheath portion 628 can form a substantially continuous sleeve or layer (e.g., having a seal between the valve component 626 and the sheath portion 628 such that fluid passes only through an aperture or opening of the valve component 626) into which the support component 622 can expand. The aperture or opening can have a size between about 100 microns and about 3,000 microns, about 500 microns and about 2,800 microns, or about 1,000 microns and about 2,500 microns. The sheath portion 628 can be porous, nonporous, and/or comprise one or more portions that are nonporous, such as impermeable graft or other such sections.

Additionally, as illustrated above and in FIG. 13, as with various embodiments discussed herein, the support component 622 having dual wire loop features can be held in a generally linear or straight configuration within a lumen 612 of a catheter 610. The loops 630 (shown in the expanded configuration illustrated in FIG. 14A) of the support component 622 can be pulled or longitudinally stretched to create tension between open loops 630 to allow the support component 622, when deployed, to spring back to or return to an expanded shape consisting of various expanded loops 630, as illustrated in FIG. 14A, as the support component 622 exits from a distal end 632 of the catheter 610.

The support component 622 of the implant 620 can be configured as illustrated in FIGS. 13-16B, and as shown and described in U.S. Application No. 61/835,406, filed Jun. 14, 2013, titled Implantable Luminal Devices and Methods (086538-0032), the entirety of which is incorporated herein by reference. Further, various other configurations can be used, such as those disclosed in U.S. Application No. 61/904,376, filed Nov. 14, 2013, titled Implantable Luminal Devices and Methods (086538-0041). Accordingly, support component can comprise separate wires that are preset into shapes that are generally mirror images of each other along a longitudinal center plane (extending through the central axis) of the support component, as illustrated in FIGS. 13-14A. The wires extend from a first end to a second end of the support component and can be joined or connected together, either mechanically or chemically, to form the support component.

FIGS. 12-16B illustrate embodiments of implants having a support component and a valve component, which can be delivered by advancing the implant within the lumen of the catheter as opposed to being supported, engaged, or restrained along an exterior surface of the catheter.

Figure 14B:
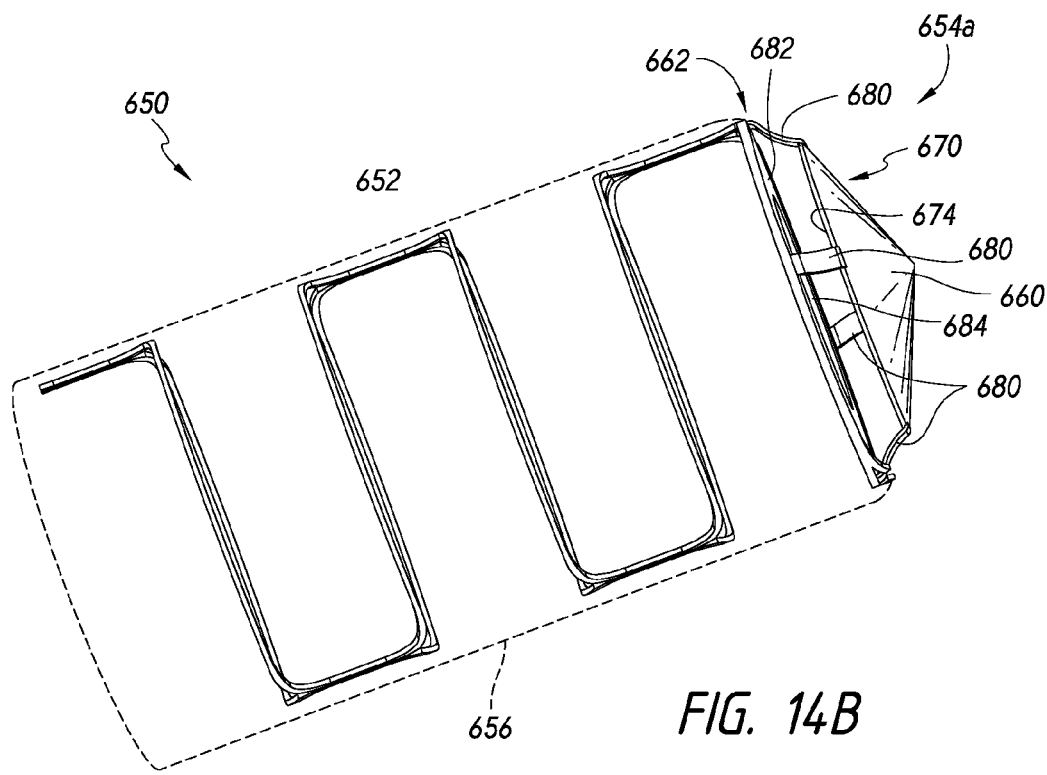
FIGS. 14B-14C are perspective views of an implant having a valve component, according to some embodiments.
Figure 14C:
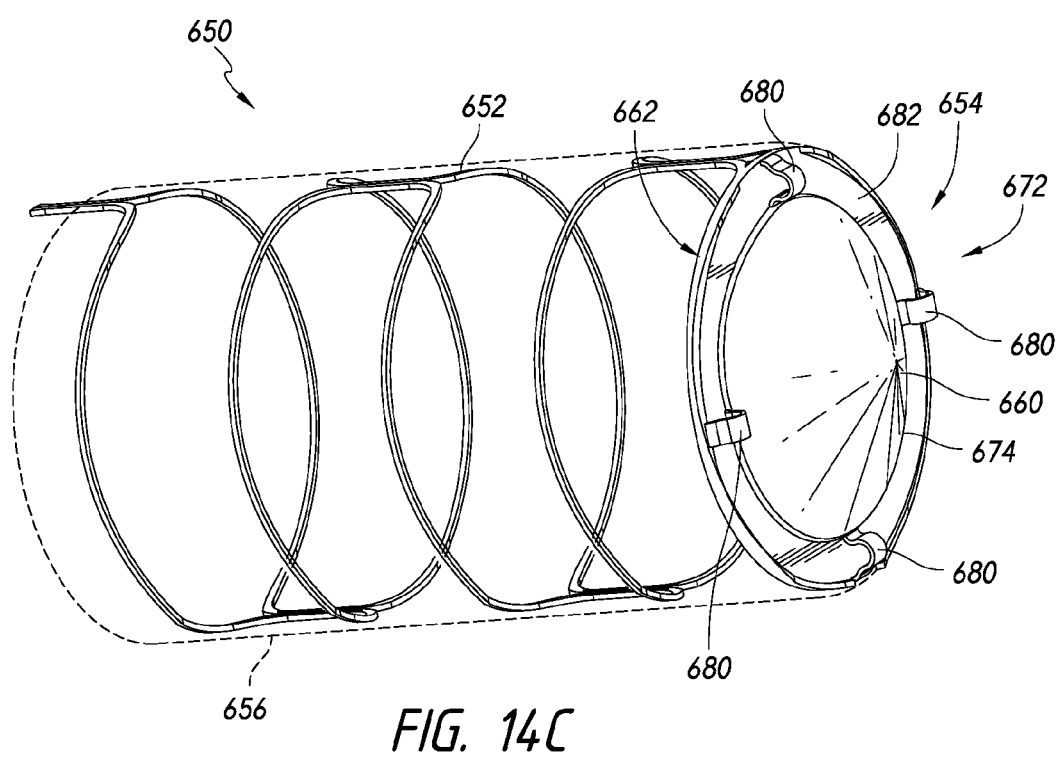

FIGS. 14B-14C illustrate an implant 650 having a support component 652, a valve component 654a, and a cover component 656. The support component 652 can be configured as illustrated and described above with respect to the support component 622 shown in FIGS. 13-14B. The valve component 654a can comprise a movable component 660 that can be attached to a first end 662 of the support component 652. The movable component 660 can be movable between an open position 670 and a closed position 672. In the open position 670, the movable component 660 can be spaced apart from the first end 662 of the support component 652 such that fluid can flow between the first end 662 and an outer perimeter 674 of the movable component 660. In the closed position 672, the valve component 654a can serve to prevent retrograde (and in some embodiments, anterograde flow) through the valve component 654a. Such embodiments can be useful to prevent displacement of embolic material outside of the target region, such as into upstream portions of the vessel, or undesired dilution of the embolic material in the target region.

In accordance with some embodiments, the movable component 660 can be moved relative to the first end 662 in response to pressure or a longitudinal force exerted against the movable component 660. For example, the movable component 660 can move away from the support component 652 (e.g., from the closed position 672 toward the open position 674 shown in FIG. 14B). The movable component 660 can be biased toward the closed position 672 such that the movable component 660 returns to the closed position 672 after being urged toward the open position 674. In the closed position 672, the movable component 660 can prevent retrograde flow through the valve component 654a.

For example, the movable component 660 may move toward and away from the nonmovable component 682. With blood flow entering the opening 684 in the nonmovable component 682, the smaller, movable component 660 can separate from the nonmovable component 682, thus creating a space for blood to pass. At a pressure less than a normal systolic pressure (e.g., less than about 120 mm Hg, less than about 110 mm Hg, less than about 100 mm Hg, less than about 90 mm Hg, or less than about 80 mm Hg), the movable component 660 can return or fall back against at least the nonmovable component 682, thus at least partially closing the opening 684 or sealing against retrograde or backflow through the vessel.

The movable component 660 can be coupled relative to the first end 662. For example, the movable component 660 can be attached using at least one fastener 680. The fastener 680 can be elastic, resilient, flexible, or inelastic. The fastener 680 can comprise at least one hinge-type fastener, a strap-type fastener, and/or material having one or more apertures extending therethrough such that fluid or material can pass out of the first end 662 of the implant 650 past the movable component 660 when the movable component 660 is in the open position 670. Thus, as illustrated in FIG. 14B, the movable component 660 can be attached using a plurality of fasteners 680 (shown as flexible strap-type fasteners) that permit anterograde flow out of the implant 650 past the movable component 660. The movable and/or nonmovable components 660, 682 can be connected by bands, strips, or ribbons so that the movable component 660 may move to and from the nonmovable component 682 freely.

According to some embodiments, the valve component 654a can also comprise a nonmovable component 682. The nonmovable component 682 can be attached to the support component 652. The nonmovable component 682 can comprise a material formed separately from and later attached to the support component 652. The nonmovable component 682 can comprise a plate, three-dimensional structure, a wire, or other feature that is attached to, dried onto, or otherwise coupled to the support component 652. For example, the nonmovable component 682 can be coupled to the distal end 662 of the support component 652 such that the nonmovable component 682 does not move longitudinally relative to the support component 652. In some embodiments, the nonmovable component 682 can be fixed relative to the support component 652.

The nonmovable component 682 can comprise at least one opening 684 through which fluid or material passing through the lumen of the implant 650 can flow and exit the lumen of the implant 650. The opening 684 can comprise one or more apertures that are formed in the nonmovable component 682. The movable component 660 can have a size greater than the size of the opening 684 such that when positioned over the opening 684, the movable component 660 can block flow through the opening 684.

In some embodiments, the nonmovable component 682 and the movable component 660 can be configured to nest, mate, or be positioned flush against each other when the valve component 654a is in the closed position. In such embodiments, the nested, mated, or flush positioning of the nonmovable and movable components 682, 660 can allow the valve component 654a to at least partially obstruct or fully block flow through the valve component 654a when in the closed position.

For example, the nonmovable component 682 and the movable component 660 can each have shapes that correspond to each other and permit the valve component to at least partially obstruct or fully block flow therethrough. In some embodiments, the nonmovable component 682 can have a substantially flat or planar shape and the movable component 660 can also have a substantially flat or planar shape. Such an embodiment as illustrated in FIGS. 14B-14C, where in the closed position of FIG. 14C, backflow against the valve component 654a would cause the movable component 662 be positioned flush against the nonmovable component 682, thus preventing flow through the opening 684.

Further, in some embodiments, the nonmovable component 682 can have a curved or arcuate shape and the movable component 660 can also have a curved or arcuate shape. As illustrated in FIGS. 14A-14C, the movable component 660 can comprise a substantially conical shape. In some embodiments, for example, the nonmovable component 682 can also comprise a substantially conical shape such that the movable and nonmovable components 660, 682 can self-center when in contact with each other or have a self-centering function. Furthermore, in some embodiments, the shape of the nonmovable and movable components 682, 660 can comprise mating components such that the nonmovable and movable components 682, 660 assume a substantially fixed rotational orientation relative to each other when the valve component 654a is in the closed position (e.g., when the nonmovable and movable components 682, 660 are nested or mated against each other).

In some embodiments, the movable and/or nonmovable components 660, 682 can be formed from a film layer, such as a fabric or other polymer (e.g., ePTFE) film that is attached to one or more of the loops of the support component 652. As shown, the nonmovable component 682 can comprise an annular or doughnut-shaped component, and the movable component 660 can comprise a solid round panel that is oversized relative to the opening 684 in the nonmovable component 682.

Figure 15A:
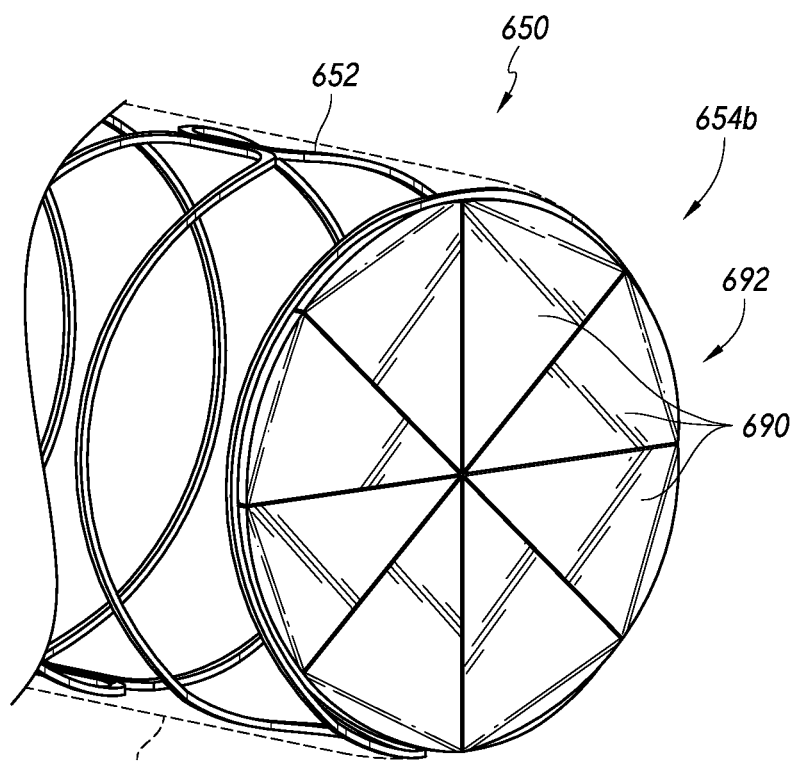
FIGS. 15A-15B are perspective views of an implant having a valve component, according to some embodiments.
Figure 15B:
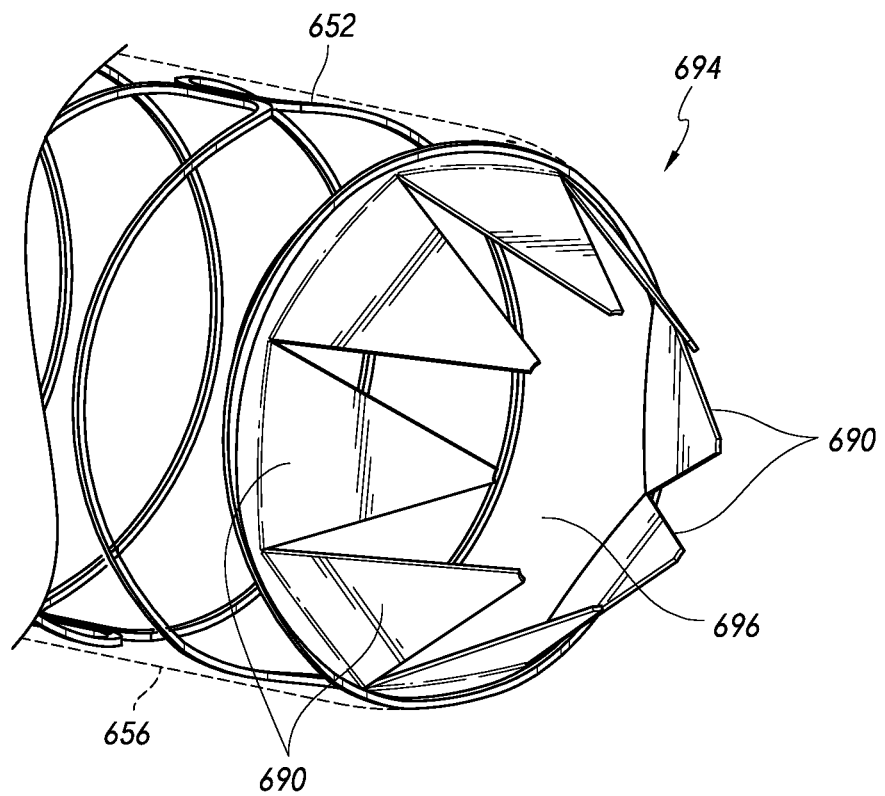

Referring now to FIGS. 15A-15B, another embodiment of a valve component is shown. In this embodiment, a valve component 654b can be used with the support component 652 and the cover component 656 of the implant 650. As discussed above similarly with regard to the valve component 654a, the valve component 654b can function to allow anterograde flow while substantially preventing retrograde flow through the implant 650.

In the embodiment illustrated in FIGS. 15A-15B, the valve component 654b can be configured as a plurality of movable panels 690 that can fold, bend, deflect, or otherwise move from a closed position 692 (FIG. 15A) to an open position 694 (FIG. 15B). For example, the valve component 654b can comprise a single layer or sheet of material having at least one cut to form at least two moving edges that can be displaced relative to each other in order to form an aperture or opening 696 between the edges. In FIG. 15B, the edges are formed by four intersecting cuts (e.g., intersecting generally perpendicularly), thus forming sixteen movable edges and eight movable panels 690. However, the valve component 654b can be configured to have two, three, four, five, six, seven, or more panels.

The valve component 654b can comprise an elastic, flexible, or deflectable material that can be biased to maintain the closed position 692 unless a threshold level of pressure is met, such as pressure exceeding a normal systolic pressure (e.g., about 120 mm Hg). Further, the valve component 654b can move toward the closed position 692 when the pressure is below a normal systolic pressure (e.g., less than about 120 mm Hg, less than about 110 mm Hg, less than about 100 mm Hg, less than about 90 mm Hg, or less than about 80 mm Hg).

Figure 16A:
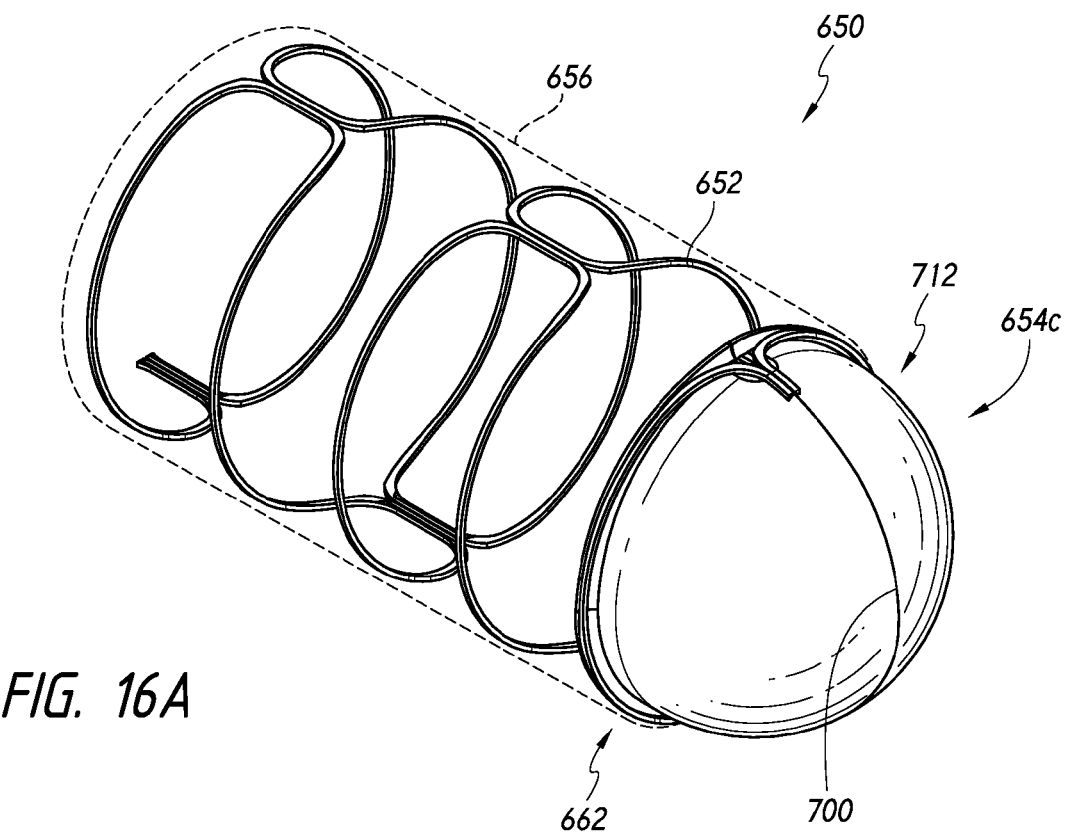
FIGS. 16A-16B are perspective views of an implant having a valve component, according to some embodiments.
Figure 16B:
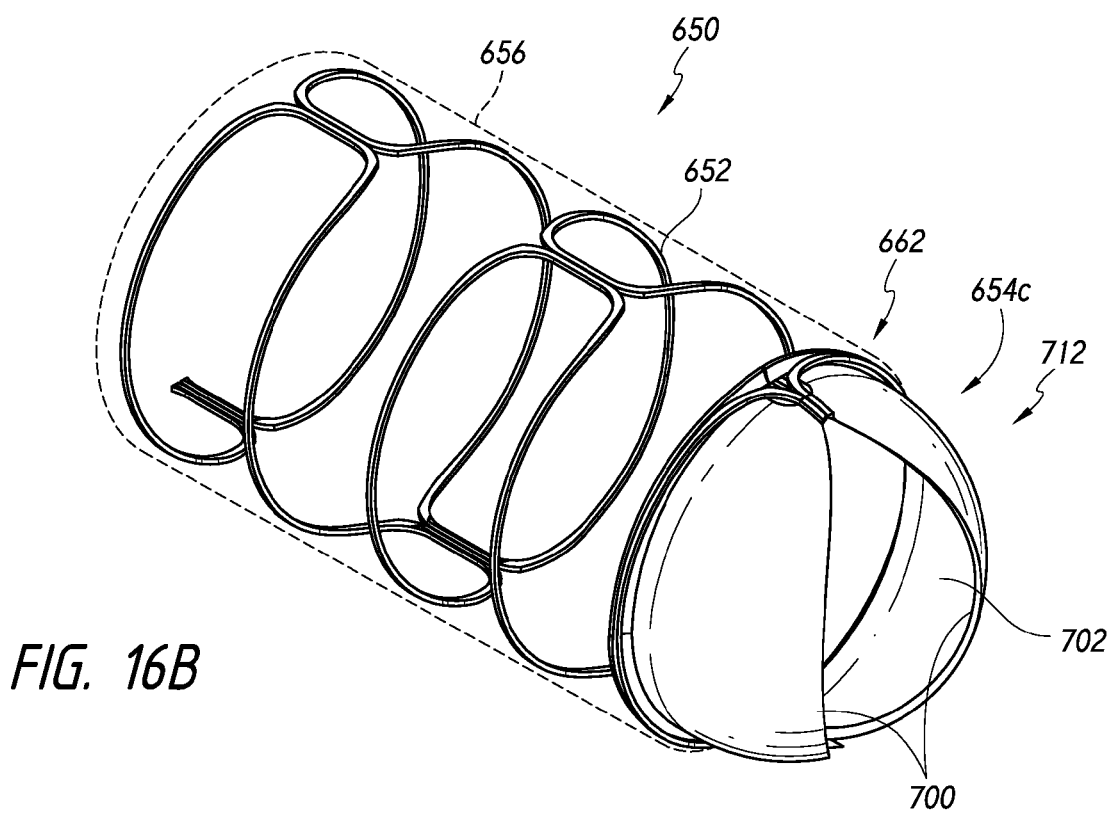

Further, as shown in FIGS. 16A-16B, a valve component 654c can also be provided in which the single layer or sheet of material has a three-dimensional shape, such as a dome, cone, pyramid, wedge, or other shapes. In FIGS. 16A-16B, the material of the valve component 654c has a single cut forming opposing edges 700 that can move relative to each other in order to open or close an aperture 702 of the valve component 654c in open or closed positions 710, 712. Multiple cuts can also be made in three-dimensionally shaped valve components. Alternatively, the valve component 654c can be formed from separate hemispherical components that are aligned and attached to the support component 652 in order to permit relative movement between the hemispherical components to open or close the aperture 702 in response to pressure fluctuations. Such components can be deflectable or rigid.

In some embodiments, the edges 700 of the aperture 702 can comprise a frame element. Both of the edges 700 can have a frame element extending therealong. The frame element can function to maintain an arcuate shape of the edges 700 such that the edges 700 can reliably meet and avoid gapping or spaces therebetween when the edges 700 meet in the closed position (as shown in FIG. 16A). In some embodiments, the frame element(s) can be a section of the support component 652 that extends from the loop of the first end 662 of the support component 652. Thus, in accordance with some embodiments, the frame element(s) can aid, support, or provide the biasing force to urge the opposing edges 700 toward the closed position 710.

As noted above with respect to the valve components 654a, 654b, the valve component 654c can also comprise an elastic, flexible, or deflectable material that can be biased to maintain the closed position 710 unless a threshold level of pressure is met, such as pressure exceeding a normal systolic pressure (e.g., about 120 mm Hg). Further, the valve component 654c can move toward the closed position 710 when the pressure is below a normal systolic pressure (e.g., less than about 120 mm Hg, less than about 110 mm Hg, less than about 100 mm Hg, less than about 90 mm Hg, or less than about 80 mm Hg).

Methods of Material Delivery

According to some embodiments disclosed herein, procedures, techniques, and implants are provided by which an implant can be deployed into a body lumen in order to deliver a material (e.g., embolic material, contrast agents, or drugs) to a target body region.

In some embodiments, the procedure can be performed such that one or more implants is fully expanded into contact with the lumen and released thereat in order to at least partially occlude flow through the lumen. Thereafter, the material can be injected through an aperture or valve of the implant into the lumen at a location downstream of the implant.

In addition, the implant can be left in place to at least partially occlude the lumen after the material has been delivered. In some instances, the implant can fully or at least substantially occlude the lumen immediately after its release into the lumen. In order to do so, the aperture or valve of the implant is closed.

The valve component of the implant can be configured to become at least partially closed once the catheter carrying the implant is withdrawn and the implant is fully released into the lumen. For example, the valve component can be at least partially closed or sealed to at least a frame of the implant, thereby at least partially closing or sealing the implant distal portion. The valve component can be closed or sealed using embolic material, adhesives, or other such materials.

In some embodiments, as discussed above, a portion of the catheter can be configured to move beyond or through the distal portion of the implant or have a close fit with the implant in order to precisely deliver a material into the lumen downstream of the implant and avoid dispersion or diffusion of the material upstream of the implant.

For example, the implant proximal portion can be maintained engaged with the catheter while the implant distal portion is allowed to expand into contact with the vessel wall (see e.g., FIGS. 17A-17D, 19A-19C, and 20A-20D). In some embodiments, the expansion of the implant distal portion can cause the implant to foreshorten and thus cause the distal portion of the catheter to move beyond or through the distal portion of the implant. Further, in some embodiments, the catheter may not move beyond or through the distal portion of the implant, but the implant distal portion can be open thereby permitting free flow of material from the catheter distal tip (see e.g., the implant illustrated in FIGS. 7A-7D). Thereafter, material can be injected into the lumen, thus avoiding dispersion or diffusion of the material upstream of the implant.

However, in some embodiments, the implant distal portion can be maintained engaged with the catheter while the implant proximal portion is allowed to expand into contact with the vessel wall (see e.g., FIGS. 18A-18D), whereafter material can be injected into the lumen, thus avoiding dispersion or diffusion of the material upstream of the implant.

Reflux of material against the implant (e.g., embolic or adhesive material) can cause at least a portion of the implant to become closed (see e.g., FIGS. 7C-7D). The implant can use a polytetrafluoroethylene ("PTFE") or expanded polytetrafluoroethylene ("ePTFE") cover member that has a plurality of ribbons extending distally and around an aperture in the distal portion of the implant. Although the ribbons will not tend to block anterograde flow through the aperture, reflux or retrograde flow of the embolic material can cause the ribbons to contact each other, adhere to one another, and become joined together as a mass that clogs and blocks the distal aperture of the implant, thereby closing or sealing the implant, as shown in FIG. 7D, for example. Such an implant configuration is discussed in co-pending U.S. patent application Ser. No. 14/044,794, filed Oct. 2, 2013, the entirety of which is incorporated herein by reference.

Further, the valve component can be closed mechanically, such as by being biased toward a closed position. Mechanical biasing can cause the valve component to be released and move toward its closed position once the implant is released and disengaged from by the catheter.

Figure 17A:
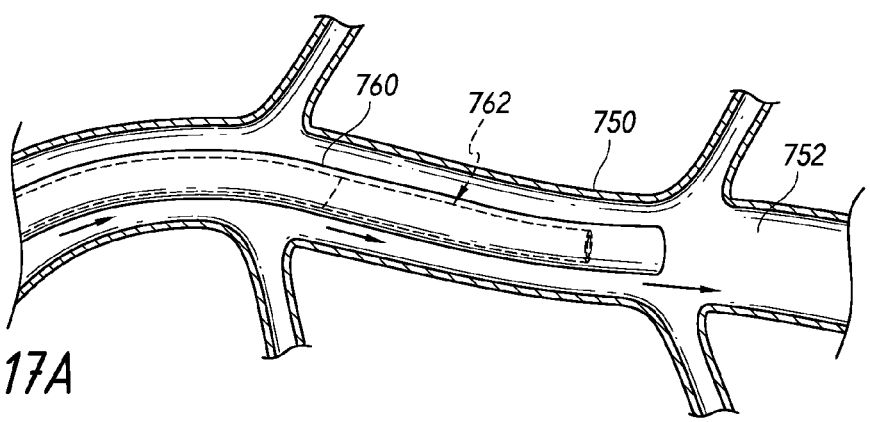
FIGS. 17A-17D are cross-sectional schematic views illustrating processes of depositing embolic particles into a target vessel region, according to some embodiments.

Referring initially to FIGS. 17A-20D, a clinician can use an embodiment of the implant disclosed herein (illustrated as the implant shown in FIGS. 7A-7D) to deposit embolic particles into a target body region. As shown in FIGS. 17A, 18A, and 20A, a guide catheter 760 can be advanced to a target region of a lumen 752 of a blood vessel 750. The vessel 750 can be an artery. Optionally, the guide catheter 760 can be advanced to the target region over a guidewire. Guidewires used in accordance with any of the embodiments disclosed herein can have a size of between about 0.005 inches and about 0.030 inches, between about 0.008 inches and about 0.024 inches, or between about 0.010 inches and about 0.018 inches, such as 0.010 inches, 0.014 inches, or 0.018 inches.

Figure 18A:
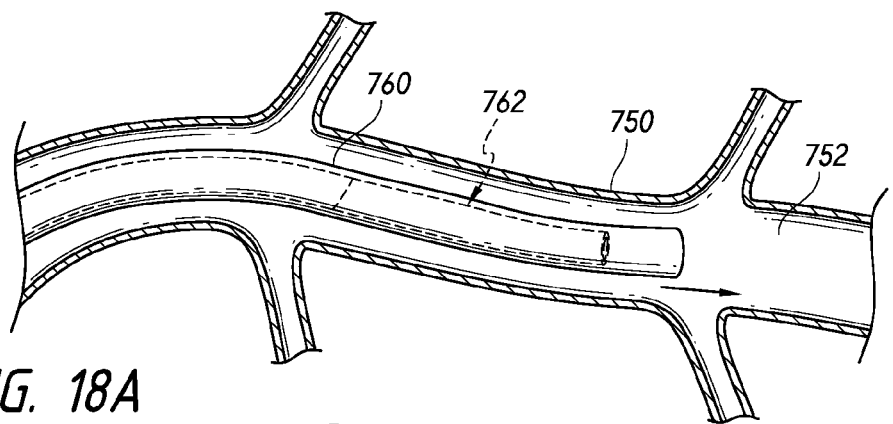
FIGS. 18A-18D are cross-sectional schematic views illustrating another process of depositing embolic particles into a target vessel region, according to some embodiments.
Figure 20A:
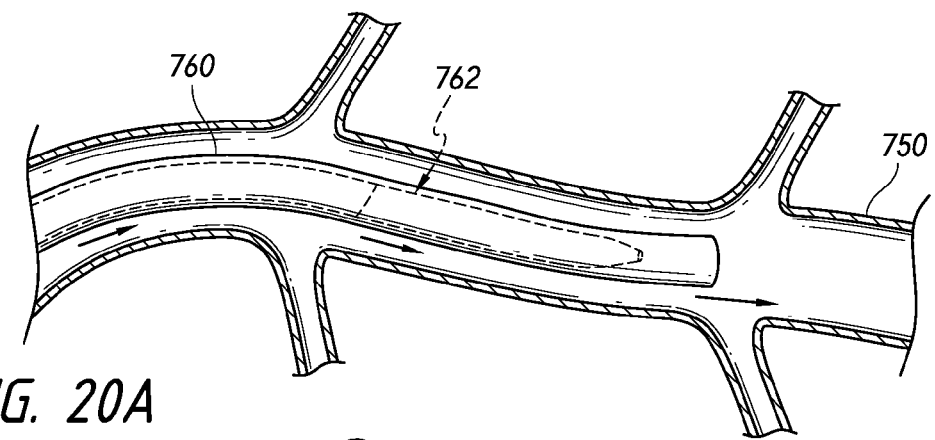
FIGS. 20A-20D are cross-sectional schematic views illustrating another process of depositing embolic particles into a target vessel region, according to some embodiments.

An implant carrier assembly 762 can be advanced to the target region. In some embodiments, the implant carrier assembly 762 can be advanced through the catheter 760 toward a distal portion of the catheter 760, as shown in FIGS. 17A, 18A, and 20A. However, in some embodiments, the catheter 760 can also be omitted and the implant carrier assembly 762 can be advanced to the target region over a guidewire, such as that mentioned above.

Figure 19A:
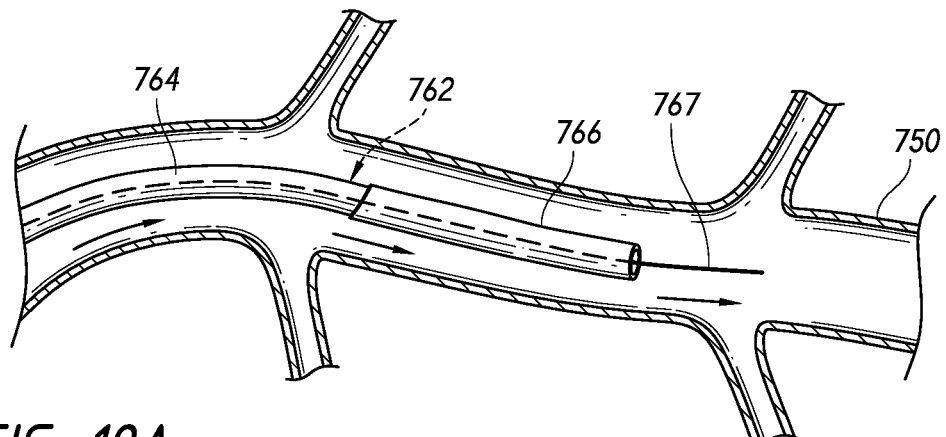
FIGS. 19A-19C are cross-sectional schematic views illustrating another process of depositing embolic particles into a target vessel region, according to some embodiments.
Figure 19B:
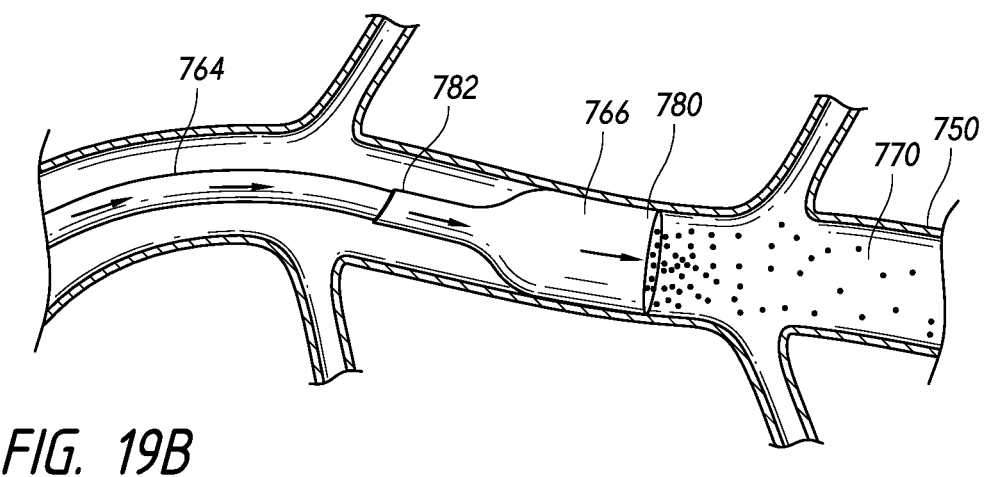
Figure 19C:
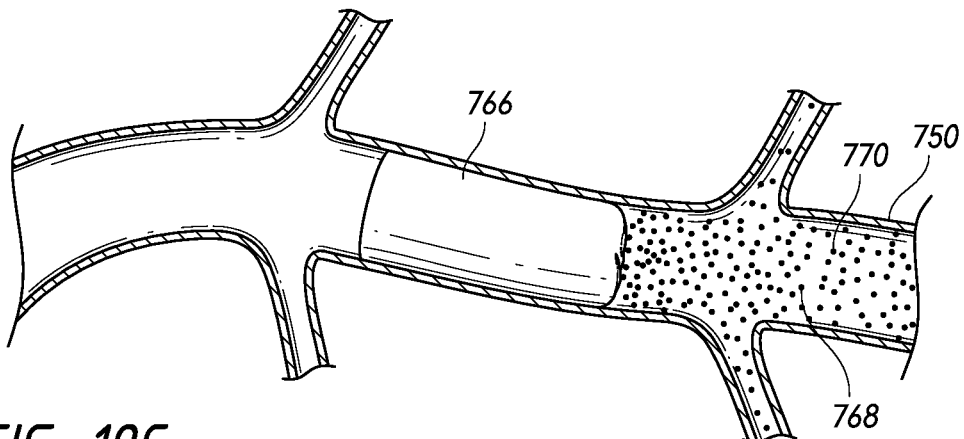

For example, FIGS. 19A-19C illustrate that methods or procedures disclosed herein can also omit the guide catheter 760. As shown, the implant carrier assembly 762 can be advanced along a guidewire 767 until reaching the target region. A supporting catheter 764 of the carrier assembly 762 can comprise a lumen that is configured to receive the guidewire 767 to facilitate distal advancement without a guide catheter or other member. Thus, in such embodiments, the supporting catheter 764 and an implant 766 carried thereon can reach much smaller vessels or arteries than in embodiments that require a guide catheter 760.

Thus, in some embodiments, including that illustrated in FIGS. 19A-19C, the implant 766 can be placed in vessels or arteries ranging in size from about 1.2 mm to about 6.5 mm, from about 1.4 mm to about 6.0 mm, and about 1.7 mm to about 3.0 mm.

The implant 766 and the supporting catheter 764 can have a passing profile or outer diameter of between about 3 Fr and about 8 Fr, or that can be compatible with a guide catheter having a size of between about 3 Fr and about 12 Fr. Further, as similarly noted above, the guidewire 767 can have a size of between about 0.005 inches and about 0.030 inches, between about 0.008 inches and about 0.024 inches, or between about 0.010 inches and about 0.018 inches, such as 0.010 inches, 0.014 inches, or 0.018 inches.

Figure 17B:
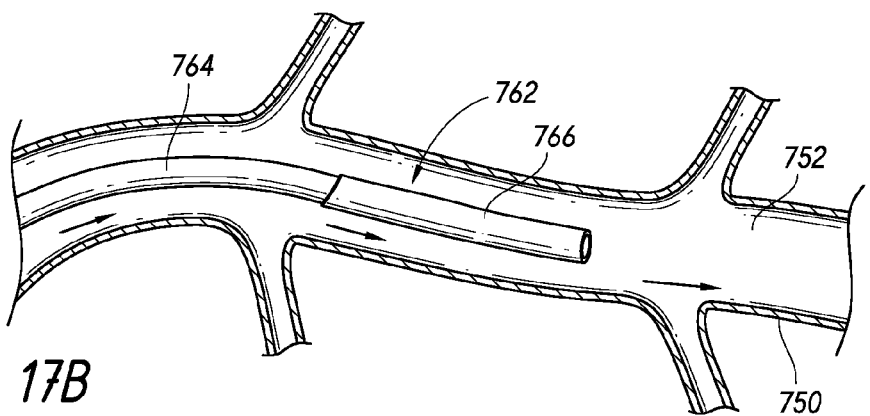
Figure 18B:
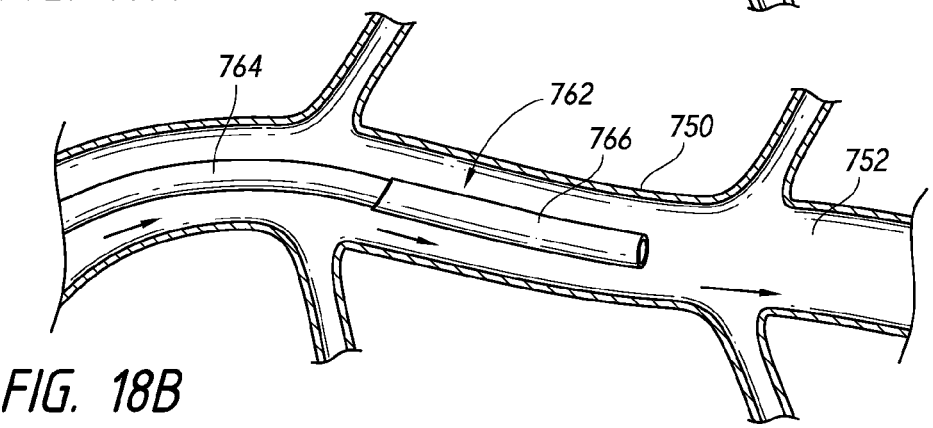
Figure 20B:
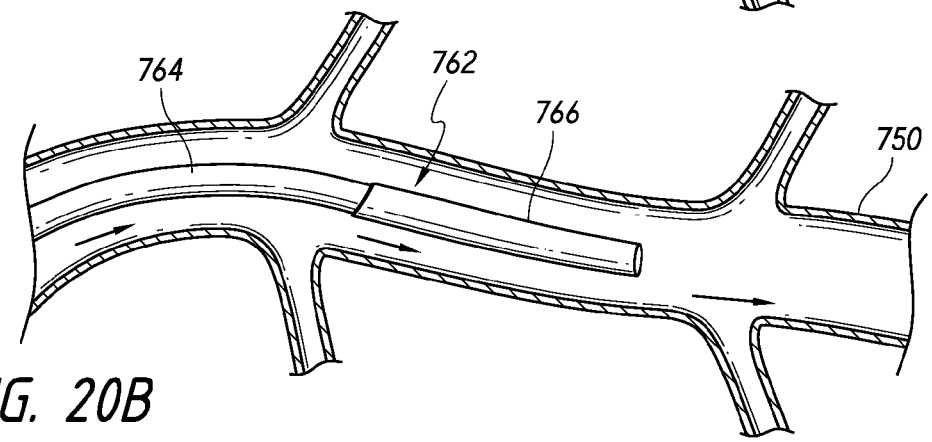

When used, as shown in FIGS. 17A, 18A, and 20A, the guide catheter 760 can be proximally withdrawn from the vessel 750, as shown in FIGS. 17B, 18B, and 20B. Thus, the implant carrier assembly 762 can be positioned at the target region whether by use of a catheter 760 or not, as shown in FIGS. 17B, 18B, 19A, and 20B.

Next, referring to FIGS. 17C, 18C, 19B, and 20C, using the deployment handle or actuation mechanism, the clinician can expand a first or second portion (or both) of the implant 766 in order to at least partially or fully occlude flow past the implant 766 into a downstream section 770 of the lumen 752. The deployment handle can be configured such as those disclosed herein and/or in co-pending U.S. patent application Ser. No. 14/044,794, filed Oct. 2, 2013, the entirety of which is incorporated herein by reference. This blockage of downstream flow through the vessel can make possible a highly targeted and concentrated delivery of material to a target region, avoiding dilution of the material in the downstream section 770 or reflux of the material 768 into an upstream region 772 of the vessel 750.

Figure 17C:
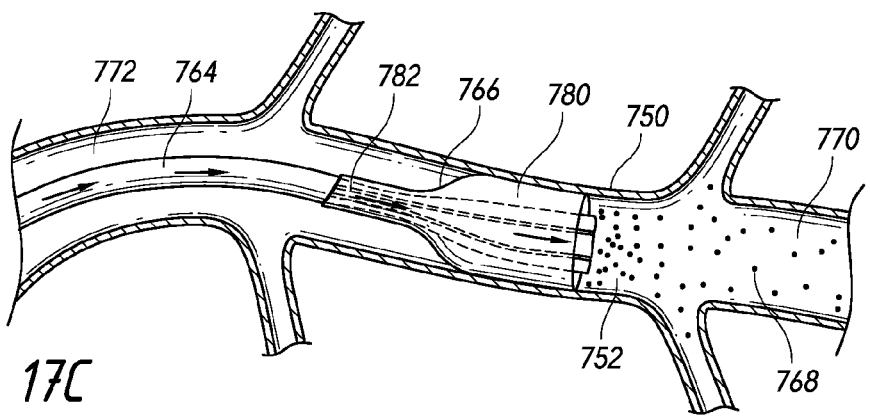

For example, in some embodiments, such as that illustrated in FIGS. 17C, 18B, and 19C, the clinician can expand a distal portion 780 of the implant 766 while maintaining a proximal portion 782 of the implant 766 in a closed state. Thus, the distal portion 780 can expand into apposition with a wall of the vessel 750, thereby occluding, substantially or fully, flow through the vessel to the downstream section 770 of the lumen 752. Accordingly, the downstream section 770 of the lumen 752 can be isolated from the upstream section 772 of the lumen 752. This occlusion or isolation can enable the clinician to provide a more targeted delivery of material 768 to a target region and avoid dilution of the material 768 in the downstream section 770 or reflux of the material 768 into an upstream region 772 of the vessel 750.

Figure 18C:
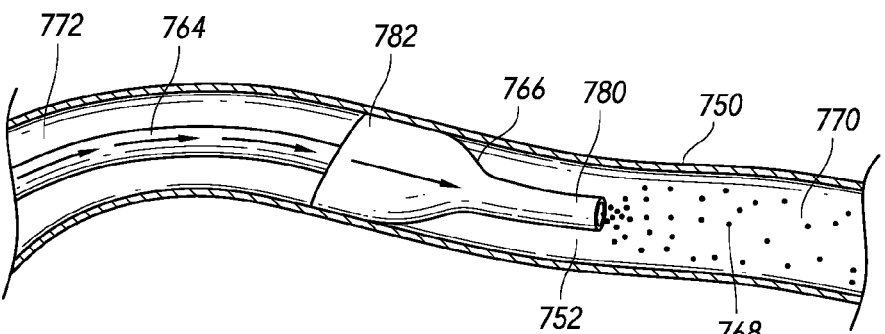

Further, in some embodiments, such as that illustrated in FIG. 18C, the clinician can expand the proximal portion 782 of the implant 766 while maintaining the distal portion 780 of the implant 766 in a closed state. Thus, the proximal portion 782 can expand into apposition with a wall of the vessel 750, thereby occluding, substantially or fully, flow through the vessel to the downstream section 770 of the lumen 752. A flushing port, such as that illustrated in the embodiments of FIGS. 1 and 2, can be used to inject fluid into the proximal portion 782 in order to facilitate expansion thereof. Once expanded, as with the embodiment illustrated in FIG. 17C, the downstream section 770 of the lumen 752 can be isolated from the upstream section 772 of the lumen 752. This occlusion or isolation can enable the clinician to provide a more targeted delivery of material 768 to a target region and avoid dilution of the material 768 in the downstream section 770 or reflux of the material 768 into an upstream region 772 of the vessel 750.

After flow has been at least partially occluded, FIGS. 17C, 18C, 19B, and 20C illustrate that the clinician can release a desired material 768 into the downstream section 770 of the lumen 752. The desired material 768 can comprise an embolic material, such as NBCA glue, liquid embolic agents, a radiopaque material, a radioactive material, drugs or other therapeutic materials. The release of such material 768 into the downstream section 770 of the lumen 752 can be performed until a desired amount or concentration of such material 768 is achieved in the downstream section 770.

In some embodiments, after desired material has been delivered and if the implant is to remain in place within the lumen, material immediately adjacent to the valve component of the implant can function to at least partially close or seal the valve component. For example, in embodiments such as those that use the implant illustrated above in FIGS. 7A-7D, an adhesive material can be released at the end of the process in order to allow the implant to self-seal. Further, in embodiments in which the implant is biased toward a closed position (see e.g., the valve component in FIGS. 9A-12B), the material (especially glues or other adhesive-type materials) can facilitate the creation of an at least partially closed or sealed valve that no longer permit flow through and out of the implant to the downstream section of the vessel. Further, the material can tend to facilitate thrombosis or coagulation of blood to further occlude the lumen (see e.g., FIGS. 8A-8B).

Figure 17D:
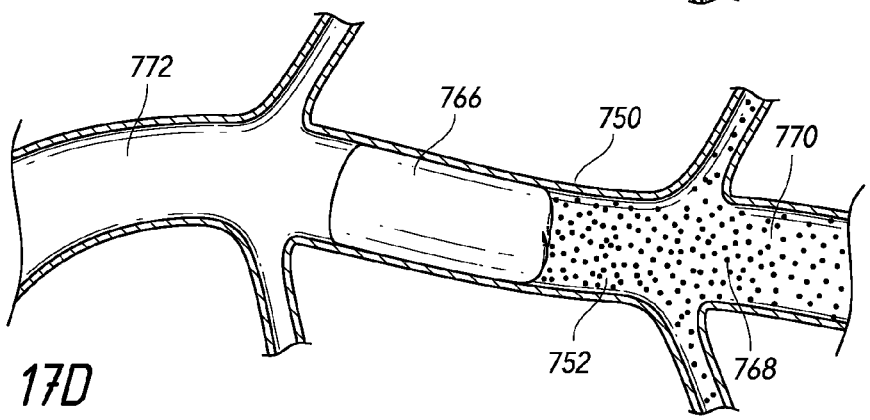
Figure 18D:
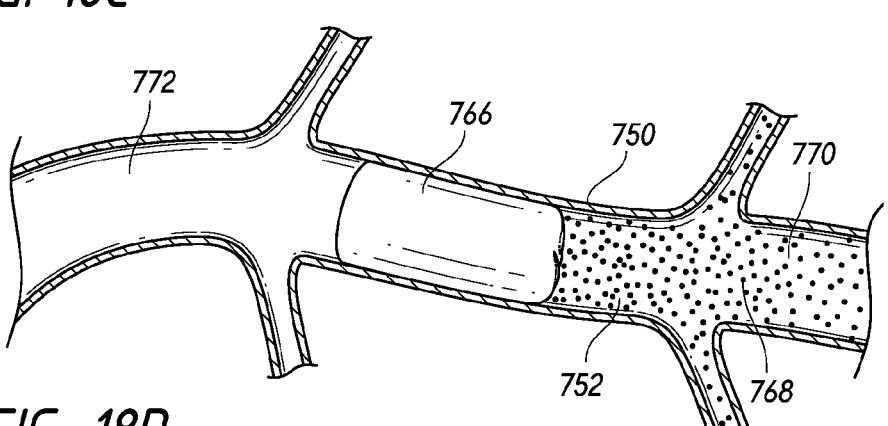
Figure 20C:
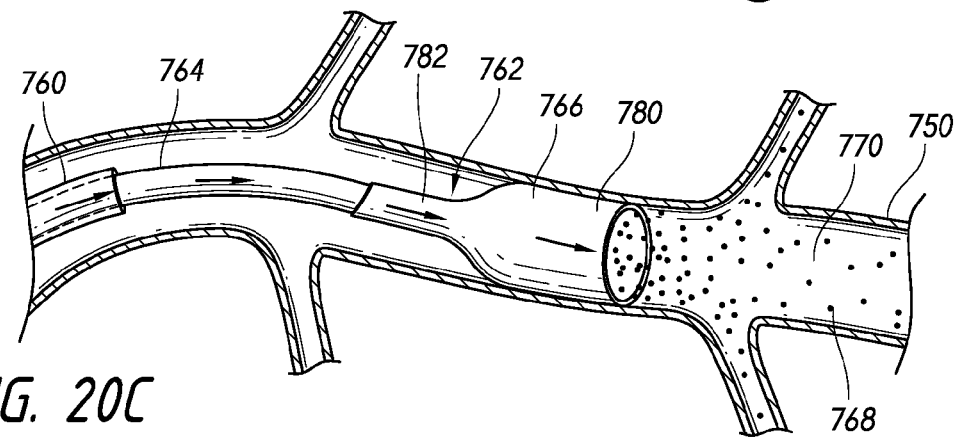
Figure 20D:
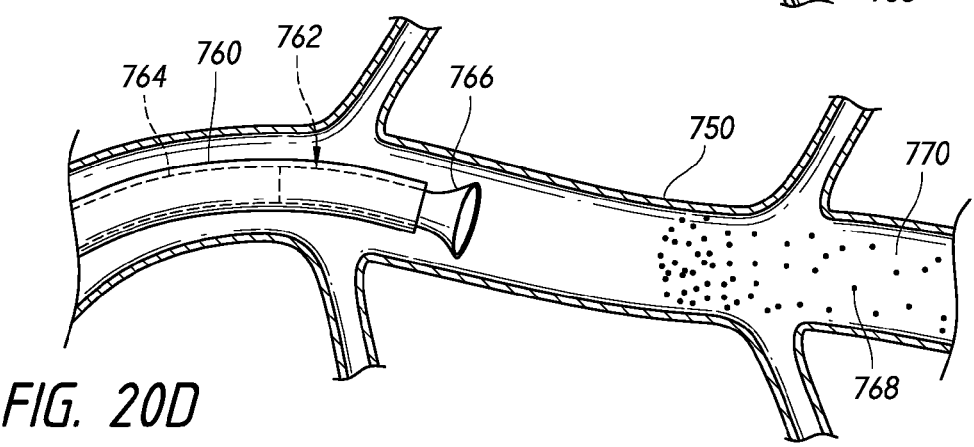

In some embodiments, the remaining portion of the implant 766 is expanded or released and the catheter 764 can be removed from the vessel 750, as shown in FIGS. 17D, 18D, and 19C. However, in some embodiments, the implant 766 and the catheter 764 can be removed from the vessel 750. For example, FIGS. 20C-20D illustrate that the guide catheter 760 can be maintained adjacent to the implant 766 such that after material has been deployed from the assembly 762, the assembly 762 can be proximally withdrawn into the guide catheter 760. In some embodiments, the guide catheter 760 can be distally advanced over the assembly 762 such that the implant 766 is not moved relative to the blood vessel 750.

According to some embodiments, implants can be deployed in lumens having dimensions of between about 2 mm and about 20 mm. The target delivery profile can be about 6 Fr or smaller. For example, the implant assembly can be compatible with a guide catheter having a size of between about 3 Fr and about 12 Fr.

According to some embodiments, implants disclosed herein can have a fibrous membrane feature can be used in various clinical applications, as discussed above. According to some embodiments, implants disclosed herein having a fibrous membrane feature can have an expanded diameter of between about 3 mm and about 22 mm.

In addition, the methods and procedures discussed above with respect to FIGS. 17A-20D can be implemented in accordance with further aspect shown in FIGS. 21-24B. For procedures that deliver an embolic agent comprising radioactive particles for additional radiological treatment of a tumor, the procedure must precisely deliver the material the target region. Such delivery must be well-controlled delivery and calibrated in order to protect a patient from the unnecessary additional risks that may occur should the material being improperly distributed within other areas of the downstream vasculature.

Figure 21:
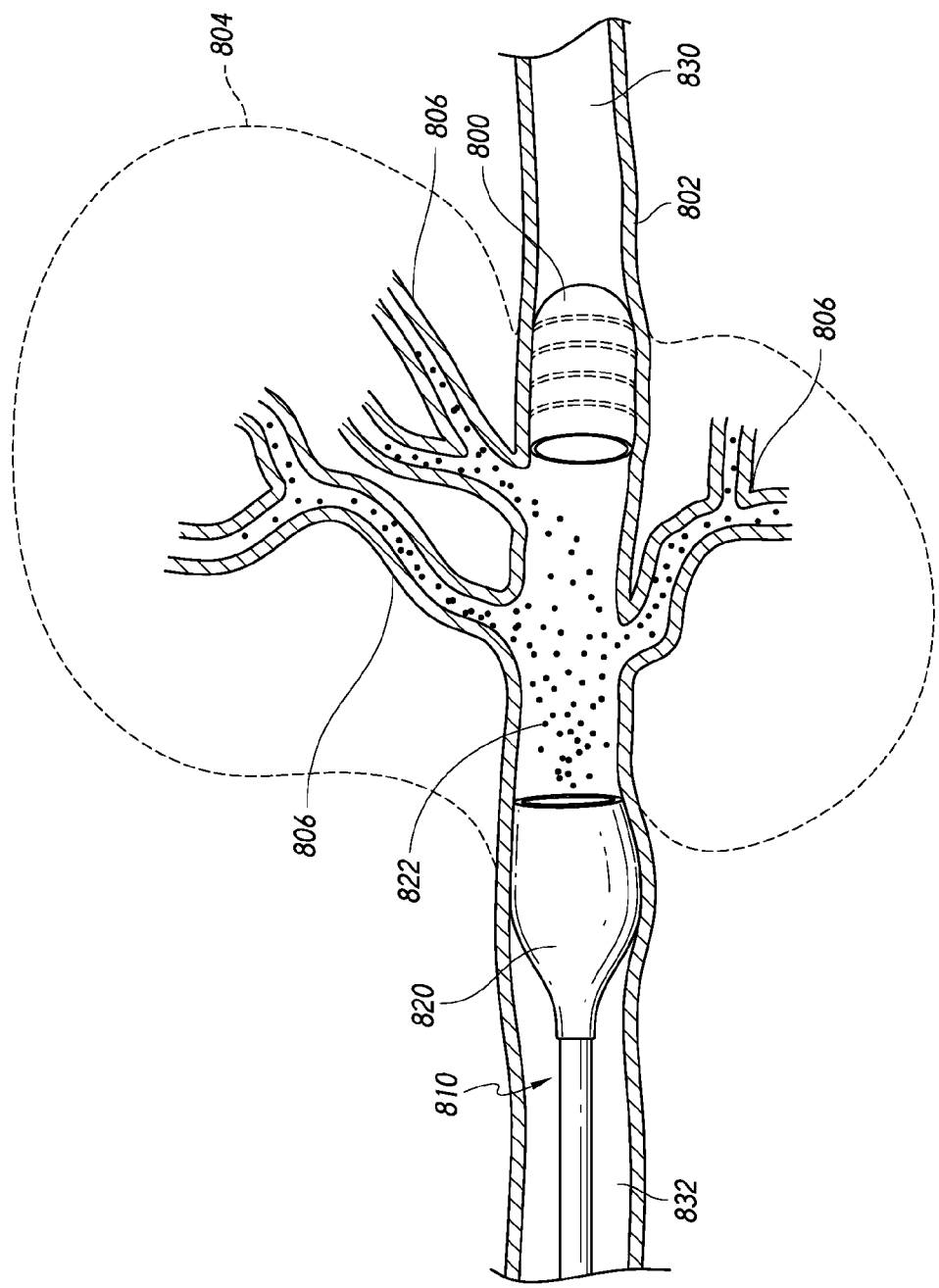
FIG. 21 is a cross-sectional schematic view illustrating deposition of embolic particles into a target vessel region, according to some embodiments.

For example, FIG. 21 illustrates an embodiment of a procedure in which a first implant 800 is deployed into a vessel 802 adjacent to a target structure, vasculature, or lesion 804. The target structure 804 can be fed by a series of arteries 806. After placing the first implant 800 in a location downstream of the arteries 806 to prevent flow of a delivered material (e.g., embolic material) to downstream vasculature, an implant assembly 810 can be advanced to a location within the vessel 802 that is proximal to the target arteries 806 and the first implant 800. The implant assembly 810 and the first implant 800 can be spaced apart in close proximity to each other to allow flow to only those target arteries 806 and to shield flow to other unintended areas. For example, the implant assembly 810 and the first implant 800 can be spaced apart in a range of from about 0.1 inches to about 5 inches, about 0.5 inches to about 3 inches, about 0.8 inches to about 2 inches, about 1 inches to about 1.5 inches, or about 1.2 inches to about 1.4 inches. Various ranges of spacing between the implant 800 and the assembly 810 can be achieved to precisely target a region of the vessel 802 and/or select arteries 806.

In the illustrated embodiment of FIG. 21, a distal portion of a second implant 820 is expanded into apposition with the walls of the vessel 802 in order to at least partially block anterograde flow to the arteries 806. A material 822 can then be released into the space between the first and second implants 800, 820. The material can thus be concentrated toward the arteries 806, thereby enhancing the efficacy of the delivery. Thereafter, additional steps or procedures can be performed, such as imaging, in order to further treat the vessel 802 or target structure 804.

As noted above, the first and/or second implants 800, 820 can be released and left in the vessel 802 in order to provide occlusion of the vessel. However, according to some embodiments, one or both of the first or second implants 800, 820 can be removed from the vessel 802 after the material has been delivered to the arteries 806 and target structure 804. Thus, procedures can be provided that allow temporary occlusion of a blood vessel in order to treat a target structure while thereafter being able to restore blood flow through the previously occluded artery.

Figure 22:
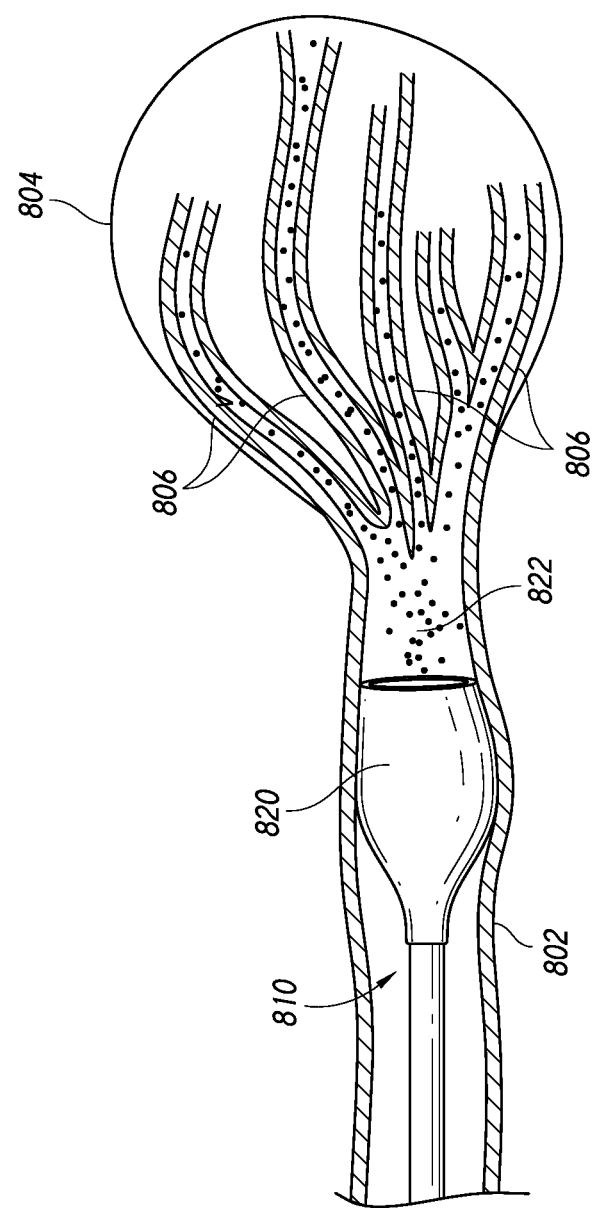
FIG. 22 is a cross-sectional schematic view illustrating deposition of embolic particles into a target vessel region, according to some embodiments.

FIG. 22 illustrates the delivery of a material 822 toward arteries 806 and a target structure 804. In this embodiment, an implant assembly 810 has been advanced to a location adjacent to the target structure 804. Thereafter, the implant 820 is expanded into apposition with the walls of the blood vessel 802. The material 822 can then be released into the downstream areas of the vessel 802 and arteries 806. Thus, the material 822 can be advanced downstream toward the target structure 804. Thereafter, the implant 820 can be expanded and released, such that blood flow to the target structure 804 is restricted or eliminated, thus inducing infarction of the target structure 804.

Such embodiments advantageously mitigate any upstream migration of the material 822 toward an upstream section 832 of the vessel, and can tend to enhance or increase the concentration of material delivered to the arteries 806 and target structure 804. In some embodiments, the procedure can also mitigate any downstream migration of the material 822 toward a downstream section 830 of the vessel. Further, such a dual-implant system or procedure can also mitigate any upstream migration of the material 822 toward an upstream section 832 of the vessel 802. Embodiments of this technique allow confident and precise application of material in any of a variety of situations, such as those mentioned above.

As discussed herein and as illustrated with respect to FIGS. 17A-22, various treatment procedures can be performed for a target body region, such as tumor devascularization, reducing traumatic bleeding or hemorrhage, high-flow vascular malformations, vascular or airway volume reduction procedures, treatment of a target lesion, treatment and embolization of incompetent venous systems in low extremities (e.g., legs and lower abdominal area), treatment varicose veins in the leg (e.g., great saphenous vein and spider veins in deeper system), attending to other indications such as AVM, pelvic varices, etc. In some situations, a single treatment may not be sufficient to fully devascularize, heal, or otherwise treat the target body region.

Therefore, according to some embodiments, after a first treatment or procedure in which a first occlusive implant has been released into a vessel or artery and remained thereat, at least partially occluding the vessel for a given period of time, a second procedure can be performed to remove and/or modify the first occlusive implant using the catheter and/or a second occlusive implant.

For example, depending on the therapeutic strategy, if a clinician believes that the target body region may benefit from a second treatment or procedure, a second procedure can be undertaken in which the first occlusive implant can be removed and/or modified. The second procedure can be performed after one, two, three, four, five or six months, or longer, and depends on the health of the patient and need for such a procedure.

The second procedure can be performed by removing the first implant and/or modifying the first implant, such as by restoring flow through a valve of the first implant. The first option for the second procedure comprises removing the first implant from the vessel using a removal device. After removal, the first implant can be replaced by a new, second implant.

Another option for the second procedure comprises modifying the first occlusive implant, such as by restoring flow through the first implant, physically altering the first implant 970 (see FIGS. 23A-23B), injecting additional material toward the target region, and/or inserting a second implant 980 into the first implant 970 (see FIGS. 24A-24B) so as to change the effect or degree of the occlusion or permit additional material to be deployed downstream of the first implant 970.

In some embodiments, the first implant 970 can be modified by penetrating or punching a hole or aperture in the cover member or otherwise removing a portion of the first implant 970. The punching can comprise disconnecting, opening, or otherwise tearing a valve component from the first implant distal portion. The hole or aperture can be made in order to restore flow at least partially through the first implant 970, thereby allowing revascularization of the target body region.

Figure 23A:
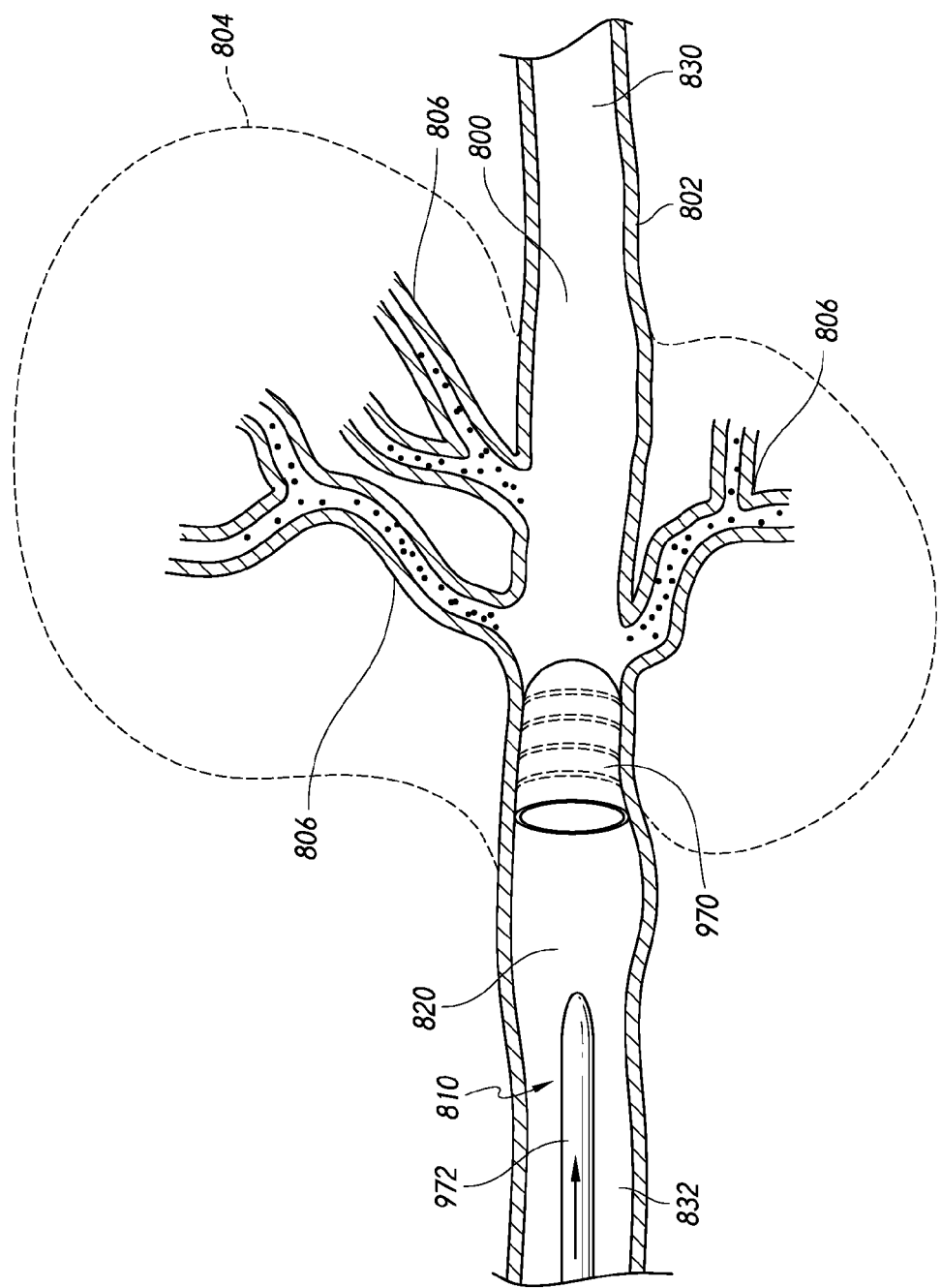
FIGS. 23A-23B illustrate schematic views illustrating alteration of an implanted occlusive device, according to some embodiments.
Figure 23B:
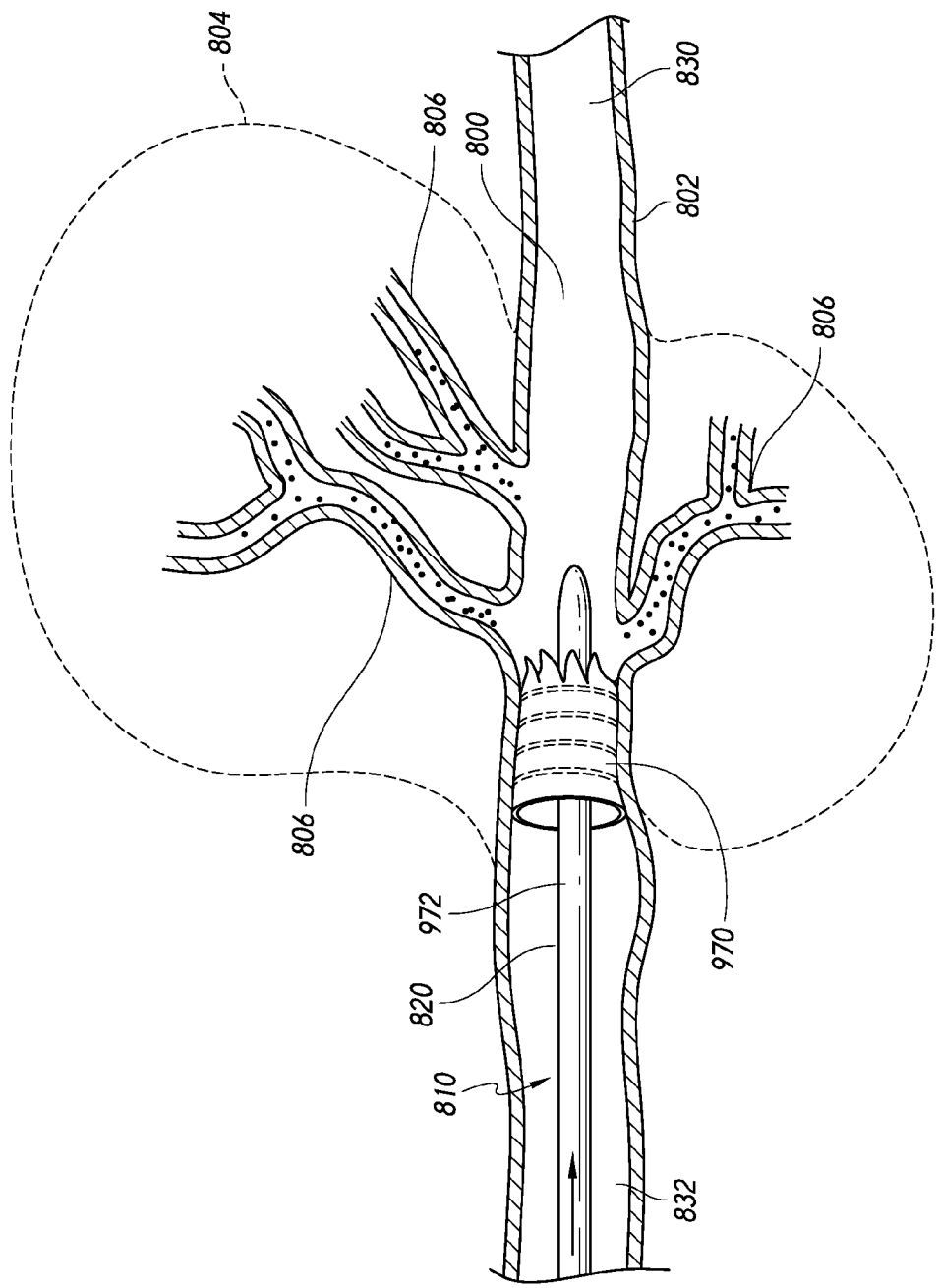

For example, FIG. 23A illustrates that when the first occlusive implant 970 is left in the vessel 802, the clinician can advance a catheter, wire, or other adjustment member 972 to the target body region where the first implant 970 is deployed. When the adjustment member 972 is positioned adjacent to the first implant 970, the adjustment member 972 can be used to create a hole or aperture in the distal portion of the first implant 970 by advancing a distal tip of the adjustment member 972 through the membrane or cover member of the first implant 970, as illustrated in FIG. 23B.

Thus, if determined appropriate, such revascularization can provide the final step to the procedure and no further occlusion may be necessary. However, as necessary, additional optional steps can be taken to occlude or otherwise treat the target region.

Once the first implant 970 has been modified, and flow has been restored, a further procedure may be performed. If the deposition of another material, such as an embolic material, contrast agent, or drug, is recommended for the target body region, such material can then be deposited toward the target region. For example, after revascularizing the vessel, the clinician can deposit additional material toward the target region without delivering an additional implant to at least partially occlude the vessel. However, in some embodiments, the injection of additional material can include using and/or placing a second implant in the vessel. The second implant can comprise any of the implants disclosed herein or be operated using any of the methods disclosed herein, such as any of the methods or treatment procedures illustrated in FIGS. 17A-22.

Figure 24A:
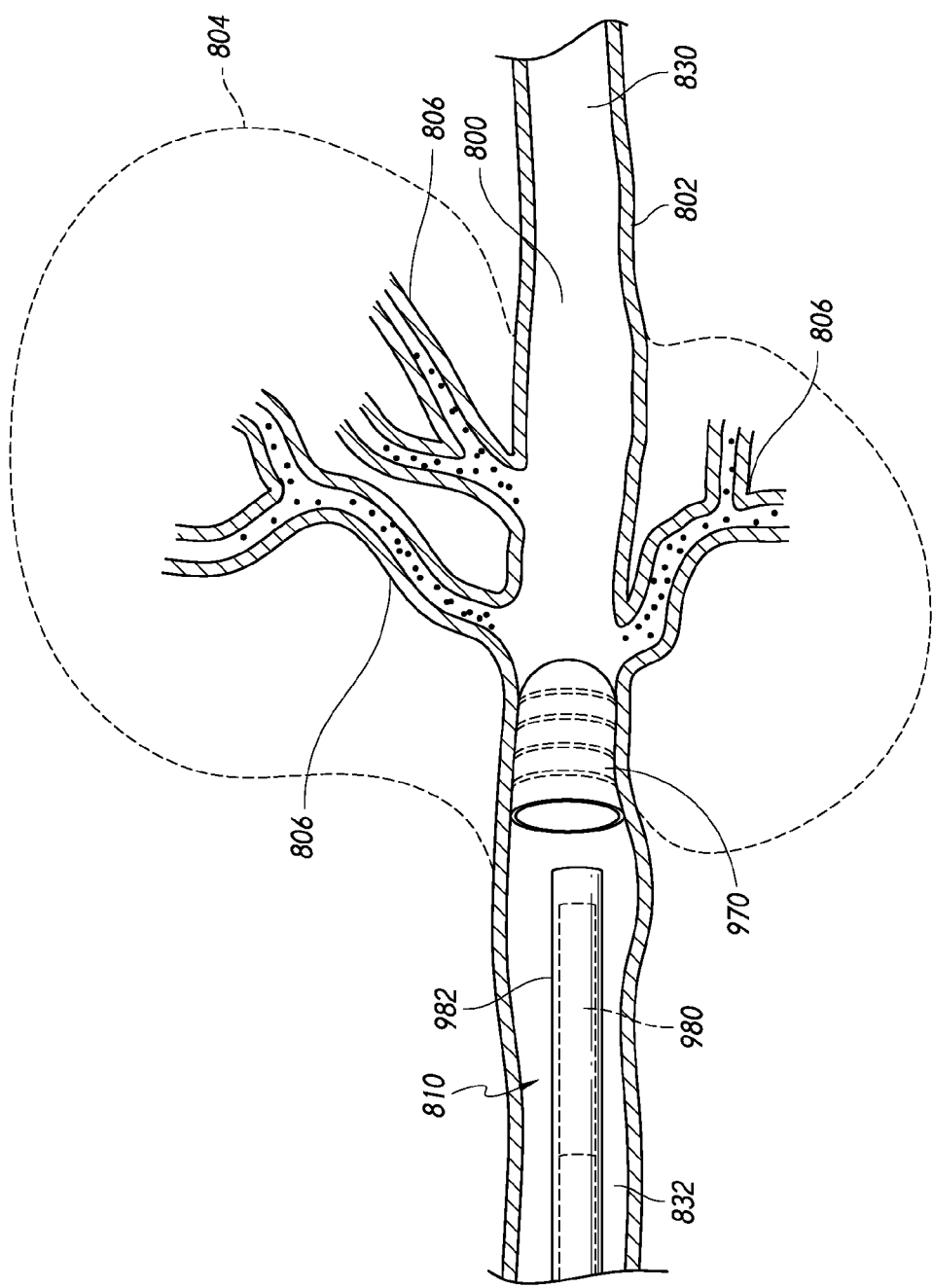
FIGS. 24A-24B illustrate schematic views illustrating alteration of an implanted first occlusive device and the insertion of a second device into the first device, according to some embodiments.
Figure 24B:
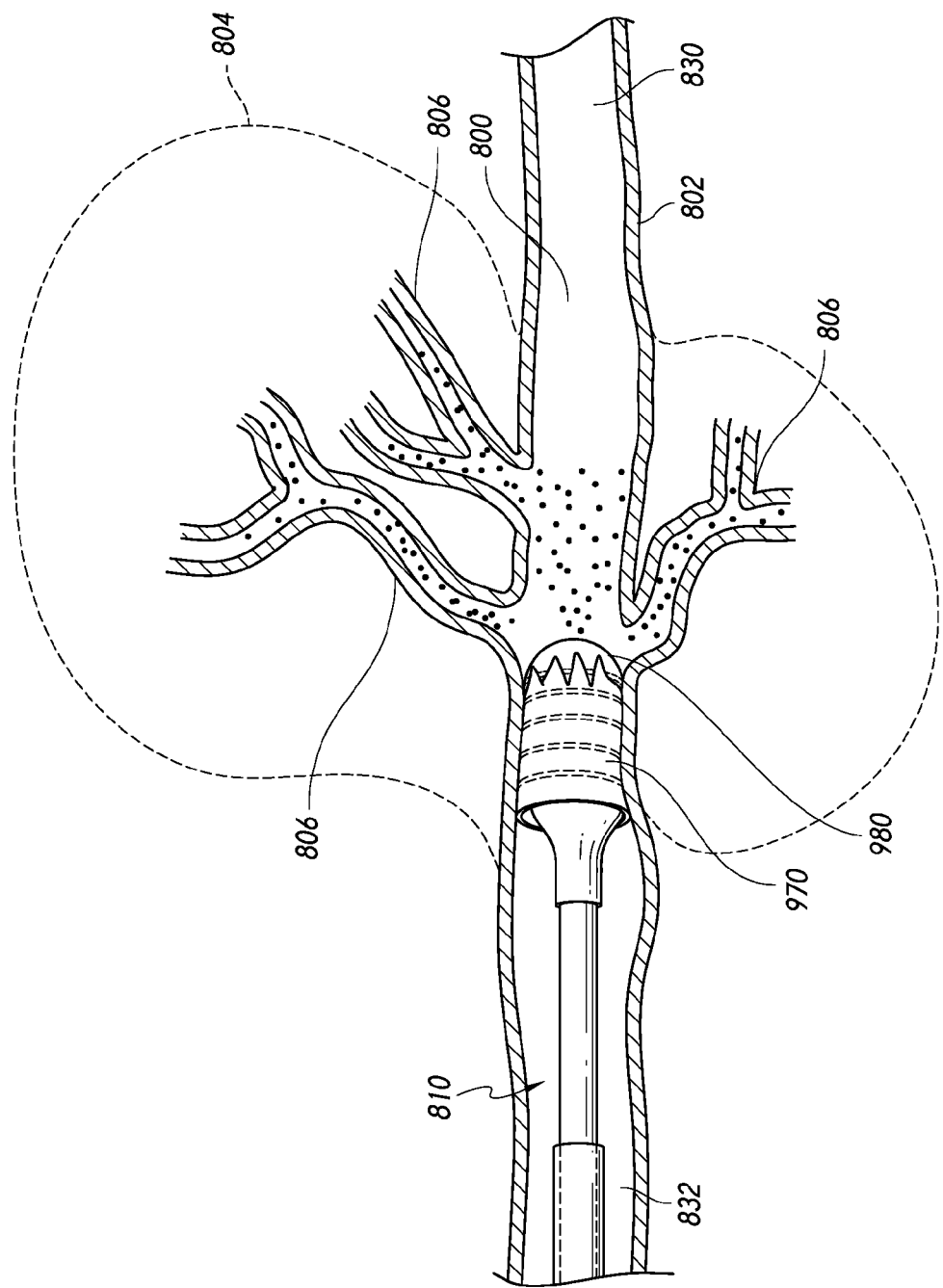

Referring to FIGS. 24A-24B, whether or not a further material is injected into the lumen, a second implant 980 can be placed proximally of the first implant within the lumen. In some embodiments, the second implant 980 can be configured to fit within the lumen of the first implant. Further, in some embodiments, such as that illustrated in FIG. 24A, the piercing or opening of the distal portion of the first implant 970 can be performed by using the catheter 982 used to deliver the second implant 980. For example, the distal end of the catheter 982 can be advanced distally through the distal portion of the first implant 970, thus opening the first implant 970 in a manner similar to that discussed above with respect to FIGS. 23A-23B.

In the embodiment shown in FIG. 24A, modification of the first implant 970 and the further treatment of the target body region can be performed by modifying, penetrating, or punching a hole or aperture into the first implant 970 in a central location of the distal portion of the first implant 970, as noted above, and positioning a distal portion of the second implant 980 within the first implant 970. However, the valve component of the first implant 970 can be maintained interconnected with at least a portion of the first implant 970, such as with the cover member or frame member. Thus, after being dislocated relative to the first implant, the valve component can remain attached to the first implant 970, thereby preventing release of the valve component into distal vasculature. Later use of embolic material, glue, or other such materials can allow the dislocated valve component to be more securely fixed or adhered relative to the first implant 970.

In some embodiments, the second implant 980 can be coupled to or attached to the first implant 970 when released into the lumen. For example, the second implant 980 can sit entirely within the first implant 970. However, a distal portion of the second implant 980 can be configured to extend distally beyond the distal portion of the first implant 970 to facilitate passage of a material therethrough.

The second implant 980 can then be used in a manner as discussed herein with respect to other embodiments, such as for providing a material to a downstream target region.

Additionally, although the illustrated methods and procedures shown and described with respect to FIGS. 17A-24B illustrate embodiments in which the implant comprises a helical support component that can be coupled to a catheter (see e.g., FIGS. 3-12B), such methods and procedures can also be implemented using an implant that has a deflectable support component that can be at advanced within a catheter (see e.g., FIGS. 13-16B). Further, any of the valve components disclosed herein (see e.g., FIGS. 7A-16B) can be used with a helical support component that can be coupled to a catheter (as shown in FIGS. 3-12B) or a deflectable support component that can be at advanced within a catheter (as shown in FIGS. 13-16B), including any combinations or modifications thereof.

According to various aspects of the subject technology, implants disclosed herein may be used for various applications for reducing or stopping flow through a luminal structure in a patient and inducing infarction of a target tissue. Implants of the subject technology may be used for rapid, well-controlled, and reliable occlusion of luminal structures. For example, the luminal structure may comprise at least one of a blood vessel, a body organ, a lung, an airway, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. In some embodiments, implants of the present disclosure may be used for temporary occlusion in cases of lung disease, or for temporary occlusion of female reproductive organs for contraceptive purposes. In some embodiments, implants of the present disclosure may be removed, or flow may be restored through the luminal structure to restore original organ functions.

In addition to the applications mentioned above, some embodiments of the implants of the present disclosure may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). In some embodiments, implants of the present disclosure may be used for stopping blood loss from a damaged blood vessel, closing an abnormal blood vessel or a blood vessel supplying a vascular anamaly, or interrupting blood supply to an organ or part of an organ for permanent devascularization (e.g., closure of splenic artery in spleen laceration, devascularization of tissues involved by neoplastic process, either pre-operatively or as a palliative measure). In some embodiments, implants of the present disclosure may be used for various endovascular (e.g., neural and peripheral) procedures, head and neck AVFs, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, etc.), and devascularization prior to (or as an alternative to) surgical resection of various organs or tumors.

In certain embodiments, implants of the present disclosure may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to transjugular intrahepatic portosystemic shunt ("TIPS"), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of ureteroarterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary AVFs, transarterial embolization of Blalock-Taussig shunts). The application of implants of the present disclosure is not limited to applications for human patients, but may also include veterinary applications.

According to various embodiments of the subject technology, a cover component of an implant may be used to occlude, partially or completely, luminal structure in which a respective implant is deployed. In some embodiments as used herein, occlusion may refer to either partial or complete occlusion. In some embodiments, cover components can comprise at least one of a polyurethane, a polyanhidrate, PTFE, ePTFE, silicone, and other suitable materials known to those of ordinary skill in the art. In some embodiments, cover components may be elastic. In some embodiments, cover components may be permeable or non-permeable.

In some embodiments, an average thickness of a cover component can be between about 0.0005 inches and about 0.006 inches. In some aspects, the average thickness of a cover component may be less than about 0.0005 inches or greater than about 0.006 inches. In certain embodiments, an average thickness of a distal portion of a cover component is greater than an average thickness of a proximal portion of a cover component. Such a configuration may ensure that more flow may be reduced at the distal portion of a cover component. In some embodiments, the average thickness of the distal portion of a cover component is between about 0.002 inches and about 0.012 inches. In some embodiments, the average thickness of the distal portion of a cover component may be less than about 0.002 inches or greater than about 0.012 inches. In some embodiments, the average thickness of the proximal portion of a cover component is between about 0.0005 inches and about 0.006 inches. In some embodiments, the average thickness of the proximal portion of a cover component may be less than about 0.0005 inches or greater than about 0.006 inches.

Some embodiments of the implant described herein can incorporate one or more features of implants and/or implant deployment systems The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. A material delivery device, comprising:
an expandable support member having a lumen and an outflow end, the support member comprising a pair of wires collectively forming a series of loops being configured to expand from a collapsed configuration to an expanded configuration for placement in a body lumen;
a cover component, extending along the support member, defining an aperture at a distalmost loop at the outflow end of the support member; and
a valve component comprising nonmovable and movable components, the nonmovable component being coupled to the distalmost loop, the movable component being coupled to the nonmovable component via a plurality of fasteners about an entire periphery thereof to permit the movable component to move between (i) an open position, wherein the movable component is evenly spaced apart distally from a distal end of the support member to permit outflow of a material through the aperture via a gap extending about the entire periphery of the movable component, and (ii) a closed position, wherein the movable component abuts the nonmovable component to close the gap and restrict backflow of the material into the aperture.

2. A material delivery device, comprising:
an expandable support member comprising a pair of wires collectively forming a series of loops including a distalmost loop; and
a valve component attached to the distalmost loop, the valve component comprising a movable component and a nonmovable component, the nonmovable component comprising a through opening and a peripheral edge, the nonmovable component being coupled along an entirety of the peripheral edge to a perimeter of the distalmost loop, the movable component being coupled to the nonmovable component via a plurality of fasteners about the entire peripheral edge to permit the movable component to be positionable at (i) an open position in which the movable component is evenly spaced apart distally from the distalmost loop to permit outflow of a material through the opening via a gap extending about an entire periphery of the movable component, and (ii) a closed position in which the movable component is positioned against the nonmovable component to close the gap and cover the through opening.

3. The material delivery device of claim 2, wherein the nonmovable component is attached directly to the distalmost loop.

4. The material delivery device of claim 2, further comprising a cover component, extending along the support member.

5. The material delivery device of claim 4, wherein the nonmovable component comprises a material separate from the cover.

6. The device of claim 2, wherein the movable component comprises a circular plate.

7. The device of claim 2, wherein the movable component comprises a conical member.

8. The device of claim 2, wherein the nonmovable component comprises an annular member coupled to the support member.

9. The device of claim 8, wherein the movable component comprises a profile that is larger than a size of the opening in the nonmovable component.

10. The device of claim 9, wherein the profile of the movable component comprises an outer diameter that is larger than an inner diameter of the opening in the nonmovable component.

11. A material delivery device, comprising:
an expandable support member comprising a pair of wires collectively forming a series of loops including a distalmost loop defining an opening therethrough;
a cover component coupled to and extending along the support member; and
a valve component comprising a material separate from the cover component and comprising nonmovable and movable components, the nonmovable component being coupled to and movable relative to the distalmost loop, and the movable component being coupled to the nonmovable component via a plurality of fasteners about an entire periphery thereof to permit the movable component to move between (i) an open position in which the movable component is evenly spaced apart distally from the distalmost loop to permit outflow of a material through the opening via a gap extending about an entire periphery of the movable component and (ii) a closed position in which the movable component is positioned against nonmovable component to close the gap and restrict backflow of the material into the opening.

12. The device of claim 11, wherein the nonmovable component is attached directly to the distalmost loop.

13. The device of claim 11, wherein the valve component comprises a circular plate.

14. The device of claim 11, wherein the valve component comprises a conical member.

15. The device of claim 11, wherein the valve component comprises an annular member coupled to the support member.

16. The device of claim 15, wherein the nonmovable component comprises the annular member, the movable component having a profile that is larger than a size of an opening in the nonmovable component.

17. The device of claim 16, wherein the profile of the movable component comprises an outer diameter that is larger than an inner diameter of the opening in the nonmovable component.

18. The device of claim 1, wherein the nonmovable component is attached directly to the distalmost loop.

19. The device of claim 1, wherein a profile of the nonmovable component comprises a circular plate.

20. The device of claim 1, wherein the movable component comprises a conical member.

21. The device of claim 1, wherein the nonmovable component comprises an annular member coupled to the support member.

22. The device of claim 21, wherein the movable component has a cross sectional profile that is larger than a size of an opening in the nonmovable component.

23. The device of claim 22, wherein the cross-sectional profile of the movable component comprises an outer diameter that is larger than an inner diameter of the opening in the nonmovable component.

24. The device of claim 1, wherein the plurality of fasteners comprises at least one of a hinge-type fastener, a strap-type fastener, or a material having one or more apertures extending therethrough.

25. The device of claim 1, wherein the nonmovable component and the movable component each have matching shapes to facilitate closing of the gap and restriction of backflow of material into the aperture.

26. The device of claim 25, wherein the shapes of the nonmovable and movable components comprise mating components such that the nonmovable and movable components assume a substantially fixed rotational orientation relative to each other in the closed position.

* * * * *